US012127926B2

(12) United States Patent
Conti

(10) Patent No.: US 12,127,926 B2
(45) Date of Patent: Oct. 29, 2024

(54) INTRAVAGINAL SUPPORT DEVICES AND METHODS

(71) Applicant: WATKINS-CONTI PRODUCTS, INC., Edmond, OK (US)

(72) Inventor: Allison Conti, Edmond, OK (US)

(73) Assignee: Watkins-Conti Products, Inc., Edmond, OK (US)

(*) Notice: Subject to any disclaimer, the term of this patent is extended or adjusted under 35 U.S.C. 154(b) by 143 days.

(21) Appl. No.: 17/555,098

(22) Filed: Dec. 17, 2021

(65) Prior Publication Data

US 2022/0183812 A1 Jun. 16, 2022

Related U.S. Application Data

(63) Continuation of application No. 16/355,638, filed on Mar. 15, 2019, now Pat. No. 11,291,535.

(60) Provisional application No. 62/735,605, filed on Sep. 24, 2018, provisional application No. 62/687,119, filed on Jun. 19, 2018, provisional application No. 62/644,340, filed on Mar. 16, 2018.

(51) Int. Cl.
A61F 2/00 (2006.01)
A61F 6/08 (2006.01)

(52) U.S. Cl.
CPC ............ *A61F 2/005* (2013.01); *A61F 2/0022* (2013.01); *A61F 6/08* (2013.01)

(58) Field of Classification Search
None
See application file for complete search history.

(56) References Cited

U.S. PATENT DOCUMENTS

| 1,996,242 | A | 4/1935 | Hagedorn |
| 2,089,113 | A | 8/1937 | Chalmers |
| 2,534,900 | A | 12/1950 | Chalmers |
| 2,613,670 | A | 10/1952 | Sokolik |
| 2,638,093 | A | 5/1953 | Kulick |
| 2,763,265 | A | 9/1956 | Waters |
| D222,013 | S | 9/1971 | Thomas et al. |
| 3,626,942 | A | 12/1971 | Waldron |
| 3,845,766 | A | 11/1974 | Zoller |
| D250,049 | S | 10/1978 | Hite, Jr. |

(Continued)

FOREIGN PATENT DOCUMENTS

| CN | 209734284 U | 12/2019 |
| DE | 202009008893 U1 | 6/2009 |

(Continued)

OTHER PUBLICATIONS

First Office Action from Chinese Application No. 201980019605.6 dated Jan. 31, 2023.

(Continued)

*Primary Examiner* — Christine H Matthews
(74) *Attorney, Agent, or Firm* — Michele V. Frank; Venable LLP

(57) ABSTRACT

The present disclosure, in certain embodiments, relates to a flexible and non-absorbent vaginal insert device that is easier to insert and remove and is for use in improving and preventing symptoms associated with pelvic organ prolapse and urinary and/or fecal incontinence when the device is inserted. In certain embodiments, the device has an optionally cone-shaped upper portion that provides pelvic organ support and a removal portion or stem that facilitates insertion and removal of the device.

23 Claims, 65 Drawing Sheets

(56) References Cited

U.S. PATENT DOCUMENTS

| | | |
|---|---|---|
| 4,286,593 A | 9/1981 | Place et al. |
| 4,825,686 A | 5/1989 | Marsh |
| D306,347 S | 2/1990 | Gyurik |
| D323,212 S | 1/1992 | Crawford |
| 5,295,984 A | 3/1994 | Contente et al. |
| 5,782,745 A | 7/1998 | Benderev |
| 5,813,973 A | 9/1998 | Gloth |
| 5,827,248 A | 10/1998 | Crawford |
| D430,669 S | 9/2000 | Buck et al. |
| 6,170,484 B1 | 1/2001 | Feng |
| 6,413,206 B2 | 7/2002 | Biswas |
| 6,503,190 B1 | 1/2003 | Ulmsten et al. |
| 6,558,370 B2 | 5/2003 | Moser |
| 6,733,438 B1 | 5/2004 | Dann et al. |
| 6,746,432 B2 | 6/2004 | Zadini et al. |
| 6,770,025 B2 | 8/2004 | Zunker |
| 6,773,421 B2 | 8/2004 | Bosselaar et al. |
| 7,577,476 B2 | 8/2009 | Hochman et al. |
| 7,771,344 B2 | 8/2010 | Ziv |
| 7,779,843 B2 | 8/2010 | Astani et al. |
| 7,892,163 B2 | 2/2011 | Bartning et al. |
| D655,415 S | 3/2012 | Chaffringeon |
| D661,390 S | 6/2012 | McLain |
| D661,392 S | 6/2012 | McLain |
| 8,302,608 B2 | 11/2012 | Harmanli |
| 8,652,026 B2 | 2/2014 | Zunker |
| 8,690,847 B2 | 4/2014 | Norman |
| 8,795,248 B2 | 8/2014 | Shihata |
| D717,950 S | 11/2014 | Agrawal |
| D719,653 S | 12/2014 | Agrawal |
| 8,911,344 B2 | 12/2014 | Altan et al. |
| 8,926,493 B2 | 1/2015 | Karapasha |
| 9,022,919 B2 | 5/2015 | Ellefson et al. |
| D741,479 S | 10/2015 | Agrawal |
| D746,452 S | 12/2015 | Petrova |
| 9,198,748 B2 | 12/2015 | Ziv et al. |
| D760,897 S | 7/2016 | Teo |
| 9,402,703 B2 | 8/2016 | Ziv et al. |
| 9,408,685 B2 | 8/2016 | Hou et al. |
| D767,759 S | 9/2016 | Mcmillon-Nixon |
| 9,555,168 B2 | 1/2017 | Browning |
| 9,918,702 B2 | 3/2018 | Tariyal et al. |
| 10,188,545 B2 | 1/2019 | Conti |
| 10,729,464 B1 | 8/2020 | Booher, Sr. |
| 11,000,402 B2 | 5/2021 | Park |
| 11,291,535 B2 | 4/2022 | Conti |
| 11,446,011 B2 | 9/2022 | Tariyal et al. |
| 2002/0007106 A1 | 1/2002 | Biswas |
| 2003/0149334 A1 | 8/2003 | Ulmsten et al. |
| 2004/0054252 A1 | 3/2004 | Zunker |
| 2004/0249238 A1 | 12/2004 | Farrell |
| 2007/0203429 A1 | 8/2007 | Ziv |
| 2008/0077097 A1 | 3/2008 | Chambers et al. |
| 2008/0149109 A1 | 6/2008 | Ziv |
| 2009/0095304 A1 | 4/2009 | Richardson et al. |
| 2009/0266367 A1 | 10/2009 | Ziv et al. |
| 2009/0283099 A1 | 11/2009 | Harmanli |
| 2010/0145137 A1 | 6/2010 | Morgan |
| 2010/0217068 A1 | 8/2010 | Ziv et al. |
| 2010/0312204 A1 | 12/2010 | Sheu |
| 2011/0065980 A1 | 3/2011 | Ziv et al. |
| 2011/0295058 A1 | 12/2011 | Henriksson et al. |
| 2012/0259167 A1 | 10/2012 | Karapasha et al. |
| 2013/0110060 A1 | 5/2013 | Shihata |
| 2013/0138134 A1 | 5/2013 | Elman et al. |
| 2014/0000628 A1 | 1/2014 | Clark et al. |
| 2014/0000629 A1 | 1/2014 | Durling et al. |
| 2014/0039245 A1 | 2/2014 | Ziv |
| 2014/0100416 A1 | 4/2014 | Durling et al. |
| 2014/0100417 A1 | 4/2014 | Durling et al. |
| 2015/0265456 A1 | 9/2015 | Booher, Sr. |
| 2016/0278988 A1 | 9/2016 | Knox |
| 2017/0049609 A1 | 2/2017 | Conti |
| 2017/0281325 A1 | 10/2017 | Rosen et al. |
| 2017/0360594 A1 | 12/2017 | Park |
| 2018/0028350 A1 | 2/2018 | Wilson et al. |
| 2018/0242957 A1 | 8/2018 | Tariyal et al. |
| 2018/0344300 A1 | 12/2018 | Burrows et al. |
| 2019/0117443 A1 | 4/2019 | Conti |
| 2019/0282350 A1 | 9/2019 | Conti |
| 2020/0078208 A1 | 3/2020 | Stoebe-Latham |
| 2022/0396836 A1 | 12/2022 | Gire et al. |
| 2023/0017064 A1 | 1/2023 | Tariyal et al. |
| 2023/0064804 A1 | 3/2023 | Tariyal et al. |

FOREIGN PATENT DOCUMENTS

| | | |
|---|---|---|
| DE | 20 2017 106 300 U1 | 11/2017 |
| EP | 0504301 B1 | 3/2014 |
| EP | 3187156 A1 | 7/2017 |
| ES | 1064610 U | 4/2007 |
| GB | 2364645 A | 6/2002 |
| IN | 6032/CHE/2015 | 5/2017 |
| JP | 2010-515520 A | 5/2010 |
| JP | 3177410 U | 8/2012 |
| KR | 30-0707596 S | 11/2013 |
| KR | 30-0914045 S | 7/2017 |
| KR | 30-0914047 S | 7/2017 |
| KR | 1020170120297 A | 10/2017 |
| KR | 101961471 | 3/2019 |
| KR | 20190026534 A | 3/2019 |
| KR | 102029068 B1 | 9/2019 |
| KR | 20190105743 A | 9/2019 |
| RU | 94033073 A1 | 7/1996 |
| RU | 2272604 C2 | 3/2006 |
| RU | 2479284 C2 | 4/2013 |
| RU | 129391 U1 | 6/2013 |
| RU | 2570279 C2 | 12/2015 |
| TW | 200924721 A | 6/2009 |
| WO | 2005087154 A2 | 9/2005 |
| WO | 2007/082341 A1 | 7/2007 |
| WO | 2011/013954 A2 | 2/2011 |
| WO | 2012/006670 A1 | 1/2012 |
| WO | 2013/108249 A1 | 7/2013 |
| WO | 2014/015975 A1 | 1/2014 |
| WO | 2015/041353 A1 | 3/2015 |
| WO | 2016025332 A1 | 2/2016 |
| WO | 2016/149317 A1 | 9/2016 |
| WO | 2017/015767 A1 | 2/2017 |
| WO | 2017031456 A1 | 2/2017 |
| WO | 2017/161378 A1 | 9/2017 |
| WO | 2017180909 A1 | 10/2017 |
| WO | 2020/079677 A1 | 4/2020 |
| WO | 2021087374 A1 | 5/2021 |
| WO | 2021087395 A1 | 5/2021 |
| WO | 2022010891 A1 | 1/2022 |
| WO | 2022140447 A1 | 6/2022 |

OTHER PUBLICATIONS

Patent Examination Report from New Zealand Application No. 740253 dated Feb. 9, 2023.
Office Action from U.S. Appl. No. 17/531,264 dated Mar. 30, 2023.
First Office Action from Taiwanese Patent Application No. 108109125 dated Mar. 27, 2023.
Office Action from Mexican Patent Application No. MX/a2018/002175 dated Apr. 13, 2023.
Notification of Reasons for Rejections from Japanese Patent Application No. 2020-573093 dated Apr. 24, 2023.
Notice of Preliminary Rejection from Korean Patent Application No. 10-2018-7007430 dated May 2, 2023.
Notice of Allowance from Canadian Patent Application No. 2,996,163 dated Jun. 20, 2023.
Office Action from Brazilian Patent Application No. BR112020018830-1 dated Apr. 6, 2023.
Office Action from Israel Patent Application No. 277232 dated Jun. 29, 2023.
Hearing Notice from Indian Patent Application No. 201817007398 dated Apr. 18, 2023.
Communication under Rule 71(3) EPC from European Application No. 16837928.7 dated May 9, 2023.

(56) References Cited

OTHER PUBLICATIONS

Notice of Allowance from Mexican Application No. MX/a2018/002175 dated Jul. 18, 2023.
Office Action issued in related Russian Patent Application No. 2020133900 dated Dec. 9, 2021, 22 pages.
Search Report issued in related Russian Patent Application No. 2020133900 dated Dec. 6, 2021, 3 pages.
Office Action issued in Canadian Patent Application No. 2,996,163 dated Sep. 23, 2022.
Examination Report issued in Indian Patent Application No. 202017044574 dated Jul. 19, 2022.
Decision to Grant issued in Russian Patent Application No. 2020133900 dated Aug. 12, 2022.
Office Action issued in European Patent Application No. 19768216.4 dated Nov. 8, 2022.
Written Opinion and International Search Report mailed Nov. 17, 2016 in corresponding International Application No. PCT/US2016/047859 (9 pages).
Huang et al.; "Efficacy and Safety of Tension-Free Vaginal Tape-Secur Mini-Sling Versus Standard Midurethral Slings for Female Stress Urinary Incontinence: A Systematic Review and Meta-Analysis"; International Neurourology Journal, 2015, 19(4): pp. 246-258 (13 pages).
Ellington et al.; "Outcomes of Surgery for Stress Urinary Incontinence in the Older Woman"; Clin Geriatr Med., Nov. 2015, 31(4): pp. 487-505 (21 pages).
Jones et al.; "Pessary Use In Pelvic Organ Prolapse and Urinary Incontinence"; Reviews in Obstetrics & Gynecology, vol. 3, No. 1; pp. 3-9 (7 pages).
Petros et al.; An Integral Theory and Its Method for the Diagnosis and Management of Female Urinary Scandinavian Journal of Urology and Nephrology: Suppl No. 153: 1993; pp. 1-93 (93 pages).
Coelho et al.: "Introduction of the method of intravaginal culture (IVC), through the device INVOCell routine laboratory RHA in Brazil"; JBRA Assisted Reproduction 2013; vol. 17 (No. 6): pp. 340-343 (4 pages); published Jan. 2013; doi: 10.5935/1518-0557.20130076.
Office Action from corresponding U.S. Appl. No. 15/242,105 dated May 17, 2018.
Office Action from corresponding U.S. Appl. No. 16/224,566 dated Oct. 7, 2020.
Examination Report from corresponding Australian Application No. 2016308363 dated Jun. 15, 2020.
Notice of Allowance from corresponding U.S. Appl. No. 15/242,105 dated Nov. 16, 2018.
Notice of Acceptance from corresponding Australian Application No. 2016308363 dated Aug. 17, 2020.
Notice of Grant from corresponding Chinese Application No. 2016800486873 dated May 6, 2020.
Decision to Grant from corresponding Russian Application No. 218109509 dated Mar. 25, 2020.
Official Notification Prior to Acceptance from corresponding Israeli Application No. 257627 dated Apr. 29, 2021.
Decision to Grant from Japanese Application No. 2018-528215 dated Mar. 23, 2021.
International Search Report and Written Opinion from International Patent Application No. PCT/US2021/033732 dated Oct. 21, 2021.
Office Action from corresponding EP Application No. 16837928.7 dated Jun. 14, 2021.
First Examination Report mailed Feb. 1, 2021, in corresponding Indian Patent Application No. 201817007398 (5 pages).
Office Action issued in related Japanese Patent Application No. 2018-528215 dated Jul. 27, 2020.
Office Action issued in related Russian Patent Application No. 2018109509 dated Dec. 5, 2019.
Search Report issued in related Russian Patent Application No. 2018109509 dated Dec. 5, 2019.
Office Action issued in related Chinese Patent Application No. 2016800486873 dated Aug. 27, 2019.
Extended European Search Report issued in counterpart European Patent Application No. 16837928.7 dated May 7, 2019.
International Search Report and Written Opinion issued in counterpart International Patent Application No. PCT/US2019/022624 dated Jun. 11, 2019.
Customer Review of Collapsible Silicone Cup for Sterilizing Your Diva Cup and Storing Menstrual Cups-Foldable for Travel (Amazon.com) Jan. 17, 2018, https://Www.amazon.com/review/RJ84O5XNN0ZY9/ref=cm_cr_srp_d_rdp_permie=UTF8&ASIN=B074PBX6ZY.
Nurse Hatty Kegel Exercise Weight System (Amazon.com) 2016 https://amazon/com/Nurse-Hatty-Exercise-Weight-System/dp/B01FQ21X16/ref=cm_cr_srp_d_product_top?ie=UTF8&th=1.
Shanna Atnip et al., "Vaginal Support Pessairies: Indications for Use and Fitting Strategies" Urologic Nursing, vol. 32, p. 121, table 4, steps 8-9, May-Jun. 2012.
Inomata Japanese Rice Washing Bowl with Side and Bottom Drainers, Clear (Amazon.com) 2016, http://www.amazon.com/Inomata-Japanese-Washington-Bottom-Drainers/dp/B004QZAAS2.
Office Action from corresponding U.S. Appl. No. 16/224,566 dated Feb. 19, 2021.
Notice of Allowance from corresponding U.S. Appl. No. 16/224,566 dated Jul. 27, 2021.
Notice of Allowance from corresponding U.S. Appl. No. 16/224,566 dated Nov. 5, 2021.
European Search Report from European Patent Application No. 19768216.4 dated Nov. 24, 2021, 8 pages.
Office Action from Mexican Patent Application No. MX/a/2020/009620 dated Feb. 6, 2024, 5 pages.
Non-final Rejection from U.S. Appl. No. 17/531,264 dated Feb. 1, 2024, 27 pages.
Notification to Grant Patent from Chinese Application No. 201980019605.6 dated Feb. 26, 2024, 4 pages.
Patent Examination Report 2 from New Zealand Patent Application No. 740253 dated Aug. 16, 2023, 3 pages.
Notice of Acceptance from New Zealand Patent Application No. 7402532 dated Dec. 5, 2023, 2 pages.
Notification of Second Office Action from Chinese Patent Application No. 201980019605.6 dated Sep. 29, 2023, 14 pages.
Notification of Reason for Rejection from Japanese Patent Application No. 2020-573093 dated Nov. 1, 2023, 13 pages.
Final Office Action from U.S. Appl. No. 17/531,264 dated Oct. 11, 2023, 30 pages.
Notice of Preliminary Rejection from Korean Patent Application No. 10-2020-7029289 dated Dec. 8, 2023, 10 pages.
Office Action from Canadian Patent Application No. 3,091,965 dated Oct. 31, 2023, 12 pages.
Communication under Rule 71(3) EPC from European Patent Application No. 19768216.4 dated Dec. 1, 2023, 7 pages.
Allowance Decision of Examination from Taiwan Patent Application No. 108109125 dated Dec. 18, 2023, 3 pages.
Examination Report No. 1 from Australian Patent Application No. 2019233913 dated Dec. 6, 2023, 4 pages.
Notice of Last Preliminary Rejection from Korean Patent Application No. 10-2018-7007430 dated Nov. 10, 2023, 4 pages.
Hearing Notice from Indian Patent Application No. 201817007398 dated Jul. 12, 2023, 2 pages.
Advisory Action from U.S. Appl. No. 17/531,264 dated Dec. 26, 2023, 7 pages.
Decision to Grant a Patent from Japanese Patent Application No. 2020-573093 dated Apr. 2, 2024.
Examination Report No. 2 from Australian Patent Application No. 2019233913 dated Mar. 28, 2024.
Extended European Search Report from European Patent Application No. 21807880.6 dated Apr. 24, 2024, 11 pages.
Office Action from Israeli Patent Application No. 277232 dated Jun. 3, 2024.
Notice of Allowance from Mexican Patent Application No. MX/a/2020/009620 dated Jun. 24, 2024.
Notice of Allowance from Korean Patent Application No. 10-2018-7007430 dated Jun. 25, 2024.

(56) References Cited

OTHER PUBLICATIONS

Extended European Search Report from EP Patent Application No. 24175756.6 dated Jul. 30, 2024.
Final Rejection from U.S. Appl. No. 17/531,264 dated Jul. 31, 2024
Office Action from JP Patent Application No. 2023-119948 dated Aug. 6, 2024.
Office Action from KR Patent Application No. 10-2020-7029289 dated Aug. 29, 2024.
Office Action from TW Patent Application No. 113110084 dated Sep. 2, 2024.

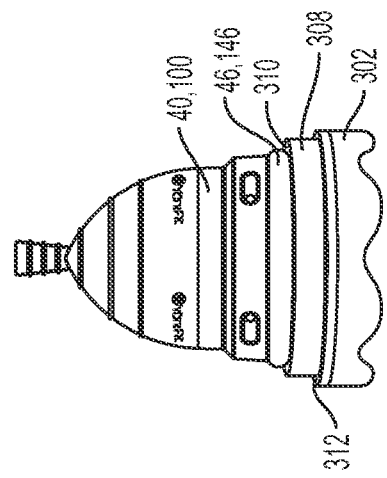
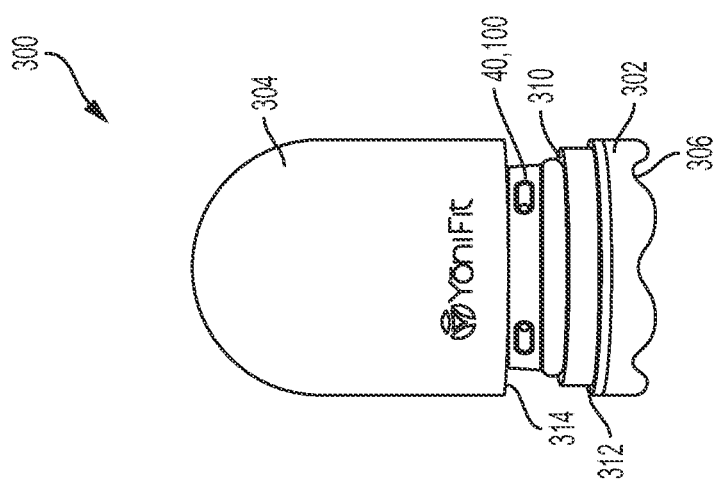
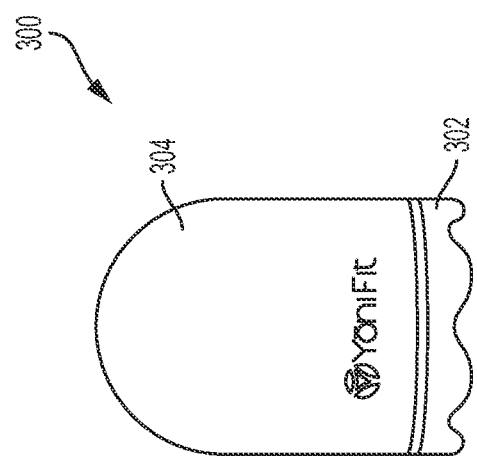

INTRAVAGINAL SUPPORT DEVICES AND METHODS

CROSS REFERENCE TO RELATED APPLICATIONS

This application is a continuation of U.S. application Ser. No. 16/355,638, filed Mar. 15, 2019, which claims priority benefit from U.S. Provisional Patent Application No. 62/644,340 filed on Mar. 16, 2018, U.S. Provisional Patent Application No. 62/687,119 filed on Jun. 19, 2018 and U.S. Provisional Patent Application No. 62/735,605 filed on Sep. 24, 2018, the entire contents of all of which are hereby incorporated by reference in their entireties.

TECHNICAL FIELD

The present disclosure relates in general to a vaginal insert device for use in improving and preventing symptoms associated with pelvic organ prolapse and urinary and/or fecal incontinence when the device is inserted.

BACKGROUND

Stress Urinary Incontinence (SUI) and Pelvic Organ Prolapse (POP) are growing problems globally that not only cost health care systems large amounts of money, but severely degrade the quality of life of tens of millions of women in the United States alone. Although surgical solutions may succeed in ameliorating symptoms associated with SUI and POP, surgery is not without risks and complications and may even leave the patient in a worse situation than before treatment. See Huang W, Wang T, Zong H, Zhang Y, *Efficacy and Safety of Tension Free Vaginal Tape-Secure Mini-Sling Versus Standard Midurethral Slings for Female Stress Urinary Incontinence: A Systematic Review and Meta-Analysis*, International Neurourology Journal, 2015, 19(4):246-58, which is incorporated herein by reference. See also Ellington D R, Erekson E A, Richter H E, *Outcomes of Surgery for Stress Urinary Incontinence in the Older Woman*, Clin Geriatr Med., 2015, 31(4):487-505, which is incorporated herein by reference. The FDA has issued several Public Health Notifications regarding surgical mesh placed through the vagina (transvaginal placement) to treat POP and SUI. The FDA identified serious and frequent complications with surgical mesh, including mesh erosion through the vagina, pain, infection, bleeding, discomfort during intercourse, organ perforation, urinary problems, recurrent prolapse, neuro-muscular problems, vaginal scarring/shrinkage & emotional problems. Most surgical complications require intervention including medical, additional surgical treatment and hospitalization.

Pessaries, which have been most commonly used for management of female POP but also have been used for SUI, present a viable non-surgical option for treating SUI and POP. Pessaries have had few complications and side effects. However, these devices are traditionally placed in the vagina for an extended period of time. They may also be uncomfortable. Furthermore, pessaries have been difficult for the patient to insert and remove. Insertion and removal of these devices has often required regular office visits with a physician for years. See, Jones K A, Harmanli O, *Pessary Use in Pelvic Organ Prolapse and Urinary Incontinence*, Rev Obstet Gynecol, 2010, 3(1):3-9, which is incorporated herein by reference. Difficulty with self-removal and insertion of the pessary, having the pessary fall out during defecation, and lack of comfort and convenience may be limiting widespread use of these devices.

SUI in women, is the involuntary leakage of urine due to a weakened pelvic support system and/or pressure on the bladder. This may be caused by aging, genetics, and/or childbirth. The Urology Care Foundation estimates that one of every three women will experience SUI at some point in their lifetime. There are a few types of urinary incontinence including stress incontinence, urge incontinence and mixed incontinence. All are mainly due to connective tissue laxity or damage in the vagina or supportive ligaments. See *An Integral Theory and Its Method for the Diagnosis and Management of Female Urinary Incontinence*, Petros P E, Ulmsten U I, Smayd J Urol Nephrol Suppl, 1993, 153, 1-93, which is incorporated by reference. FIG. 1 is a cross-section of the pelvic region of a female with normal anatomy illustrating the uterus 10, cervix 12, bladder 14, urethra 16, vagina 18, and rectum 20. FIG. 2 illustrates incontinence 22 (e.g., leakage of urine or fecal matter) caused by stress or pressure 24 on the bladder 14 or bowels. Involuntary leakage of urine or fecal matter often occurs during activities such as coughing, laughing, sneezing, lifting or exercise.

Connective tissue damage to three zones of the Integral System, which encompasses all three pelvic organs, including the bladder, vagina and ano-rectum, is the ultimate cause of Pelvic Organ Prolapse (POP) and dysfunction in these organs. FIG. 3 is a cross-section of the pelvic region of a female with a prolapsed bladder 26. FIG. 4 is a cross-section of the pelvic region of a female with a prolapsed back-passage or rectocele 28. FIG. 5 is a cross-section of the pelvic region of a female with a prolapsed uterus 30. POP is commonly due to child bearing but may also be caused simply by genetics and the aging process.

Therefore, there is a need for a pessary or other vaginal insert device that manages, improves, treats, prevents and/or eliminates female incontinence, POP or both incontinence and POP. There is a further need for such a pessary or other vaginal insert device that does not require a prescription, and is non-absorbent, over the counter, convenient, comfortable, and easy for a patient to insert and remove, with no or minimal physician intervention. Such a vaginal insert device may be reusable, but may also be disposable. There remains a need for intravaginal support devices and methods.

BRIEF SUMMARY

According to an embodiment, a vaginal insert device for improving, managing, treating, preventing, and/or eliminating symptoms associated with pelvic organ prolapse, urinary incontinence, fecal incontinence, or combinations thereof may include an upper portion having a cone-shaped body, the cone-shaped body having a base, an interior wall and an exterior wall; and a rib within the cone-shaped body, the rib configured to apply pressure to an organ wall to improve, manage, treat, prevent, and/or eliminate symptoms associated with pelvic organ prolapse, urinary incontinence, fecal incontinence, or combinations thereof.

According to an embodiment, the vaginal insert device may include a rim protruding from the exterior wall at an upper end of the upper portion. According to an embodiment, the rib extends downward within the cone-shaped body from adjacent the rim to the base, and wherein the rib and rim together apply pressure to the organ wall. According to an embodiment, the vaginal insert device may include one or more ridges protruding outwardly from the exterior wall. According to an embodiment, a stem extending downward from the base, the stem having one or more ridges protruding outwardly from an outer surface of the stem. According to an embodiment, the stem is conical, outwardly tapering, triangular, cross-shaped, substantially flat, or combinations thereof. According to an embodiment, the rib is configured to selectively or adjustably apply pressure to the organ wall based on an alignment of the rib with the organ wall. According to an embodiment, the rib includes a member extending radially inwardly from the interior wall of the cone-shaped body and longitudinally downward from a location near a top of the cone-shaped body. According to an embodiment, the member includes two or more members spaced equidistantly around a circumference of the interior wall of the cone-shaped body, the two or more members meeting at a center point of the cone-shaped body. According to an embodiment, the rib includes a member extending transversely to a longitudinal axis of the cone-shaped body. According to an embodiment, the member extends between diametrically opposing points on the interior wall, the member connected to the interior wall at the diametrically opposing points. According to an embodiment, the member extends longitudinally between a location near a top of the cone-shaped body and the base. According to an embodiment, in plan view, the rib is cross-shaped, "T" shaped "X" shaped, "Y" shaped, "K" Shaped, "V" shaped, star shaped, triangular, or pentagonal. According to an embodiment, the organ wall is one of a urethral sphincter, bladder neck, rectal wall, uterine wall, or combinations thereof. According to an embodiment, the rib and the cone-shaped body are formed integrally of the same material. According to an embodiment, the rib and the cone-shaped body are formed integrally of the same material. According to an embodiment, the rib and the cone-shaped body are formed integrally of the same material. According to an embodiment, the vaginal insert device is configured to support the organ wall during exercise. According to an embodiment, the vaginal insert device is configured to hold a fluid and secret the fluid in the vagina when the vaginal insert device is inserted into the vagina. According to an embodiment, the fluid is a medicine, hormone, or drug. According to an embodiment, the upper portion has an open upper end. According to an embodiment, the upper portion has a closed upper end.

According to an embodiment, a vaginal insert device for improving, managing, treating, preventing, and/or eliminating symptoms associated with pelvic organ prolapse, urinary incontinence, fecal incontinence, or combinations thereof, may include a cone-shaped body configured to apply pressure on an organ wall; and a stem configured to adjust the pressure applied to the organ wall. According to an embodiment, the vaginal insert device a member extending within an interior of the cone-shaped body, the member configured to apply the pressure to the organ wall. According to an embodiment, the stem is correlated with the member such that rotation of the stem is configured to adjust the pressure applied by the member to the organ wall. According to an embodiment, in a first position, the member is aligned with the organ wall and a first pressure is applied to the organ wall and in a second position, the member is not aligned with the organ wall and a second pressure is applied to the organ wall, the first pressure being greater than the second pressure. According to an embodiment, the member is a rib extending radially inwardly from an interior wall of the cone-shaped body and longitudinally downward from a location near a top of the cone-shaped body. According to an embodiment, the rib is cross-shaped in plan view and the stem is substantially flat and creates a plane, and wherein the cross-shape of the rib and the plane are aligned such that a position of the stem correlates to a position of the rib with respect to the organ wall. According to an embodiment, in plan view, the member is a cross-shaped rib having four ends, and wherein each of the four ends meets the interior wall of the cone-shaped body. According to an embodiment, the cone-shaped body is configured to apply an adjustable therapy force to the organ wall, the therapy force corresponding to a force configured to improve, manage, treat, prevent, and/or eliminate symptoms associated with pelvic organ prolapse, urinary incontinence, fecal incontinence, or combinations thereof. According to an embodiment, the organ wall is one of a urethral sphincter, bladder neck, rectal wall, uterine wall, or combinations thereof.

According to an embodiment, a vaginal insert device for improving, managing, treating, preventing, and/or eliminating symptoms associated with pelvic organ prolapse, urinary incontinence, fecal incontinence, or combinations thereof may include an upper portion having a cone-shaped body, the cone-shaped body having a base, an interior wall and an exterior wall; and a stem extending downward from the upper portion, the stem having a substantially flat shape. According to an embodiment, the stem may include a plurality of ridges extending from an outer surface of the stem. According to an embodiment, the plurality of ridges are uniformly spaced from a lower end of the stem. According to an embodiment, each of the plurality of ridges has the same thickness. According to an embodiment, each of the plurality of ridges extends around a perimeter of the stem. According to an embodiment, the stem is configured to adjust a pressure applied by the vaginal insert device on an organ wall. According to an embodiment, the stem and the upper portion are integrally formed of the same material. According to an embodiment, the stem is configured to be grasped by a user to insert, remove, or position, or combinations thereof, the vaginal insert device within the vagina. According to an embodiment, According to an embodiment, the stem is configured to allow positioning, rotation, or both of the vaginal insert device once the vaginal insert device is inserted into the vagina. According to an embodiment, the vaginal insert device may include a rib located within the cone-shaped body, the rib configured to apply pressure to an organ wall, wherein the rib and the stem are aligned such that rotation of the stem is configured to adjust the pressure applied by the rib on the organ wall.

According to an embodiment, a vaginal insert device may include a body having an open upper end, a wall, and a hollow interior within the wall; and a member within the hollow interior of the body, wherein the member is configured to apply pressure through the wall and onto an intravaginal wall, and wherein the pressure is configured to improve, manage, treat, prevent, and/or eliminate symptoms associated with pelvic organ prolapse, urinary incontinence, fecal incontinence, or combinations thereof. According to an embodiment, the wall has an internal diameter that gradually decreases from the open upper end to a base of the body. According to an embodiment, the member is connected to an interior side of the wall and extends from the open upper end to the base. According to an embodiment, the member is connected to an interior side of the wall adjacent to the open upper end. According to an embodiment, the member is connected to an interior side of the wall adjacent to the open upper end. According to an embodiment, the member is connected to an interior side of the wall adjacent to the open upper end. According to an embodiment, the member is not connected to the base. According to an embodiment, a second member, the second member extending between diametrically opposed sides of the wall, wherein the member and the second member are perpendicular such that a cross-shape is formed in plan view. According to an embodiment, the member extends between diametrically opposed sides of the wall. According to an embodiment, the body is a cone-shaped body having a decreasing diameter from the open upper end to the base.

According to an embodiment, a vaginal insert device may include an upper portion having a cone-shaped body and a longitudinal axis, the cone-shaped body having a base, an interior wall and an exterior wall; a member within the interior wall of the cone-shaped body, the member having a member plane aligned with the longitudinal axis; and a stem, the stem having a stem plane aligned with the longitudinal axis, wherein the member plane and the stem plane are aligned with one another. According to an embodiment, the member plane and the stem plane are arranged parallel or coplanar with one another. According to an embodiment, the member plane and the stem plane are arranged perpendicular or angled with one another. According to an embodiment, the vaginal insert device may include a rim protruding from the exterior wall at an upper end of the upper portion. According to an embodiment, the member extends downward within the cone-shaped body from adjacent the rim to the base, and wherein the member and rim together apply pressure to the organ wall. According to an embodiment, the vaginal insert device may include one or more ridges protruding outwardly from the exterior wall. According to an embodiment, the stem comprises one or more ridges protruding outwardly from an outer surface of the stem. According to an embodiment, the stem is two-dimensional or flat. According to an embodiment, the stem is rectangular. According to an embodiment, the member extends radially inwardly from the interior wall of the cone-shaped body and longitudinally downward from a location near a top of the cone-shaped body. According to an embodiment, the member includes two or more members spaced equidistantly around a circumference of the interior wall of the cone-shaped body, the two or more members meeting at a center point of the cone-shaped body. According to an embodiment, the member includes a member extending transversely to a longitudinal axis of the cone-shaped body. According to an embodiment, the member extends between diametrically opposing points on the interior wall, the member connected to the interior wall at the diametrically opposing points. According to an embodiment, in plan view, the member is cross-shaped, "T" shaped "X" shaped, "Y" shaped, "K" Shaped, "V" shaped, star shaped, triangular, or pentagonal. According to an embodiment, the member is configured to apply pressure to an organ wall, and wherein the organ wall is one of a urethral sphincter, bladder neck, rectal wall, uterine wall, or combinations thereof. According to an embodiment, the device is configured for improving, managing, treating, preventing, and/or eliminating symptoms associated with pelvic organ prolapse, urinary incontinence, fecal incontinence, or combinations thereof. According to an embodiment, the member is configured to apply pressure to an organ wall for improving, managing, treating, preventing, and/or eliminating symptoms associated with pelvic organ prolapse, urinary incontinence, fecal incontinence, or combinations thereof. According to an embodiment, the member and the cone-shaped body are formed integrally of the same material. According to an embodiment, in plan view, the member is a cross-shaped rib having four ends, and wherein each of the four ends meets the interior wall of the cone-shaped body. According to an embodiment, the member is a rib. According to an embodiment, the vaginal insert device may include a rib located within the cone-shaped body, the rib configured to apply pressure to an organ wall, wherein the rib and the stem are aligned such that rotation of the stem is configured to adjust the pressure applied by the rib on the organ wall.

According to an embodiment, a method for improving, managing, treating, preventing, and/or eliminating symptoms associated with pelvic organ prolapse, urinary incontinence, fecal incontinence, or combinations thereof may include inserting a vaginal insert device into a vagina, the vaginal insert device having a cone-shaped body with a rib extending within an inner portion of the cone-shaped body; aligning the vaginal insert device with an organ wall; and adjusting a pressure applied to the organ wall by rotating the vaginal insert device. According to an embodiment, the method may include applying pressure to the organ wall by aligning the rib with the organ wall. According to an embodiment, adjusting the pressure applied to the organ wall comprises reducing the pressure by rotating the rib out of alignment with the organ wall. According to an embodiment, adjusting the pressure applied to the organ wall comprises increasing the pressure by rotating the rib into alignment with the organ wall. According to an embodiment, the vaginal insert device further comprises a stem extending downward from the cone-shaped body, and wherein rotating the vaginal insert device comprises rotating the stem while the vaginal insert device is inserted into the vagina. According to an embodiment, adjusting the pressure applied to the organ wall is performed prior to or after exercising. According to an embodiment, the method may include increasing the pressure applied to the organ wall prior to exercising and decreasing the pressure applied to the organ wall after exercising. According to an embodiment, increasing the pressure applied the organ wall is performed by rotating the vaginal insert device such that the rib is aligned with the organ wall, and wherein decreasing the pressure applied to the organ wall is performed by rotating the vaginal insert device such that the rib is not aligned with the organ wall. According to an embodiment, inserting the vaginal insert device includes: compressing the vaginal insert device from an original configuration to a compact configuration having a shape configured to enter into the vagina; releasing the vaginal insert device once inserted into the vagina; and allowing the vaginal insert device to expand from the compact configuration to the original configuration, wherein the vaginal insert device applies pressure to the organ wall due to an exterior side of the vaginal insert device, the rib, and/or one or more ridges protruding from the exterior side of the vaginal insert device. According to an embodiment, the method may include a rim configured to apply pressure to the organ wall with the rib. According to an embodiment, the method may include removing the vaginal insert device by grasping the stem and pulling the vaginal insert device out of the vagina. According to an embodiment, the method may include impregnating the vaginal insert device with a fluid, and secreting the fluid into the vagina when the vaginal insert device is inserted, wherein the fluid is a drug, medication, or hormone. According to an embodiment, the method may include collecting a sample of a vaginal discharge to perform a diagnostic on the sample. According to an embodiment, the diagnostic is performed while the vaginal insert device is in the vagina. According to an embodiment, the sample is collected by the user or a clinician after the vaginal insert device is removed and the diagnostic is performed by the user or clinician. According to an embodiment, the vaginal insert device is a vaginal insert device according to any one of the embodiments described herein.

According to an embodiment, a method for use of a vaginal insert device may include providing a vaginal insert device according to any of the embodiments described herein, inserting the vaginal insert device into a vagina; and applying pressure to an organ wall with the vaginal insert device. According to an embodiment, the method may include adjusting the pressure applied to the organ wall. According to an embodiment, the vaginal insert device improves, manages, treats, prevents, and/or eliminates symptoms associated with pelvic organ prolapse, urinary incontinence, fecal incontinence, or combinations thereof, during activity, high intensity activity, sedentary activity, coughing, laughing, sneezing, lifting and/or exercise. According to an embodiment, the method may include inserting the vaginal insert device prior to cardiovascular activity. According to an embodiment, pressure is applied to the organ wall with an exterior side of the vaginal insert device, features protruding from an interior side of the vaginal insert device, or features protruding from the exterior side of the vaginal insert device. According to an embodiment, the features are one or more ribs, one or more rims, one or more ridges, or combinations thereof. According to an embodiment, the method may include adjusting the pressure applied to the organ wall by reducing the pressure by rotating the one or more ribs out of alignment with the organ wall and by increasing the pressure by rotating the one or more ribs into alignment with the organ wall. According to an embodiment, adjusting the pressure applied to the organ wall is performed prior to or after exercising. According to an embodiment, inserting the vaginal insert device includes: compressing the vaginal insert device from an original configuration to a compact configuration having a shape configured to enter into the vagina; releasing the vaginal insert device once inserted into the vagina; and allowing the vaginal insert device to expand from the compact configuration to the original configuration, wherein the vaginal insert device applies pressure to the organ wall due to an exterior side of the vaginal insert device, the one or more ribs, and/or one or more ridges protruding from the exterior side of the vaginal insert device. According to an embodiment, the method may include a rim configured to apply pressure with the one or more ribs. According to an embodiment, the method may include removing the vaginal insert device by grasping the stem and pulling the vaginal insert device out of the vagina. According to an embodiment, the method may include impregnating the vaginal insert device with a fluid, and secreting the fluid into the vagina when the vaginal insert device is inserted, wherein the fluid is a drug, medication, or hormone. According to an embodiment, the method may include collecting a sample of a vaginal discharge to perform a diagnostic on the sample. According to an embodiment, the diagnostic is performed while the vaginal insert device is in the vagina. According to an embodiment, the sample is collected by the user or a clinician after the vaginal insert device is removed and the diagnostic is performed by the user or clinician.

According to an embodiment, a case for a vaginal insert device may include a base configured to hold the vaginal insert device; and a cover configured to interact with the base and enclose the vaginal insert device. According to an embodiment, the base includes a plurality of openings in a bottom surface, the openings configured to release water or liquid from above the bottom surface to below the bottom surface. According to an embodiment, the base is configured to operate as a drying rack for the vaginal insert device. According to an embodiment, the base includes a plurality of protrusions extending upward from a bottom surface, the plurality of protrusions configured to retain the vaginal insert device on the base. According to an embodiment, the base includes one or more grooves configured to interact with one or more protrusions on the cover, the cover having a first position where the one or more protrusions are engaged in a respective one of the one or more grooves locking the cover to the base and a second position where the one or more protrusions are disengaged from the respective one of the one or more grooves such that the cover is unlocked form the base. According to an embodiment, the case may include one or more latches for retaining the vaginal insert device on the base. According to an embodiment the vaginal insert device may be according to any of the embodiments described herein.

According to an embodiment, a kit for improving, managing, treating, preventing, and/or eliminating symptoms associated with pelvic organ prolapse, urinary incontinence, fecal incontinence, or combinations thereof may include a first vaginal insert device, the first vaginal insert device having a first outer diameter; and a second vaginal insert device, the first vaginal insert device having a second outer diameter, wherein the first outer diameter is different than the second outer diameter. According to an embodiment, the first vaginal insert device and the second vaginal insert device are selected to accommodate a changing condition of a user's vagina. According to an embodiment, the kit may include a third vaginal insert device having a third outer diameter, the third outer diameter different than the first outer diameter and the second outer diameter. According to an embodiment, the first vaginal insert device, the second vaginal insert device, and/or the third vaginal insert device may be a vaginal insert device according to any of the embodiments described herein.

It is to be understood that both the foregoing general description and the following detailed description are examples and explanatory and are not restrictive on the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIGS. 22A-22K illustrate perspective views of a carrying case for a vaginal insert device and a brush, in accordance with embodiments of the present disclosure;

DETAILED DESCRIPTION

Figure 1:
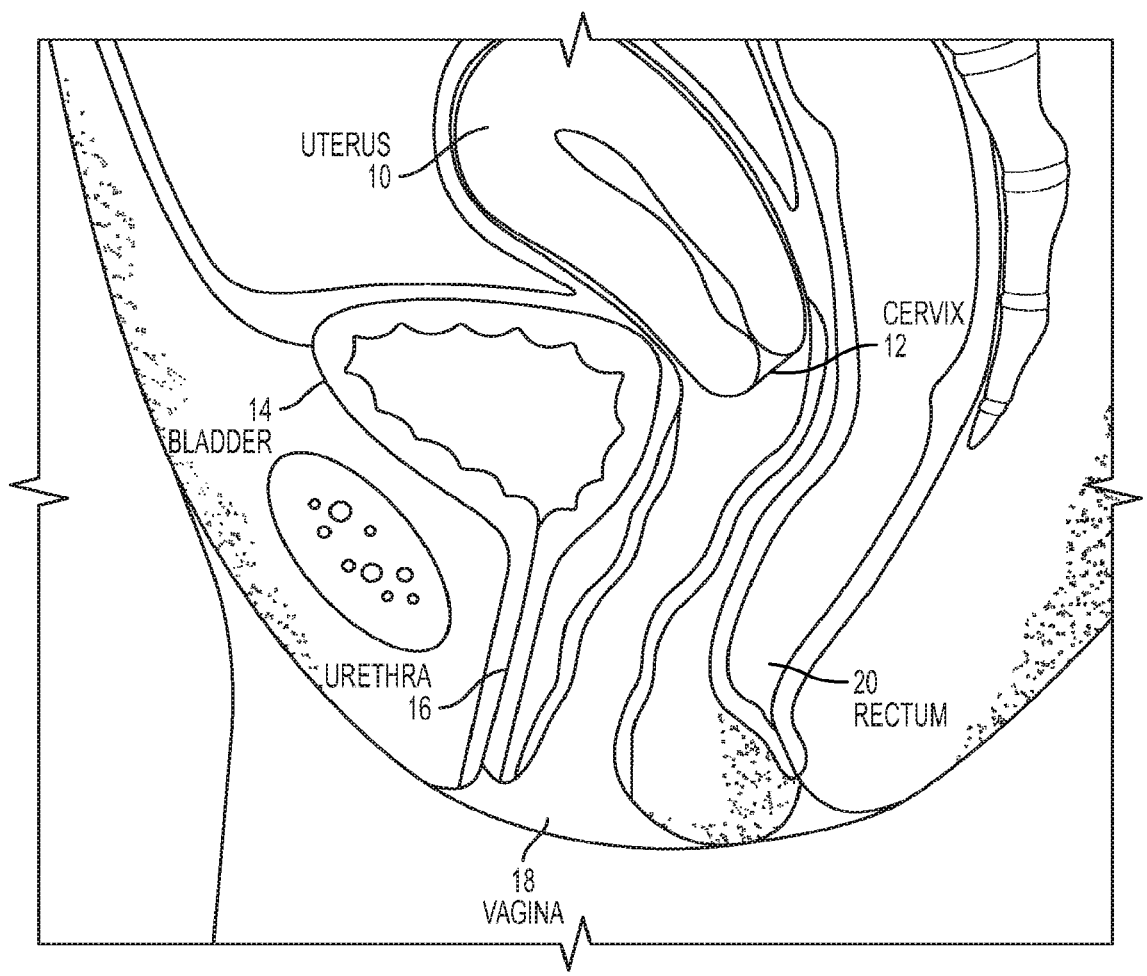
FIGS. 1-5 each illustrate a cross-section of the pelvic region of a female for purposes of discussing the background of the present disclosure.
Figure 2:
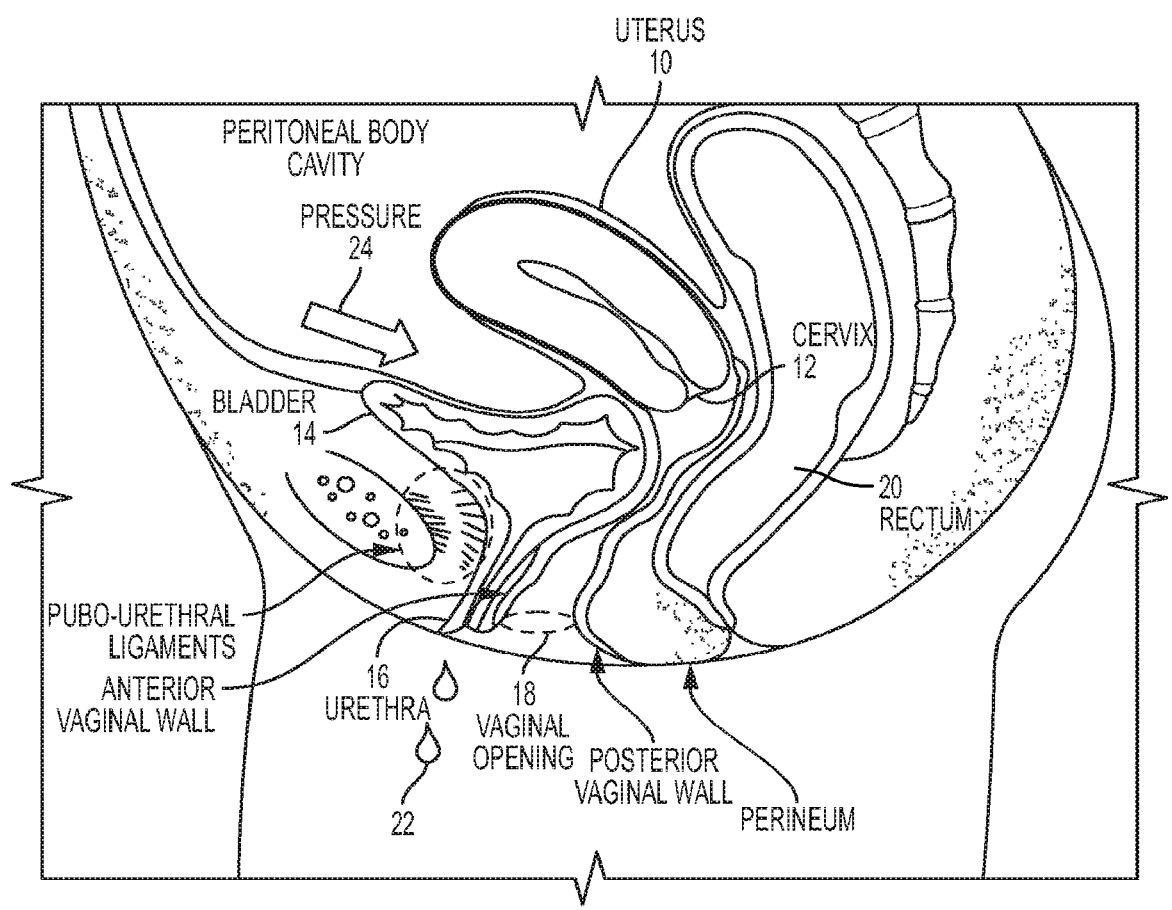
Figure 3:
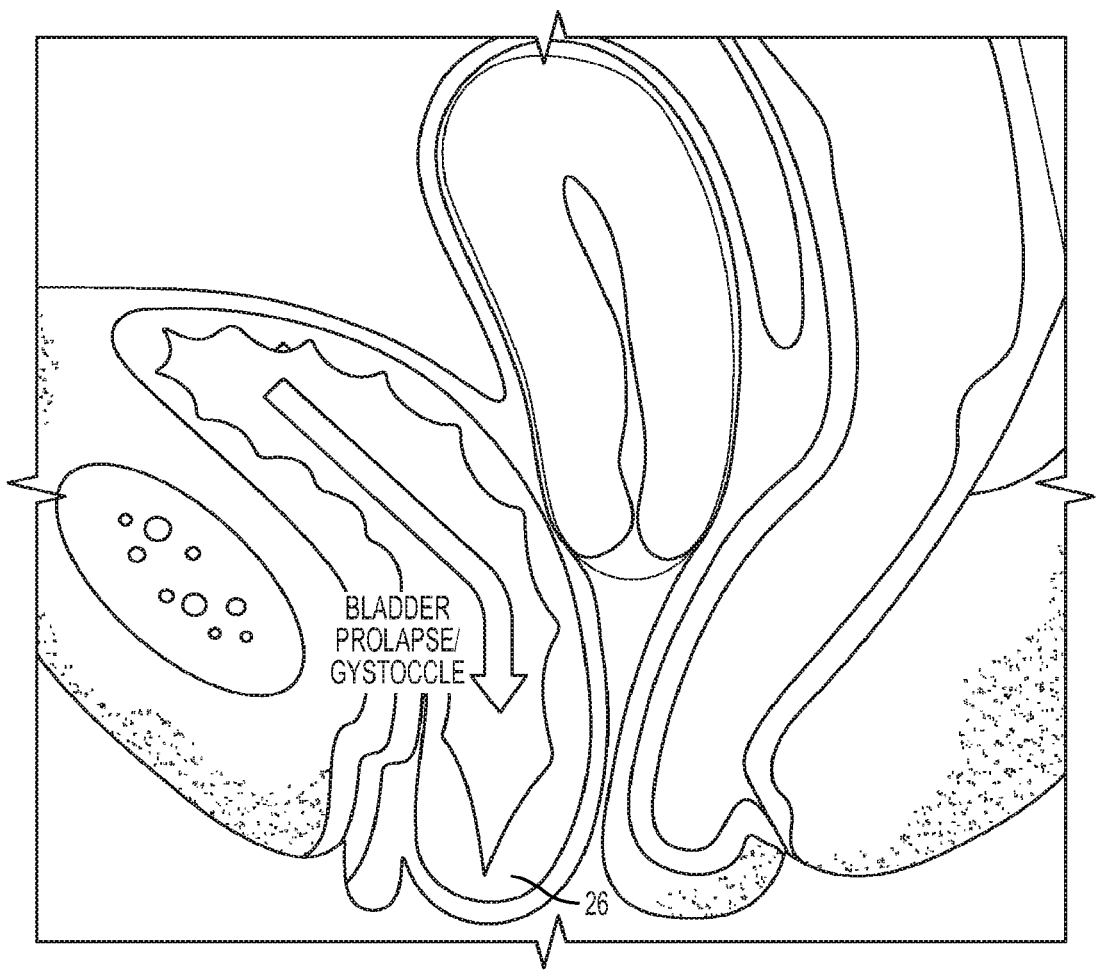
Figure 4:
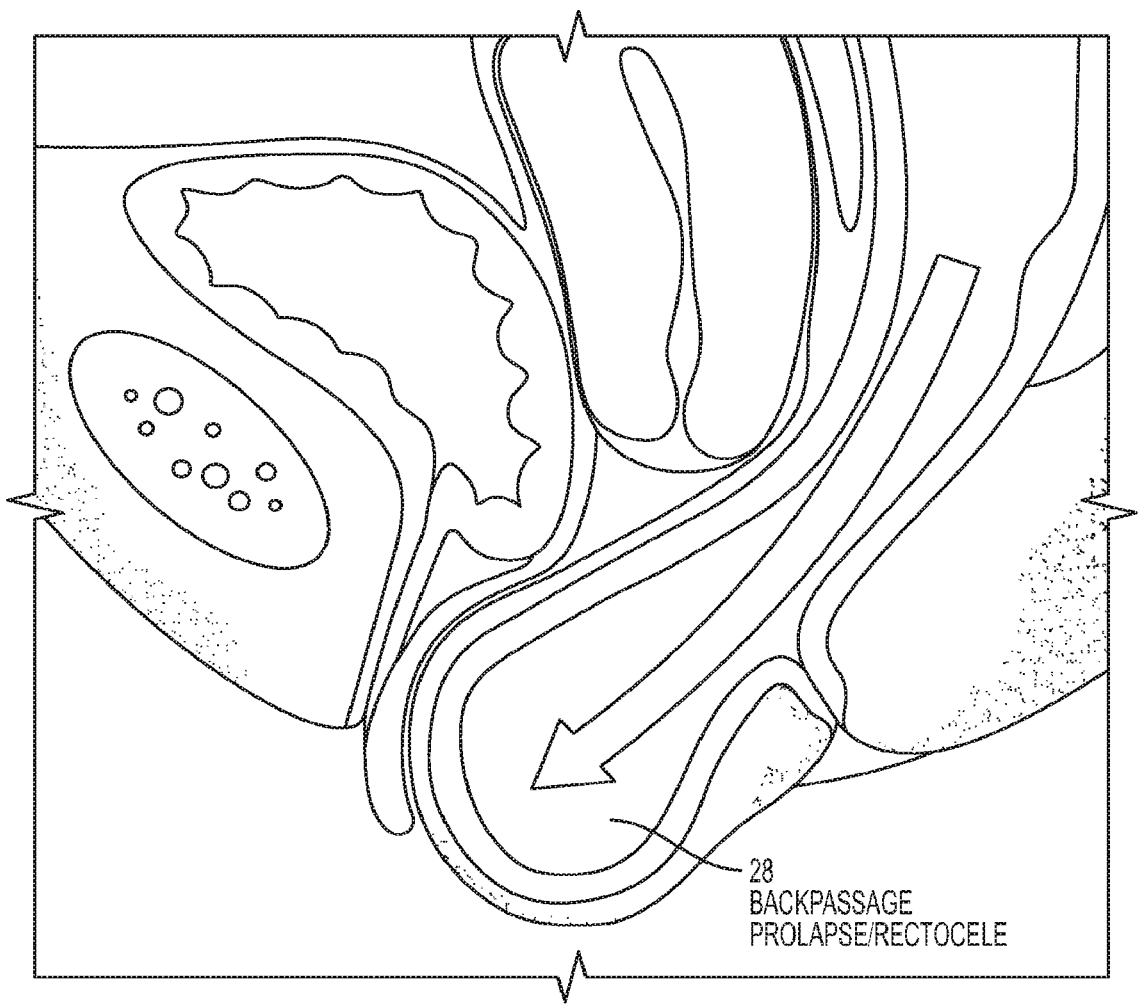
Figure 5:
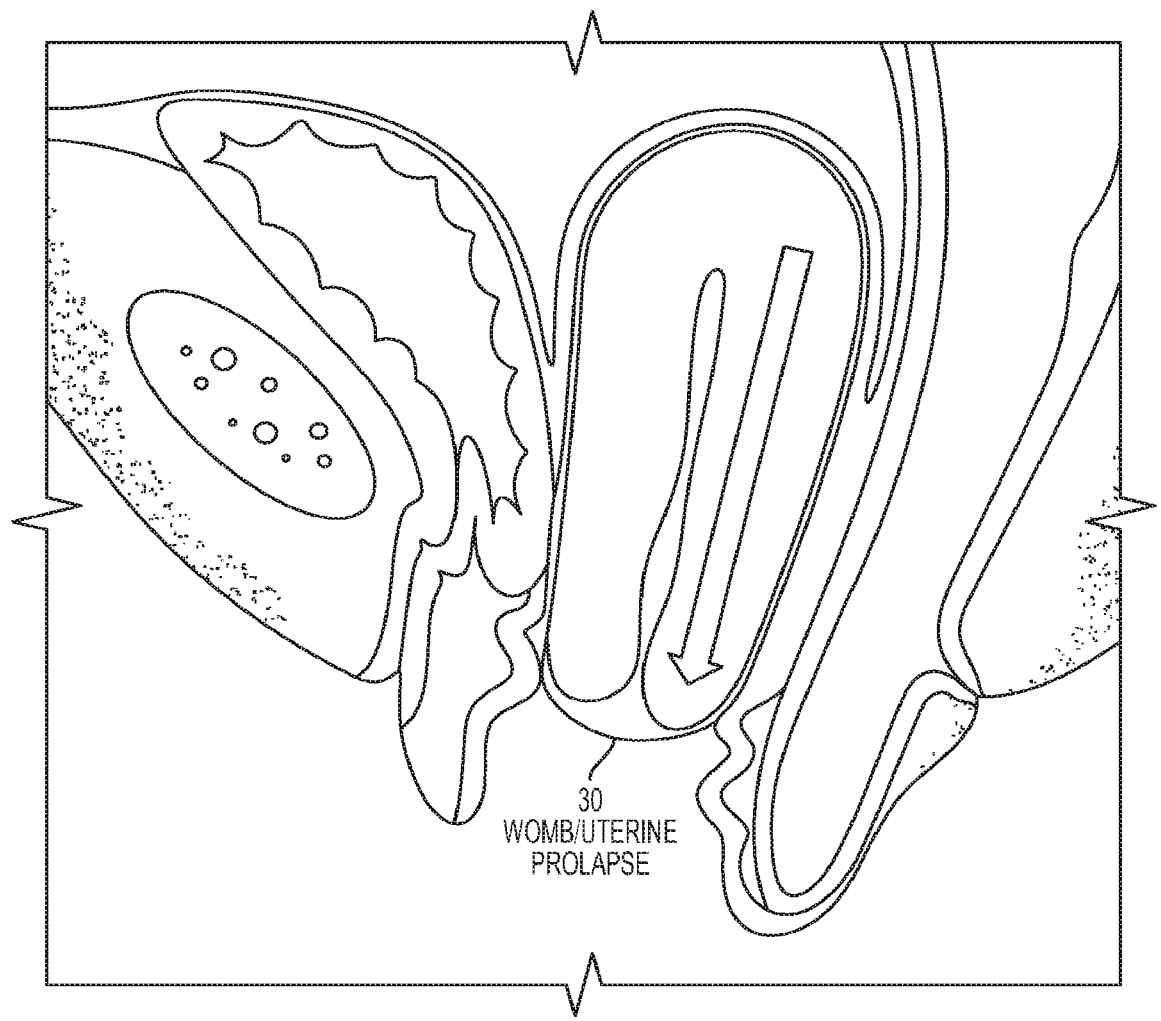

Certain embodiments and their advantages are best understood by reference to FIGS. 6A through 38, wherein like numbers are used to indicate like and corresponding parts or sections. A vaginal insert device as described in U.S. application Ser. No. 15/242,105, now U.S. Pat. No. 10,188,545, the contents of which are hereby incorporated by reference, may also be contemplated. Although, the device is described and depicted as being inserted into the vagina to reduce or eliminate, for example, urinary incontinence, the device of the present disclosure may also be used to treat fecal incontinence and/or the involuntary leakage of fecal matter, as will be described in more detail. Additional uses are also contemplated, such as, for example, menstrual uses, collection of vaginal fluids or discharge, diagnostics, exercising or strengthening muscles, secreting medicines or hormones, monitoring of the vagina or other organs or body parts, etc., or combinations thereof.

The vaginal insert device of the present disclosure may manage, improve, prevent, treat, and/or eliminate female incontinence, including urinary incontinence, fecal incontinence, POP, or POP and urinary and/or fecal incontinence, and combinations thereof. The vaginal insert device may not require a prescription (although may for drug or hormone delivery or as an indicator for diagnostic assistance). The vaginal insert device may be non-implantable (though could be implantable), non-absorbent, over the counter, convenient, flexible, comfortable, and easy for a patient to insert and remove, with no or minimal physician intervention. In some instances, such a vaginal insert device may be reusable. Alternatively or additionally, the vaginal insert device may be disposable. The vaginal insert device may eliminate concern of Toxic Shock Syndrome (TSS) by not consisting of an absorbency element which could breed bacteria, cause infection, and/or produce odor.

In certain instances, the device of the present disclosure is fabricated, such as by a molding process (e.g., liquid injection molding), with a material. The material may be an elastic and non-absorbent material, for example, a biocompatible elastomer such as medical grade silicone. The material may be a medical grade material, such as, for example a medical grade silicone. The material may be 100% medical grade silicone. Examples of silicone material suitable for use in the present device may be NuSil Technology's MED-4950 product, which is characterized as a liquid silicone rubber, Momentive LIM 6030, or Momentive LIM 6040. Alternative materials and methods of forming are contemplated. For example, the vaginal insert device may be formed of cotton, such as 100% cotton, may be any plastic, thermoplastic, polymer, elastomer. The material may have sufficient structure to apply pressure to a vaginal wall but may be flexible enough to allow for folding or compression during insertion and removal. The vaginal insert device may be compression molded, extruded, 3-d printed, rotationally molding, machined, caste, etc.

The vaginal insert device of the present disclosure may be shaped so that the device is held securely in place in the vagina when inserted, as well as shaped to impose pressure on the intravaginal wall for therapy force and/or to support pelvic organs and/or prevent further pelvic organ displacement. In an example, the vaginal insert device of the present disclosure is for management of stress urinary incontinence (e.g., the involuntary leakage of urine) during activities such as coughing, laughing, sneezing, lifting and exercise for patients over the age of eighteen. The device may be inserted by an adult woman for up to about eight to twelve hours at a time before removal and reinsertion, depending on their comfort level. The device may be implantable and remain in the body for longer periods of time.

Figure 6A:
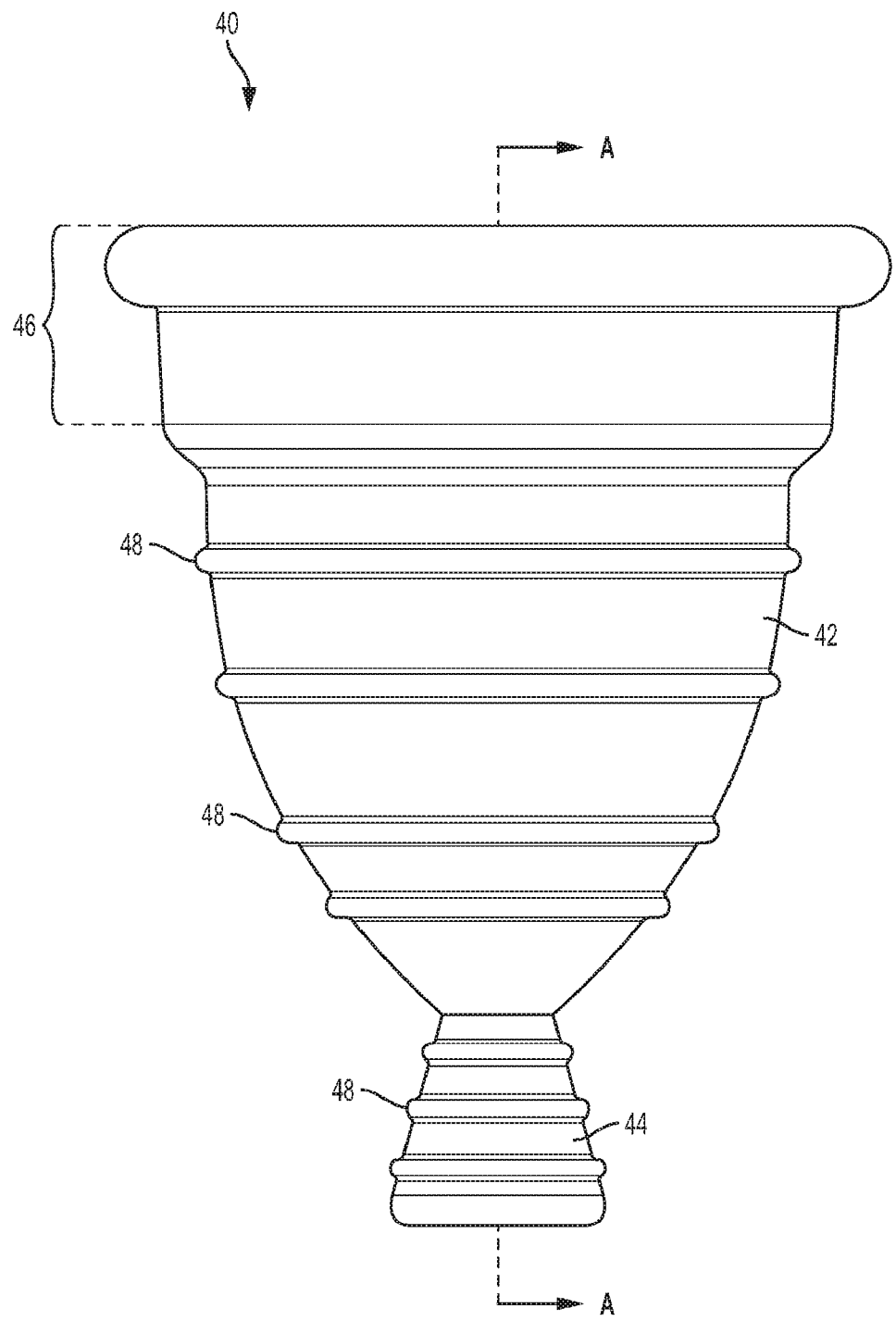
FIG. 6A illustrates a side view of an example vaginal insert device, in accordance with embodiments of the present disclosure.

FIG. 6A illustrates a side view of an exemplary vaginal insert device 40, in accordance with embodiments of the present disclosure. The vaginal insert device 40 of FIG. 6A may include an upper portion 42 and a lower stem-like, removal portion or stem 44. The upper portion 42 may be cone-shaped. That is, the upper portion 42 may have a first diameter which decreases to a second diameter. The decreasing in diameter may be gradual. The cone-shaped body of the upper portion 42 may thus include a changing diameter. Although described herein as cone-shaped, other shapes of the upper portion 42 are contemplated. Such other shapes may include changing diameters such that a first diameter is configured to apply pressure to an intravaginal or organ wall and a second diameter is configured to be smaller than the first diameter and not interact with an intravaginal wall. Such shapes may include trapezoid, spheres, cylinders, cubes, pyramids, hexagonal prisms, etc.

As further illustrated and described in more detail below, the upper portion 42 may include a rim 46 that protrudes from the upper portion as well as ridges 48 that may be spaced apart from the top of the upper portion 42 to the lower end or base of the upper portion 42. In an embodiment, the rim 46 may be omitted and may not be present. Ridges 48 may be randomly or uniformly spaced. The removal portion may also have ridges 48, which like the upper portion may be spaced apart from the top of the stem 44 to the lower end of the stem 44. Ridges 48 may also be semi-permeable to allow liquid, gas, lubrication, and/or medication to pass through. The ridges 48 on the stem 44 may be randomly or uniformly placed.

Figure 6B:
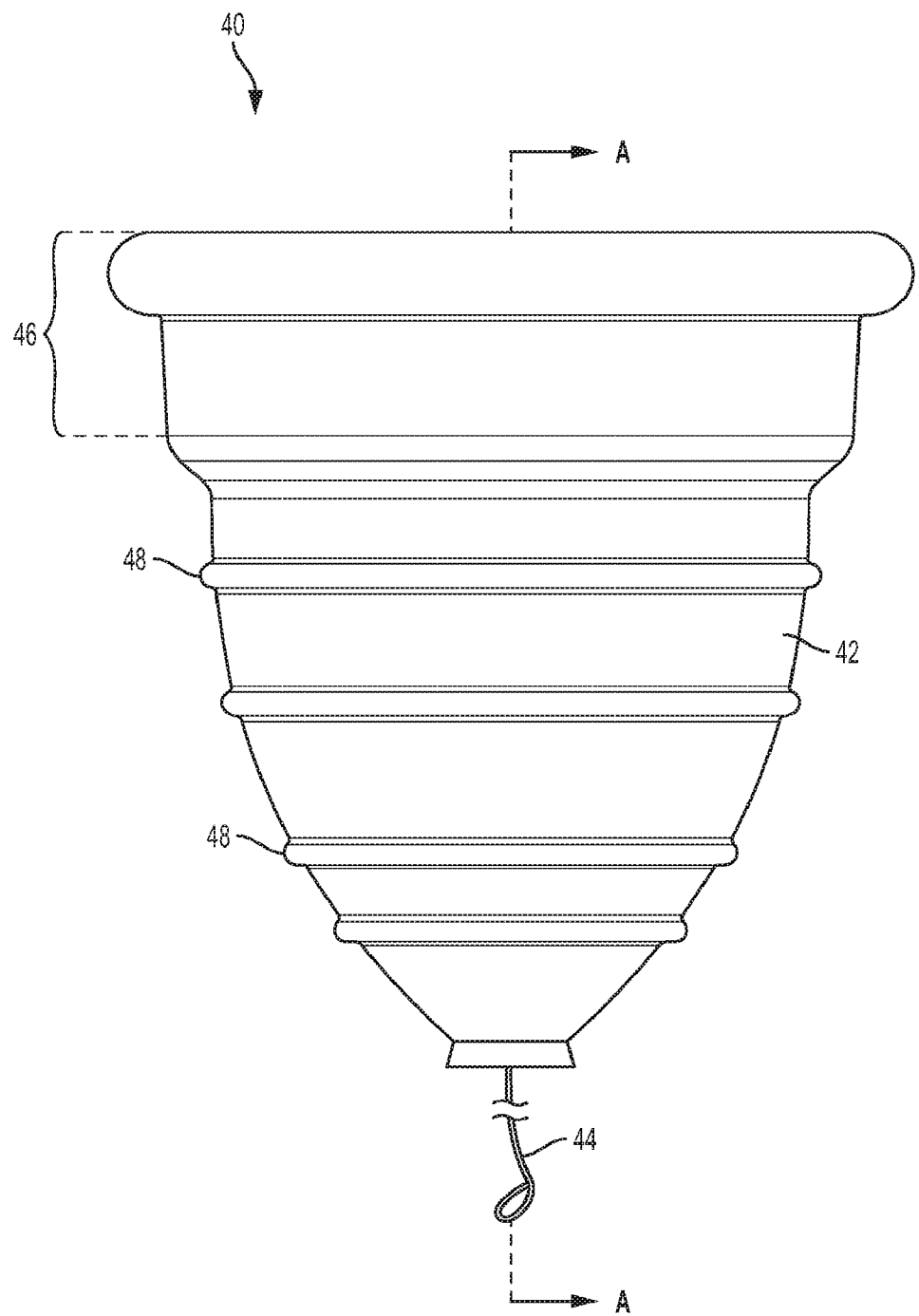
FIG. 6B illustrates a side view of another example vaginal insert device, in accordance with embodiments of the present disclosure.

FIG. 6B illustrates a side view of another exemplary vaginal insert device 40, in accordance with embodiments of the present disclosure. In this embodiment, device 40 is t similar to the device of FIG. 6A except the stem 44 may be a string, cord, or ribbon (collectively referred to as a string), such as is used in a tampon. The string may assist in insertion and/or removal of the vaginal insert device 40 from the vagina.

Figure 7:
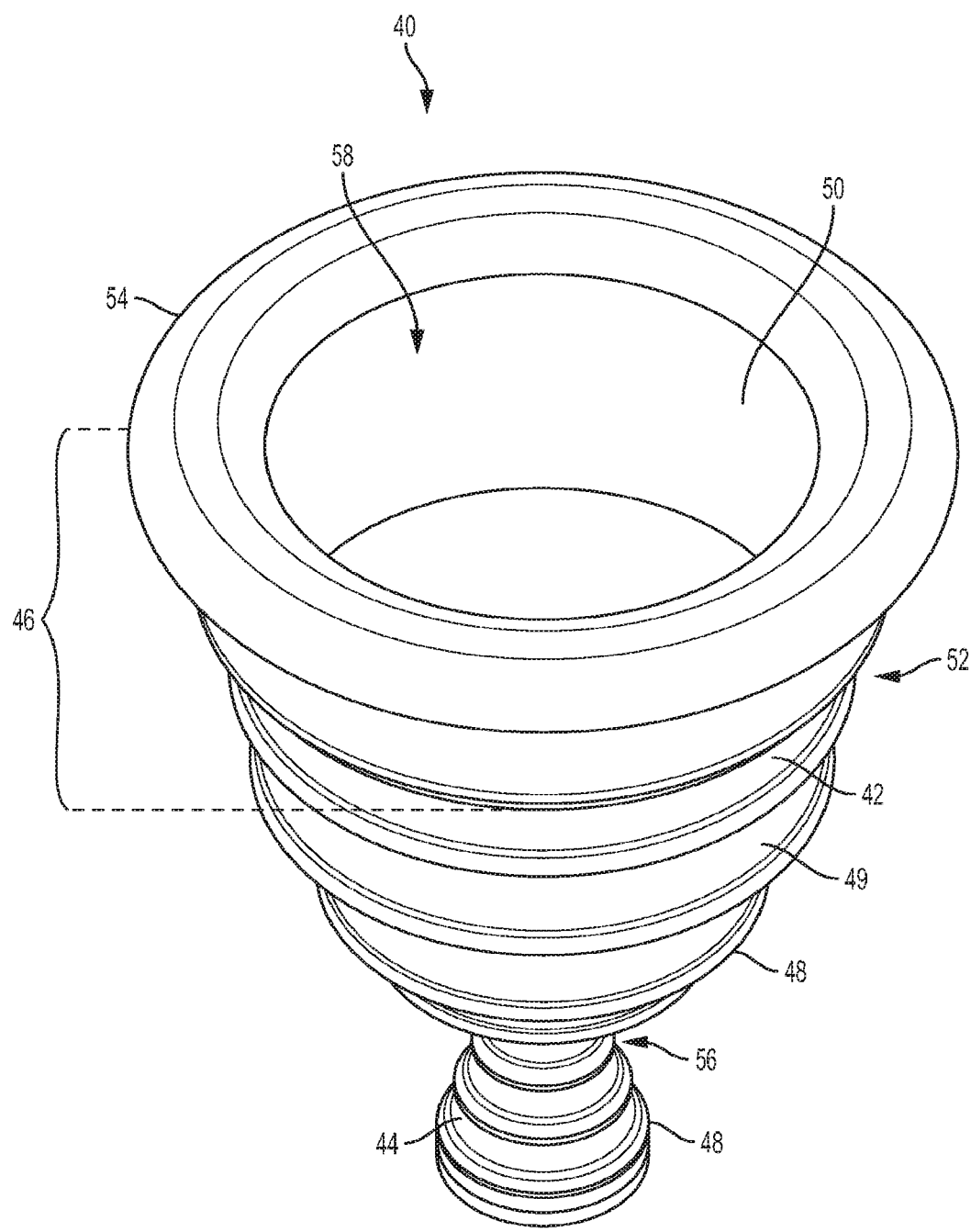
FIG. 7 illustrates a perspective view of the vaginal insert device of FIG. 6A.
Figure 9:
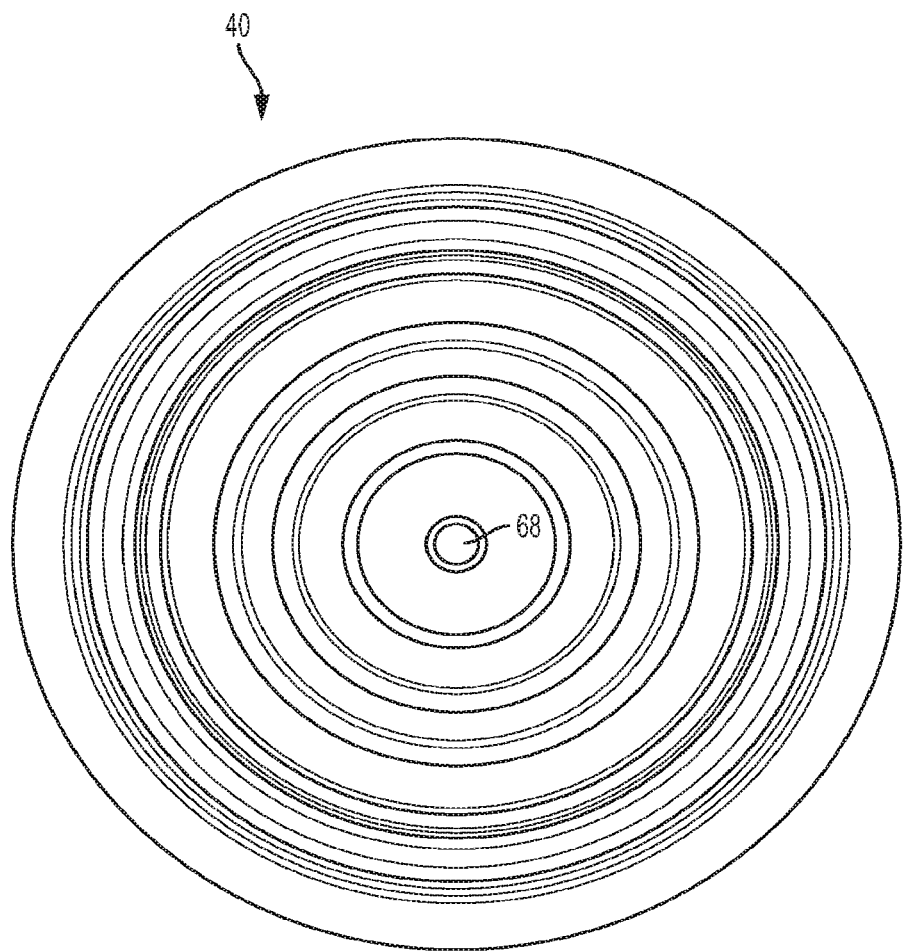
FIG. 9 is a bottom view of the vaginal insert device of FIG. 6A.
Figure 10:
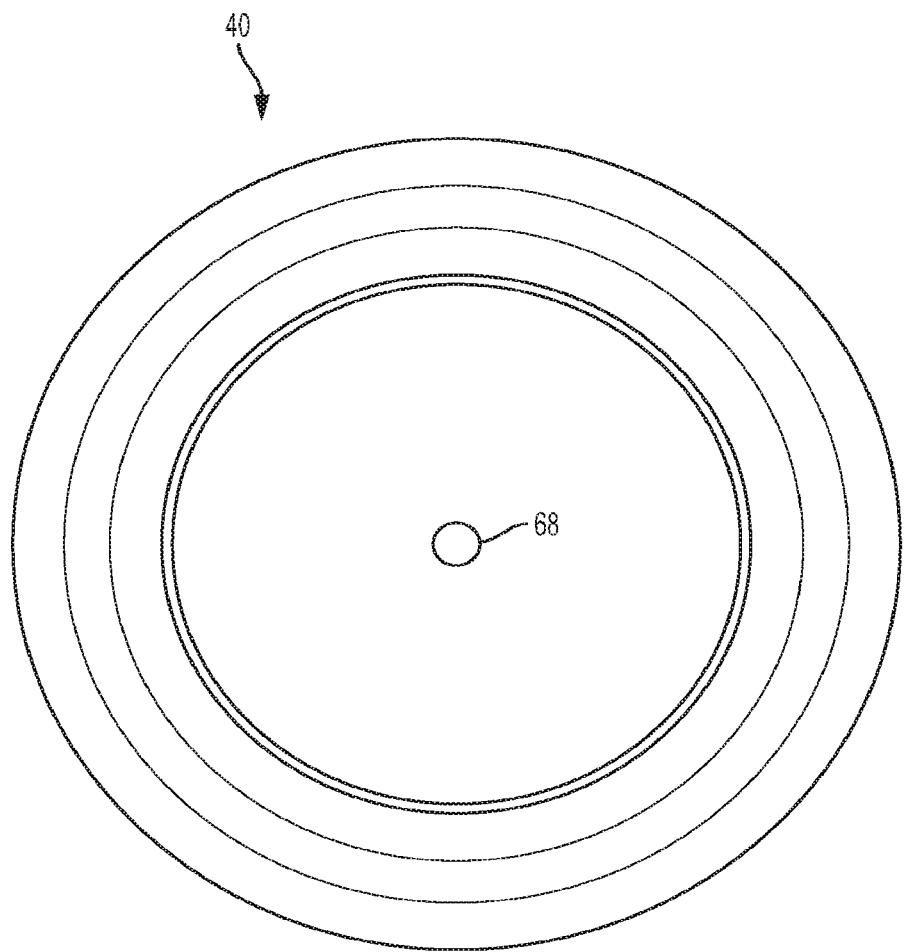
FIG. 10 is a top view of the vaginal insert device of FIG. 6A.

FIG. 7 illustrates a perspective view of the vaginal insert device 40 of FIG. 6A. As shown in FIG. 7, the upper portion 42 has a cone-shaped body. The upper portion 42 may have a circular transverse cross-section throughout its length (for example, as shown in FIGS. 9 and 10). The circular transverse cross-section may reduce in diameter from an upper end, such as upper open end 54, to a base or lower end 56. The reduction in diameter may be a reduction in internal diameter of the upper portion 42, a reduction in the external diameter of the upper portion 42, or a combination thereof. The circumference of the upper portion 42 may decrease from the upper open end 54 to the lower end 56. The upper portion 42 may have a wall 49 having an interior wall or interior side 50 and an exterior wall or exterior side 52. The upper portion 42 may include the upper open end 54, the lower end 56, and a hollow interior 58. The upper open end 54 may expose the hollow interior 58 to atmospheric pressure (when not inserted) and to the interior of the vagina (when inserted).

With continued reference to FIG. 7, the rim 46 may be circular and may surround and protrude from the exterior side 52 of the wall 49. The rim 46 may be adjacent to the upper open end 54. Ridges 48 may be circular rings that surround the exterior side 52 of wall 49. The stem 44 may extend from the lower end 56 of the upper portion 42. The upper portion 42 and the stem 44 may be fabricated as an integral, one-piece device formed of a single material. For example, the upper portion 42 and the stem 44 may be formed of a medical grade silicone. The upper portion 42 and stem 44 may be injection molded as a single, integral device of a medical grade silicone. Alternatively, the upper portion 42 and the stem 44 may be made from more than one part and/or more than one material that may attach and/or detach or expand and retract for therapy, treatment, or sterilization purposes. The upper portion 42 and stem 44 may be permanently or detachably coupled together. The stem 44 may have a cone-shaped body. The cone-shape may be a shape that increases in diameter from the lower end 56 to the distal end of the stem 44. That is, the cone-shaped body of the stem 44 may expand radially outward from the lower end 56 to the lower open end 64 (FIG. 8) of the stem 44. The cone-shaped body of the upper portion 42 may expand radially outward from the lower end 56 to the open upper end 54. Thus, the stem 44 and the upper portion 42 may expand radially outward in opposing axial directions. The circumferences and/or diameters of the stem 44 and upper portion 42 may increase gradually in opposing directions.

Figure 8:
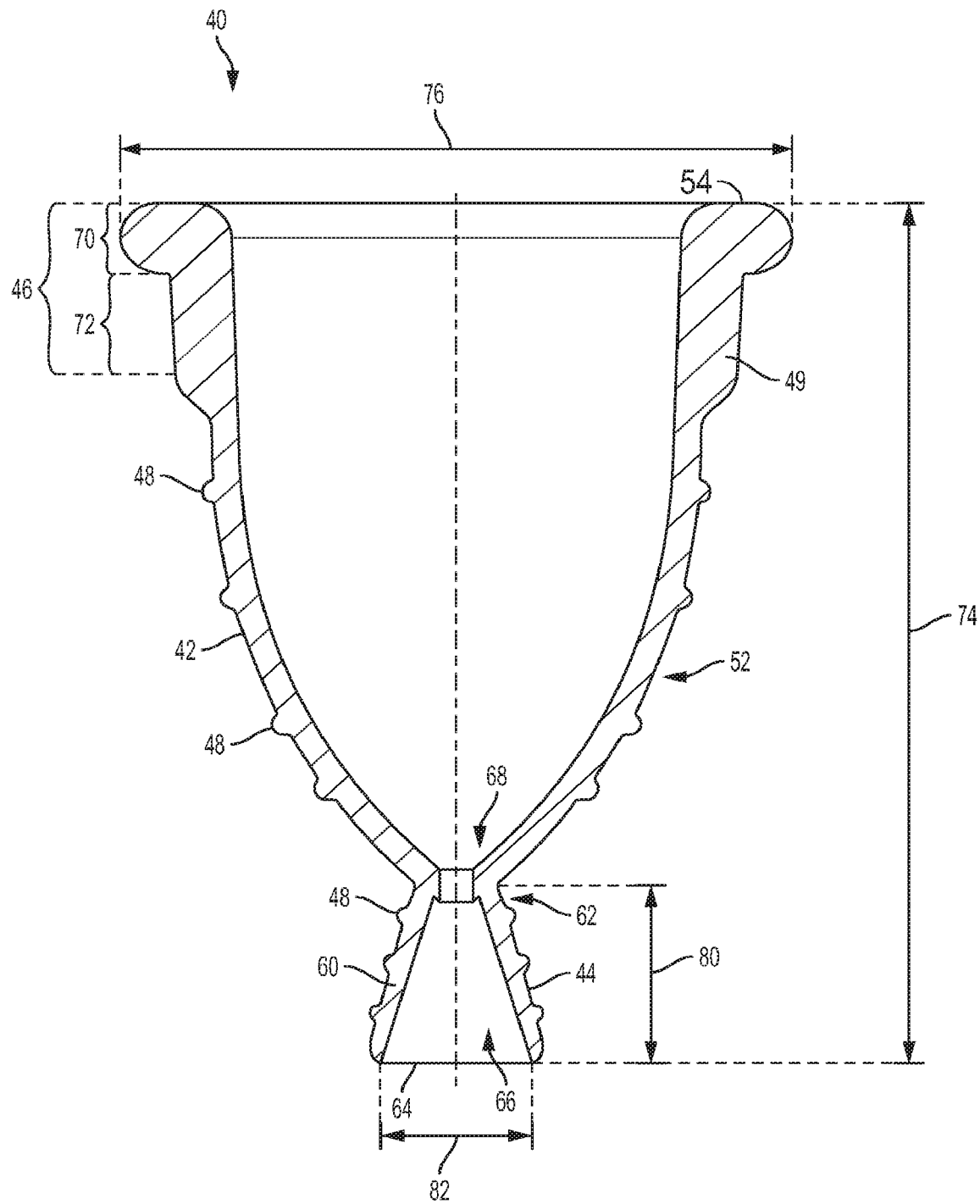
FIG. 8 is a cross-sectional view of vaginal insert device of FIG. 6A across section line A-A.

FIG. 8 is a cross-sectional view of vaginal insert device 40 of FIG. 6A across section line A-A. As shown in FIG. 8, stem 44 may have a circular transverse cross-section throughout its length. The stem 44 may have a wall 60, an upper end 62, a lower open end 64, and a hollow interior 66. The circumference and/or diameter of the stem 44 may increase from the upper end 62 to the lower open end 64. As illustrated, ridges 48 may protrude from the exterior side 52 of the wall 60. Although described as a hollow stem 44, the stem 44 may be solid. The stem 44 may be any of the stems 244a-244g described herein.

FIG. 8 further illustrates an embodiment of vaginal insert device 40 which includes a ventilation opening 68 at a region joining the upper portion 42 and the stem 44. The ventilation opening 68 may include a ventilation hole(s), slit(s), gap(s), or aperture(s). The ventilation opening 68 may include a screen or a mesh or any other component with an opening. Although depicted as a single ventilation opening 68, the ventilation opening may be more than one opening located at the region joining the upper portion 42 to the stem 44. The vaginal insert device 40 may include a plurality of ventilation openings 68. The vaginal insert device 40 may include a plurality of ventilation openings 68 in locations other than, or in addition to, the ventilation opening 68. For example, the vaginal insert device 40 may include one or more ventilation openings 68 in wall 49 of the upper portion 42, the wall 49 of the rim 46, the first section 70 and/or second section 72 of the rim 46, adjacent the rim 46, adjacent the lower end 56, in the wall 60 of the stem 44, adjacent the upper end 62 of the stem 44, or combinations thereof. The one or more ventilation openings 68 may be equidistantly or uniformly spaced around the circumference of the device 40. The one or more ventilation openings 68 may make the vaginal insert device 40 more comfortable for the patient when inserted. The one or more openings 68 may equalize the air pressure between the inside and outside of the vagina 18 (FIG. 11), when vaginal insert device 40 is inserted. The one or more ventilation openings 68 may assist in indicating the position of the device. However, having the one or more ventilation openings 68 are not required for the vaginal insert device 40 to be comfortable, useful and effective and thus may be omitted. The one or more ventilation openings 68 may prevent or limit a seal or suction created between the vaginal insert device 40 and the intravaginal or organ wall.

Referring to FIG. 8, the rim 46 may have a first section 70 and a second section 72. The first section 70 and/or the second section 72 may protrude from the exterior side 52 of the wall 49, with the first section 70 protruding a greater distance than the second section 72. Alternatives of rim 46 are contemplated. For example, when the rim 46 is present, the rim 46 may include just the first section 70 or just the second section 72. In an example, the rim 46 may include only one section, but the one section may have a different height and/or width than first section 70 (e.g., greater or lesser height and/or width). The rim 46 may protrude from the exterior side 52 of the wall the same distance from the top of the rim 46 to the bottom of the rim 46. In an example, the rim 46 may surround the exterior side 52 of the wall 49, adjacent to the upper open end 54, and may include separated sections which protrude and sections which do not protrude from the exterior side 52 of the wall 49. The rim 46 may be thicker on one side than the opposing side. The rim may be adjustable in height, location, and/or width. The rim 46 may retract and expand for therapy force as well as storage. The rim 46 may be made from one part or more than one part. The rim 46 may be made from one material, more than one material or a combination of materials. The rim 46 may be configured to apply greater pressure in one area than in another area of the rim 46. For example, the rim 46 may be weighted, either by density, thickness, material, attachments, protrusions, etc., in one portion (e.g., one half of the cross-section of the device). This portion may be configured to apply a greater pressure than the remainder of the rim 46. The remainder of the rim 46 may be constructed similarly to the remainder of the device 40 (e.g., of the same material, density, thickness, etc.). As will be described in more detail to follow, the rim 46 may be tilted, lopsided, or angled to place pressure at different locations in the vaginal canal based on anatomy, type of incontinence, and/or prolapse, for example, as shown in FIG. 27.

With reference to FIGS. 7 and 8, ridges 48 may be circular protrusions, as shown. However, other configurations are contemplated. Accordingly, ridges 48 may include the embodiment illustrated in FIGS. 7 and 8, in which ridges 48 are protrusions that may be circular rings surrounding the exterior side 52 of wall 49. Alternatively, ridges 48 may include any protrusions that extend from the exterior side 52 of wall 49, such as studs, knobs, buttons, words, numbers, symbols, logos, other shapes, including polygonal, triangular, separated, randomly separated studs, uniformly spaced studs, or square, or combinations thereof. The ridges 48 may be helical, diagonal, longitudinal, or radially placed on the device 40 (either the upper portion 42 and/or the stem 44). The ridges 48 may be the same or different on the upper portion 42 and the stem 44. The ridges 48 may be semipermeable to allow liquid, medication or lubrication to pass through.

The vaginal insert device 40 may come in different sizes, density, shapes, durability and/or different durometers to accommodate adult women with differing anatomy, women with changing or fluctuating anatomy, to accommodate different uses of the device or different activities performed while using the device. Furthermore, the dimensions of the various sections and portions of the device 40 may be modified from the multiple embodiments illustrated and disclosed herein. For example, referring to FIG. 8, the total height 74 of device 40, diameter 76 at the upper open end 54 of the upper portion 42, thickness of the wall 49 of the upper portion 42 of the device 40, diameter 82 of the lower open end 64, and height 80 of the stem 44 may be modified. The dimensions may be any of the dimensions described with respect to FIGS. 16-20 and 27-38. Modifications made to the dimensions may still retain or may improve on the intended usefulness, effectiveness and other benefits of the device. The dimensions may be modified in any combination or individually. Examples of modified dimensions are described in Table 1 and FIGS. 16-20 and 27-38 and the associated disclosure.

The following non-exclusive list of dimensions, in reference to FIG. 8, are non-limiting examples of embodiments of device 40 which are believed to be suitable for most women, and which provide the intended usefulness, effectiveness and other benefits of the device. For example, a suitable total height 74 of device 40 may be in the range of about 45 to about 75 millimeters (mm), such as about 55 to about 70 mm, such as about 58 to about 67 mm, for example, 46, 48, 50, 52, 54, 56, 58, 60, 62, 63, 64, 66, 68, 70, 72, or 74 mm+/−1 mm, including 58 mm+/−1 mm. In some embodiments, a suitable outer diameter 76 may be in the range of about 24 to about 56 mm, such as about 30 to about 48 mm, such as about 32 to about 46 mm, such as about 38 to about 44 mm, for example 24, 26, 28, 30, 32, 34, 36, 38, 40, 42, 44, 46, 48, 50, 52, 54, or 56 mm+/−1 mm, including 34, 38, or 43 mm+/−1 mm. A suitable height 80 of the stem 44 may be in the range of about 4 to about 20 mm, such as about 5 to about 10 mm or about 13 to about 15 mm, including 5, 6, 7, 8, 9, or 10+/−1 mm. A suitable thickness of the wall 49, in sections without ridges 48, of the upper portion 42, below rim 46, may be about 2.0 mm, such as 1.5, 2, or 2.5+/−0.25 mm. A suitable thickness of the wall 49, in sections with ridges 48 may be about 2.5 mm, such as 2, 2.5, or 3+/−0.25 mm. The wall 60 of stem 44 may have a suitable thickness of about 1, 1.25, 1.5, 1.75, 2, 2.25, or 2.5 mm, such as 2 mm+/−0.25 mm, in sections without ridges 48. A suitable height of rim 46 may be about 12, 14, 15, 16, or 18 mm, such as 14 or 15 mm+/−0.5 mm, with a suitable height of first section 70 being about 3, 4, 5, 6, 7, or 8 mm, such as 4 or 5 mm+/−0.5 mm and a suitable height of second section 72 being about 7, 8, 9, 10, 11, 12, or 13 mm, such as about 9 or 10+/−0.5 mm. A suitable thickness of the first section 70 may be about 3, 4, 5, 6, 7, 8, or 9 mm, such as about 4 mm+/−0.25 mm. And the second section 72 may be about 3, 4, or 5 mm, such as about 3, 4, or 5 mm+/−0.25 mm. A suitable outer diameter 82 of lower open end 64 may be about 9, 10, 10.5, 11, or 12 mm. A suitable diameter of ventilation opening 68 may be about 1.5, 2, or 2.5 mm.

FIG. 9 is a bottom view of the vaginal insert device 40 of FIG. 6A for an embodiment having ventilation opening 68. As shown, the exterior of the device 40 and the interior and exterior of the stem 44 may have a circular shape in plan view. Although other shapes are contemplated. FIG. 10 is a top view of the vaginal insert device 40 of FIG. 6A for an embodiment having ventilation opening 68. As shown, both the interior and exterior of the device 40 may have a circular shape in plan view. Although other shapes are contemplated.

Figure 11:
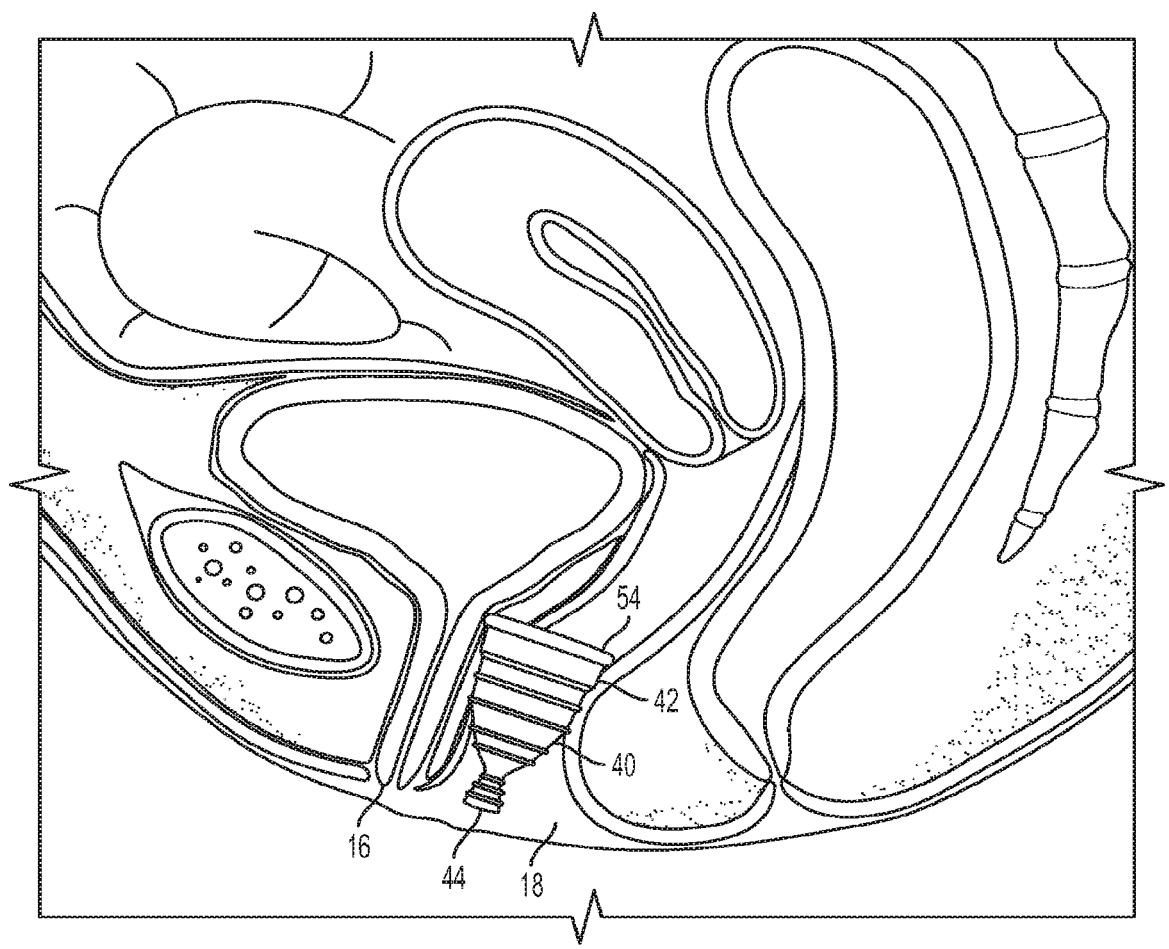
FIGS. 11-13 each illustrate a cross-section of the pelvic region of a female as well as an embodiment of the vaginal insert device inserted in the vagina.
Figure 12:
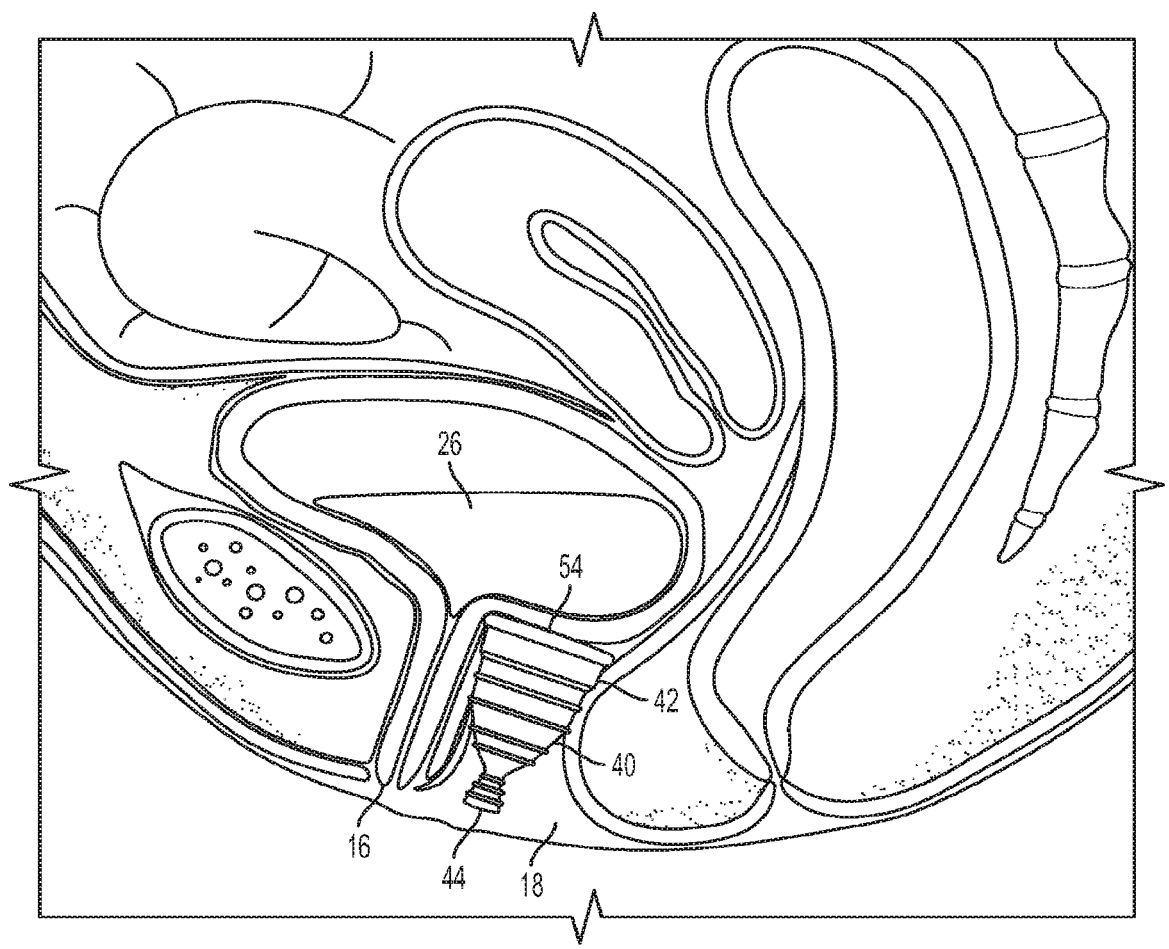
Figure 13:
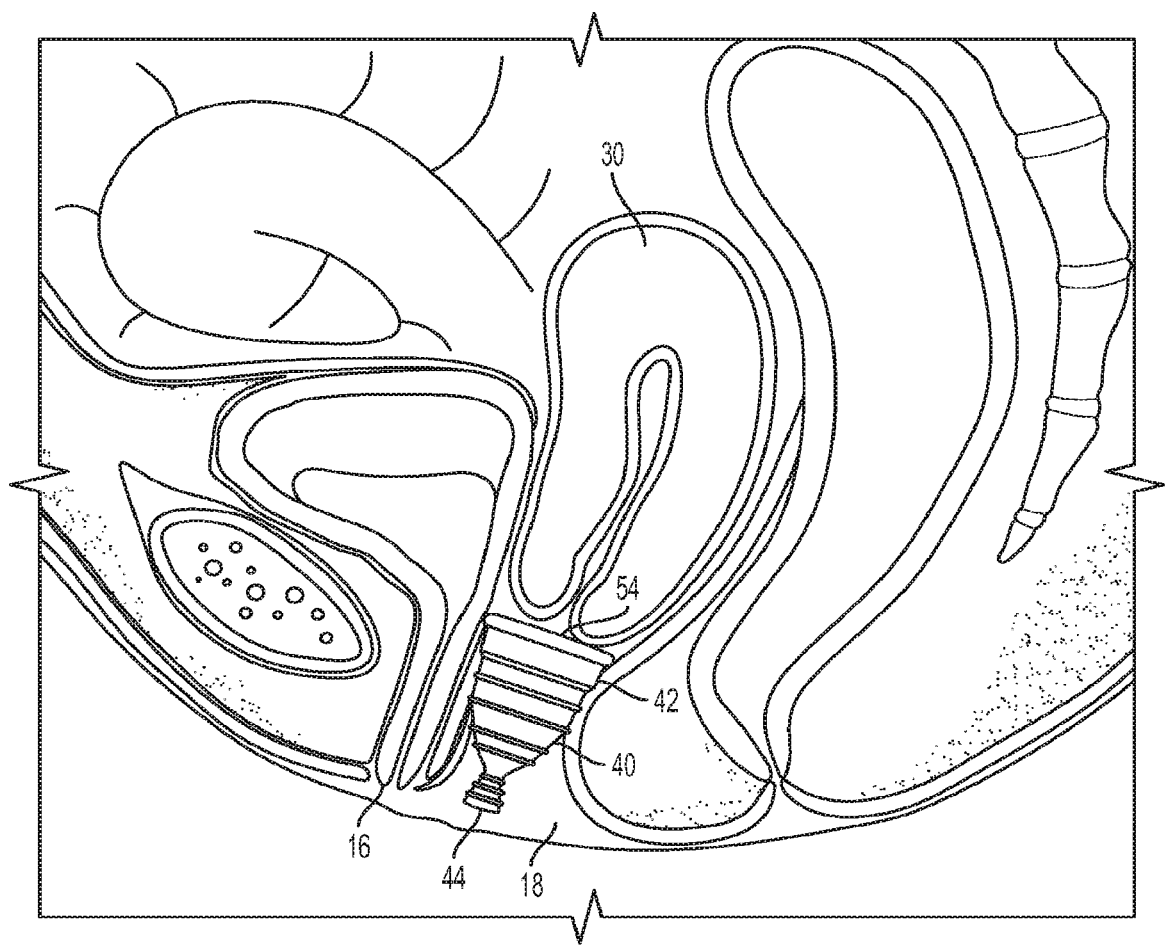

FIG. 11 is a cross-section of the pelvic region of a female illustrating an embodiment of the vaginal insert device 40 inserted in the vagina 18 and applying pressure on the urethral sphincter 16 and/or the bladder neck 15 (FIG. 33) to manage, improve, prevent, treat, and/or eliminate female urinary incontinence. A user may insert the device 40 according to FIG. 14. Once inserted, the rim may be aligned with an intravaginal wall, such as the urethral sphincter and/or bladder neck to apply pressure thereto. The ridges may also apply pressure to the intravaginal walls. The pressure applied at the urethral sphincter 16 and/or bladder neck 15 may reduce or eliminate urine leakage. FIGS. 12 and 13 are each a cross-section of the pelvic region of a female illustrating an embodiment of the vaginal insert device 40 inserted in the vagina 18 to manage, improve, prevent, treat, and/or eliminate POP, in addition to applying pressure on the urethral sphincter 16 to manage, improve, or eliminate female urinary incontinence. In particular, in FIG. 12, vaginal insert device 40 is inserted in the vagina 18 to manage, improve, prevent, treat, and/or eliminate a prolapsed bladder 26. In FIG. 12, the upper open end 54 may support the bladder 26. The rim and ridges may also apply pressure to an intravaginal wall, such as the urethral sphincter 16 and/or bladder neck 15. The pressure applied at the urethral sphincter 16 and/or bladder neck 15 may reduce or eliminate urine leakage. In particular, in FIG. 13, vaginal insert device 40 is inserted in the vagina 18 to manage, improve, prevent, treat, and/or eliminate a prolapsed uterus 30. In FIG. 13, the upper open end may support the uterus 30. Although described separately, the device 40 may apply pressure to the intravaginal walls (e.g., FIGS. 11 and 12) and support the bladder and/or uterus (FIGS. 12 and 13) simultaneously or as the body changes over time (e.g., as the bladder fills).

As illustrated in FIGS. 11-13, the upper open end 54 of the upper portion 42 is the innermost portion of the vaginal insert device 40 when inserted into the vagina. As further illustrated in FIGS. 11-13, the removal portion or stem 44 of the vaginal insert device 40 may be accessed from the exterior of the vagina 18 when the vaginal insert device is inserted. The stem 44 may assist in insertion, removal, and/or positioning of the vaginal insert device 40 within the vagina. Ridges 48 on stem 44 may provide better grip for removal of the device 40 by a patient. The stem 44 may also be used to position the device for therapy force, organ support and comfort. The rim 46 and/or the ridges 48 on the upper portion 42 may apply pressure to the organ walls shown in FIGS. 11-13 to manage, improve, prevent, treat, and/or eliminate female incontinence, including urinary incontinence and fecal incontinence, POP, or POP and urinary and/or fecal incontinence, and combinations thereof.

Figure 14A:
FIGS. 14A and 14B illustrate a method for inserting an embodiment of the vaginal insert device into a patient's vagina.
Figure 14B:
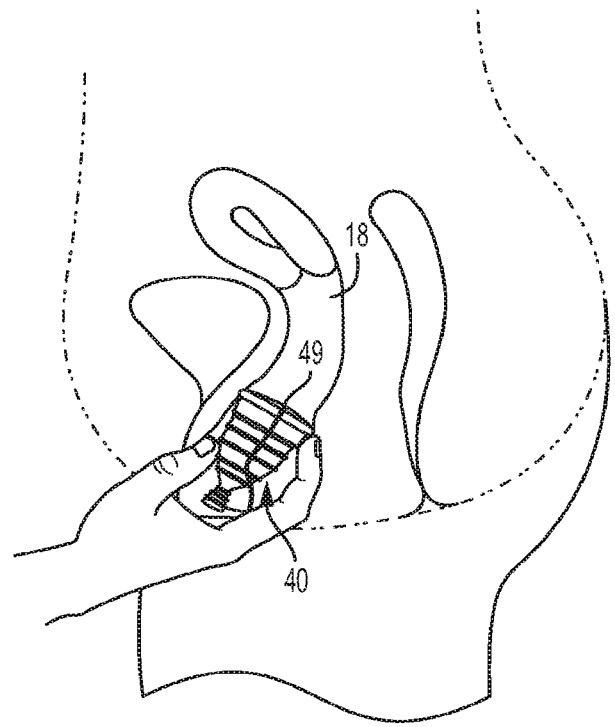

FIGS. 14A and 14B illustrate a method for inserting vaginal insert device 40 into vagina 18. As illustrated in FIG. 14A, a patient may squeeze the wall 49 of the upper portion 42 to make the upper portion more compact. The more compact shape may allow for easier insertion of the vaginal insert device 40 into the vagina 18. The user may manually squeeze the upper portion 42 between two or more fingers or otherwise within the hand. Alternatively, the user may use a tool, such as the applicator 84, to assist in squeezing the device 40 for insertion. As illustrated in FIG. 14B, the user may then insert the more compact shaped device 40 into the vagina 18. The user may insert the device 40 manually (e.g., with one or both hands) or with a tool (e.g., applicator 84). Once vaginal insert device 40 is manually inserted into the vagina 18, the wall 49 of upper portion 42 may expand back to its original shape or near original shape, thus allowing the vaginal insert device 40 to apply pressure to the interior walls of the vagina and internal organs. Although this method of insertion is one example, in a higher durometer silicone or other material, the device does not necessarily have to collapse for insertion.

Figure 15C:
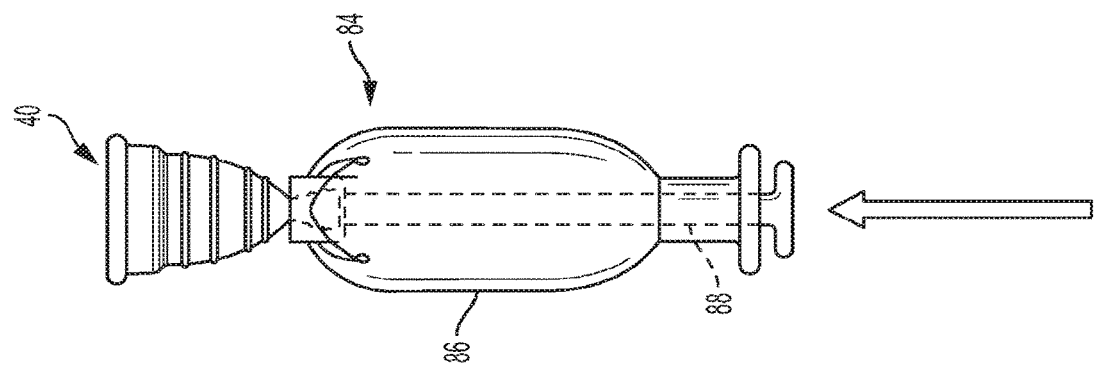
FIGS. 15B and 15C illustrate a cross-section of the pessary applicator of FIG. 15A, and a method of using same to insert an embodiment of the vagina insert device into a patient's vagina.
Figure 15B:
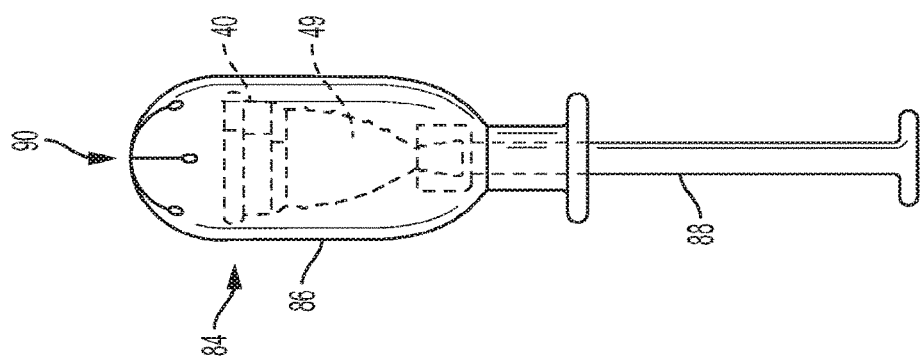
Figure 15A:
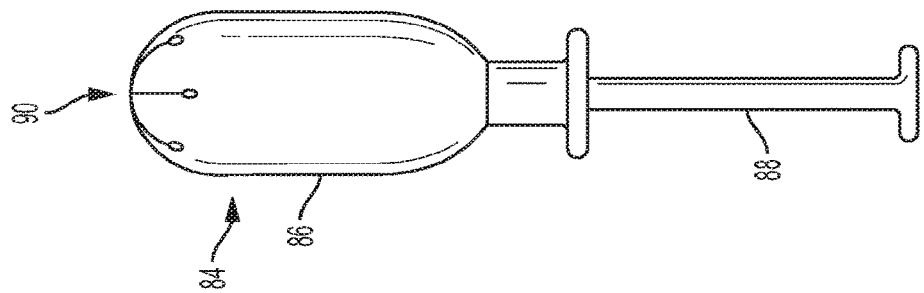
FIG. 15A illustrates a side-view of a pessary applicator.

FIG. 15A illustrates a side-view of a pessary applicator 84 which may be used to assist in inserting, positioning, or removing a vaginal insert device 40 into a patient's vagina 18 (FIG. 14B). Pessary applicator 84 may include an insertion member 86, a top portion 90 of the insertion member, and a plunger 88. Pessary applicator 84 may be similar to a tampon applicator. In an embodiment, the insertion member 86 may generally have a greater or smaller circumference than a tampon applicator to accommodate a vaginal insert device 40 or the stem 44, which when the entire device is compacted has a shape which may be larger than the circumference of a tampon and if the stem alone is compacted into the device may be generally smaller than a tampon. FIGS. 15B and 15C illustrate a cross-section of the pessary applicator 84 of FIG. 15A, and a method of using the applicator to insert a vaginal insert device 40 into a patient's vagina 18. As is illustrated, vagina insert device 40 is housed inside insertion member 86 in a compacted shape. Similar to the process of insertion of a tampon into a vagina using an applicator, insertion member 86 of pessary applicator 84 is inserted into the patient's vagina 18, and the plunger 88 is pushed towards the insertion member, ejecting the vaginal insert device 40 through the top portion 90. The pessary applicator 84 is then removed from the vagina 18, and the vaginal insert device 40 remains in place in the vagina, expanded back to its normal shape. The vaginal insert device 40 which has been inserted is positioned such as is illustrated in any of FIGS. 11-13. The vaginal insertion applicator 84 may also assist to position the device appropriately into the vagina. The pessary applicator 84 may work together with the device 40 to click into place and allow the device to expand or retract for therapy force, position, and organ support and placement orientation to manage, improve, prevent or eliminate the symptoms associated with incontinence and/or pelvic organ prolapse. The applicator 84 may be filled with medication and/or hormones and may be used to administer the medication, hormones, or drug into the cone-shaped body of the device 40 for treatment holistically, homeopathically, or by prescription for treatment of hormone levels (e.g., hormone replacement therapy), yeast infections, sexually transmitted diseases or may be used for birth control, anti-fungal or anti-bacterial purposes. The applicator 84 may be made of one material or a combination of materials. The applicator 84 may be one piece or made from multiple pieces or parts.

Referring now to FIGS. 16-20, an exemplary vaginal insert device 100 is shown. The vaginal insert device 100 may be similar to the device 40. The vaginal insert device 100 may include any of the modifications, shapes, sizes, materials, dimensions, uses, or any combinations thereof as described with respect to the vaginal insert device 40. Any of the modifications or alternatives of the rim, stem, shape of the upper portion, etc., previously described may be applied separately or in combination to the vaginal insert device 100. The method of insertion described in FIGS. 14 and 15 may apply to the vaginal insert device 100.

Figure 16:
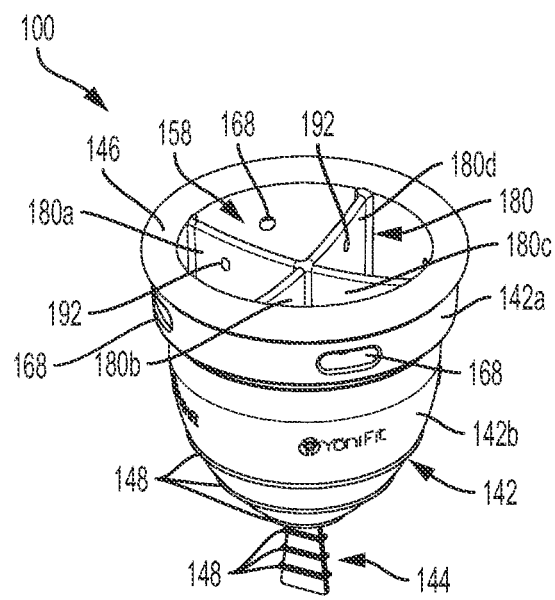
FIG. 16 illustrates a perspective view of a vaginal insert device, in accordance with embodiments of the present disclosure.

FIG. 16 illustrates a side view of the exemplary vaginal insert device 100. The vaginal insert device 100 may include an upper portion 142 and a lower, stem-like, removal portion or stem 144. The upper portion 142 may be cone-shaped. That is, the upper portion 142 may have a first diameter which decreases to a second diameter. The decreasing in diameter may be gradual. The cone-shaped body of the upper portion 142 may thus include a changing diameter. Although described herein as cone-shaped, other shapes of the upper portion 142 are contemplated. Such other shapes may include changing diameters such that a first diameter is configured to apply pressure to an intravaginal or organ wall and a second diameter is configured to be smaller than the first diameter and not interact with an intravaginal wall. Such shapes may include trapezoid, spheres, cylinders, cubes, pyramids, hexagonal prisms, etc.

The upper portion 142 may include an enlarged portion 142*a* (e.g., at the top of the upper portion 142), a narrower or narrowing portion 142*b* (e.g., at the lower end of the upper portion 142), and a rim 146 that protrudes from the upper portion 142 (e.g., at the top of the upper portion 142). The rim 146 may be the same as the rim 46. The rim 146 may be similar to the first section 70 and the enlarged portion 142*a* may be similar to the second section 72. In an embodiment, the rim 146 may be omitted and may not be present. In an embodiment, the rim 146 is part of the enlarged portion 142*a*. Although a cone-shaped body is depicted for the narrower or narrowing portion 142*b*, it may also be a circular portion, cylindrical portion, triangular, umbrella or pyramid shaped portion, or other shapes described herein. The upper portion 142 may have a circular transverse cross-section that may reduce in diameter from an upper end, such as upper open end 154, to a base or lower end 156. The reduction in diameter may be a reduction in internal diameter of the upper portion 142, a reduction in the external diameter of the upper portion 142, or a combination thereof. The circumference of the upper portion 142 may decrease from the upper open end 154 to the lower end 156. The upper open end 154 may expose the open portions 158 to atmospheric pressure (when not inserted) and to the interior of the vagina (when inserted).

As further illustrated and as described in more detail below, the upper portion 142 may include ridges 148 which may be spaced apart from the top of the upper portion 142 to the lower end of the upper portion 142. The ridges 148 may be spaced along the entire length or along a portion of the length of the upper portion 142. The ridges 148 may alternatively be indentations. The ridges 148 may be randomly or uniformly spaced. The stem 144 may also have indentations or ridges 148, which like the upper portion may be spaced apart from the top of the stem 144 to the lower end of the stem 144. The ridges 148 may be spaced along the entire length or along a portion of the length of the stem 144. The ridges 148 may include a logo. The ridges 148 may be a mix of shapes, for example, circular and logo, as depicted. The ridges 148 may support the device within the vagina, apply pressure to organ walls, or a combination of both. Although depicted as running transverse or perpendicular across the height H of the device 100 (or relative to a longitudinal axis of the device 100), the ridges 148, of either or both of the upper portion 142 and the stem 144, may be parallel, diagonal, helical, or transverse, or combinations thereof. The ridges 148 are depicted as generally straight, but may also be wavy, zigzag, or course another non-linear path. The non-linear path may, in total, run transversely, in parallel, or diagonal relative to the longitudinal axis of the device. The ridges 148 may include any protrusions that extend from the exterior side 152 of wall 149, such as studs, knobs, buttons, words, numbers, symbols, logos, other shapes, including polygonal, triangular, separated, randomly separated studs, uniformly spaced studs, or square, or combinations thereof. The ridges 148 may be helical, diagonal, longitudinal, or radially placed on the device 100 (either the upper portion 142 and/or the stem 144). The ridges 148 may be the same or different on the upper portion 142 and the stem 144. The ridges 148 may be semi-permeable to allow liquid, medication or lubrication to pass through.

With continued reference to FIG. 16, the vaginal insert device 100 may include a member 180. The member 180 may be configured to apply pressure through the wall 149 of the vaginal insert device 100 and onto an intravaginal or organ wall. The member 180 may be located within the interior of the upper portion 142. The member 180 may take on any shape configured to apply pressure to the intravaginal wall and/or support organs. In an embodiment, the member 180 extends from adjacent the upper end of the device 100 to the lower end 156. In an embodiment, the member 180 is located only near the upper end, for example, only in the upper ¼, ⅓, and/or ½ of the device 100 and/or may be adjacent the rim 146. In an embodiment, the member 180 extends between two or more points on the interior side 150 of the wall 149. In an embodiment, the member 180 extends from only one point on the interior side 150 of the wall 149. Any of the previously described or forthcoming descriptions, adjustments, and/or modifications to the member 180 may be presented, alone or in combination, to the device 100 to apply pressure to the intravaginal wall and/or support organs in accordance with the principles of the current disclosure.

The member 180 may be a rib 180 and will be referred to herein as a rib for ease of disclosure. However, other structures or configurations are contemplated to achieve the application of pressure as the rib 180. The rib 180 may have four rib sections or members 180*a*, 180*b*, 180*c*, 180*d*. The rib 180 may take on a variety of forms, some exemplary shapes and arrangements of the rib 180 are described herein. Any combination of the exemplary shapes is contemplated.

The rib 180 may be cross-shaped, "T" shaped, or "X" shaped, although other shapes and arrangements are contemplated (such as, for example, a triangular shape, a pentagonal shape, a "Y," "K," "V" shape, etc.). The rib 180 may also be a star shape, meeting in one central location, in multiple locations or not meeting at all. For example, in FIG. 19, the rib 180 may have four members meeting at a central location. In FIG. 32B, the rib 180 may have six members meeting at a central location. Although more or fewer members are contemplated. The rib 180 may be one or more parallel ribs or members offset from the central axis, a single rib or member crossing the central axis, both the one or more parallel ribs or members offset from the central axis and the single rib or members crossing the central axis, and/or chords which extend from one interior surface to another interior surface without intersecting, etc., or any combination thereof. The rib 180 may be spokes or members which cross or meet at the center of the spokes or offset from the center of the spokes. The spokes or members may or may not meet the interior wall of the vaginal insert device. The rib 180 may be a member that may extend between diametrically opposing points on the interior wall of the upper portion 142. The member may connect to the interior wall at the diametrically opposing points. The member may include two or more members spaced equidistantly around a circumference of the interior wall of the cone-shaped body. The two or more members may meet at a center point of the cone-shaped body. The member may be a cross-shaped rib having four ends. Each of the four ends may meet the interior wall of the cone-shaped body. A device 100 of larger size (e.g., the device of FIG. 32) may have more members or ribs than a device 100 of smaller size (e.g., the device of FIG. 27).

The rib 180 may or may not extend to the interior surface of the base or lower end 156. That is, there may be a space between a lower end of the rib 180 and the inner wall of the upper portion 142 at the lower end 156. In this case, the rib 180 may be located in an upper area of the upper portion 142, such as the upper ¼, upper ⅓, or upper ½ of the upper portion 142. The rib 180 may be located adjacent the rim 146. The rib 180 may be horizontally aligned with the rim 146 and may be the same height as the rim 146 such that pressure is only applied at the rim 146 (e.g., applied by both the rim 146 and the adjacent ribs). The rib 180 may take any shape or form that supports the vaginal insert device 100, applies force and/or pressure to organ walls, and/or prevents or inhibits prolapse of organs. The rib 180 may be any length, thickness, and/or width. The ribs 180 may not extend all the way to the base or lower end 156. The rib 180 may be offset from a central axis of the device 100. The rib 180 may allow for adjustable or selective pressure around a circumference of the device 100. For example, the location where the rib 180 approaches or meets with the upper portion 142 may apply a greater force to an organ wall than a location spaced apart from the rib 180.

Although described as a single rib 180, the rib 180 may be constructed of two rib portions or members that cross in the middle (e.g. a first rib portion or member of sections 180a, 180c crossing a second rib portion or member of sections 180b, 180d) or four rib portions or members that meet in the middle (e.g. rib sections 180a, 180b, 180c, 180d meeting in the middle). Where more than one rib member is provided, the rib members may be spaced equidistantly from one another. Alternatively, the rib members may be randomly located with respect to one another and/or may be offset such that one portion of the device 100 is configured to apply a greater pressure and/or greater support than the other side. That is, the side with more rib members may apply greater pressure or support than the side with fewer rib members. The rib 180 may be formed as an integral unit or as separate parts coupled together. The rib 180 may be made from one material, two or more materials or a combination of materials and/or parts. The rib 180 may be semi-permeable. The rib 180 may be formed integral with the upper portion 142 or may be formed as a separate component otherwise secured within the upper portion 142. The rib 180 may be removable from the upper portion 142. The entirety of the device 100, including the rib 180, may be formed as a single, unitary, integral device formed of a single material.

Although the rib 180 is shown with four rib sections or members 180a, 180b, 180c, 180d, more or fewer rib sections may be provided, e.g., one, two, three, four, five, size, seven, eight, nine, ten, or more rib sections are contemplated. The number of rib sections or members may be selected to adjust the amount of pressure applied to the organ wall, such as the uterine or bowel wall, to reduce, manage, improve, prevent or eliminate incontinence. Each rib section or member 180a, 180b, 180c, 180d may include one or more openings 192. The one or more openings 192 may facilitate flow of fluids and/or may assist in equalizing pressure through the vaginal insert device 100 and/or may act as an indicator for placement of the device 100. The rib sections or members (e.g., 180a, 180b, 180c, and 180d) in combination with the interior wall or interior side 150 of the wall 149 may define one or more open or hollow portions 158. As depicted in FIG. 16, the device 100 includes four open portions 158.

The rib 180 may add support to the organs when pelvic organ prolapse occurs or to prevent organs from displacement. The rib 180 may provide additional pressure on the vaginal wall, urethral sphincter, and/or the bladder neck to assist in reducing, managing, improving, preventing, treating, and/or eliminating Incontinence. The rib 180 may also assist in preventing tissue from descending into the open portion 158 of the device. Overtime, the tissue and/or organs may descend into the device 100. The inclusion of rib 180 may prevent this by blocking entry of the tissue into the device 100. The rib 180 may prevent sinking of the bladder, cervix, or rectum. The rib 180 may place sufficient pressure on the vaginal wall at the bladder neck or urethral sphincter through the intravaginal canal to effectively reduce leakage.

When included, the rim 146 may be expandable or retractable to change therapy force and organ support. The rim may be larger or thicker on one side and smaller or thinner on the opposing side for therapy force. The rim may be semi-permeable to allow for medication, lubrication gas or liquid to pass through. The rim 146 may be aligned with the bladder neck when inserted. The rim 146 may apply pressure (therapy force) to an organ wall. The rim 146 and the rib 180 may, together, apply pressure and/or support, the organs and/or organ walls within the vagina.

The rim 146 may be configured to apply greater pressure in one area than in another area of the rim 146. For example, the rim 146 may be weighted, either by density, thickness, material, attachments, protrusions, ribs, members, etc., in one portion (e.g., one half of the cross-section of the device). This portion may be configured to apply a greater pressure than the remainder of the rim 146. The remainder of the rim 146 may be constructed similarly to the remainder of the device 100 (e.g., of the same material, density, thickness, etc.).

Figure 17:
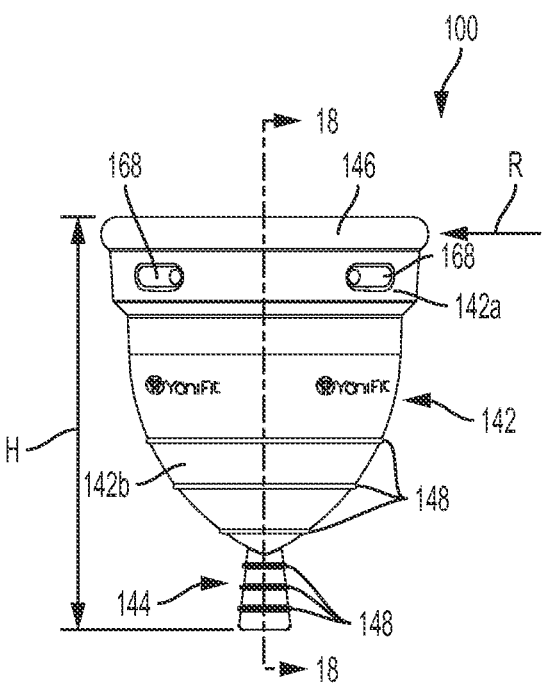
FIG. 17 illustrates a side view of the vaginal insert device of FIG. 16.

Referring to FIGS. 16 and 17, the vaginal insert device 100 may include one or more ventilation openings 168. The ventilation openings 168 may be equally spaced around a circumference of the vaginal insert device 100. Alternatively, the ventilation openings may be spaced offset or randomly about the circumference of the device 100. The ventilation openings 168 may be located in the enlarged portion 142a of the upper portion 142. Alternatively, or additionally, the ventilation openings 168 may be located in the narrower or narrowing portion (e.g., cone-shaped portion or body) 142b.

The one or more ventilation openings 168 may allow fluid flow through the vaginal insert device 100 such that pressure may be equalized across the vaginal insert device 100 and/or such that a vacuum pressure in the device is released. The one or more ventilation openings 168 may also act as an indicator for placement of the device. The one or more ventilation openings 168 may act as a means to connect an applicator (e.g., the applicator of FIG. 15) for positioning or applying therapy force. The one or more ventilation openings 168 may act as a passageway for the administration of medication either by prescription or over the counter for homeopathic remedies for yeast infections, sexually transmitted diseases, hormone levels, or birth control. It may act as a conduit to attach a testing strip to indicate PH levels, hormone levels or pelvic floor strength. The ventilation opening 168 may prevent or limit a suction effect on the device when inserted in to the vagina.

Figure 18:
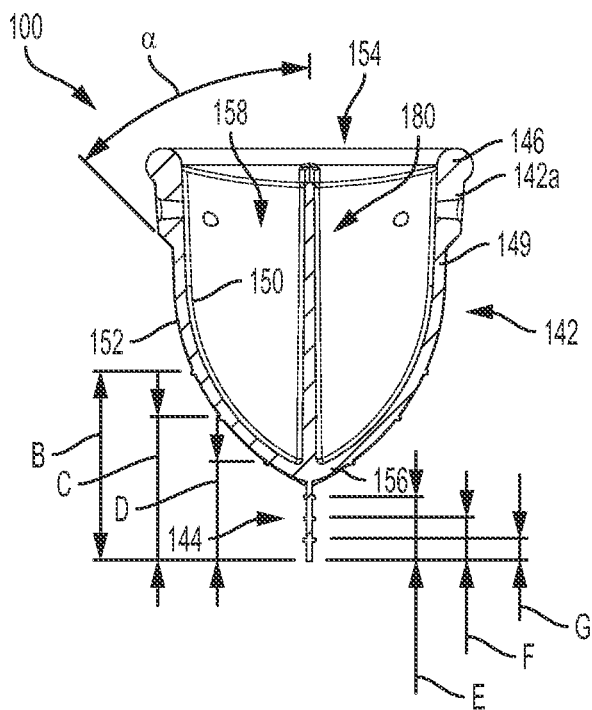
FIG. 18 illustrates a cross-sectional view of the vaginal insert device of FIG. 16 across the section line 18-18 of FIG. 17.
Figure 19:
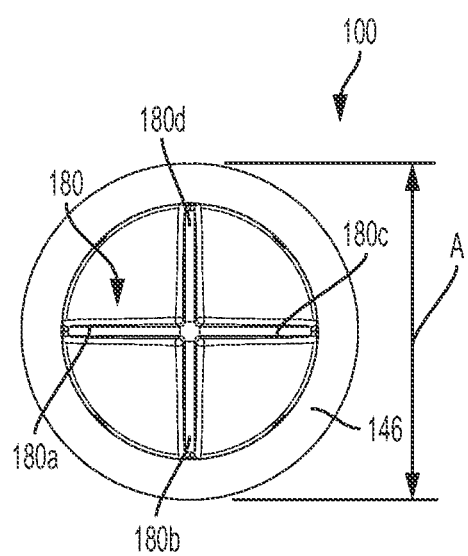
FIG. 19 illustrates a top view of the vaginal insert device of FIG. 16.
Figure 20:
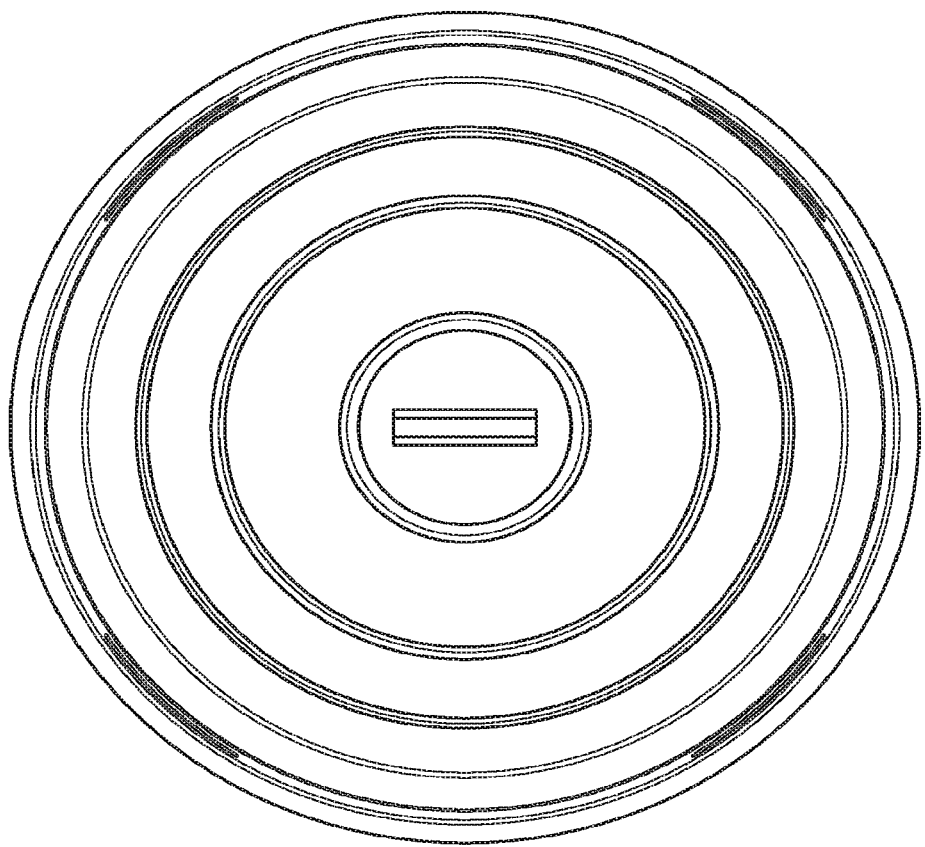
FIG. 20 illustrates a bottom view of the vaginal insert device of FIG. 16.

Referring to FIG. 18, a cross-sectional view of the vaginal insert device 100 taken along the line 18-18 of FIG. 17 is shown. The rib 180 may extend from adjacent or just below the rim 146 to a base or lower end 156 of the upper portion 142. In this manner, the rib 180 may apply pressure and support to the rim 146 and the upper portion 142, thus applying pressure and support to the uterine and/or rectum wall.

The vaginal insert devices of the present disclosure may be sized to fit any number of vaginal sizes. Table 1 below shows a list of exemplary sizes for vaginal insert devices 40, 100. The dimensions labeled in Table 1 may be seen in FIGS. 16-20. The diameter A in Table 1 may be the same as the diameter 76 of FIG. 8 and/or the diameter J of FIGS. 27-38. The angle α may be 45 degrees, the radius of the rim R may be 0.10 inches (2.54 mm), and the length H of the device may be 2.29 inches (58.17 mm). The distances B, C, and D locating the ridges on the upper portion may be 1.05 inches (26.67 mm), 0.80 inches (20.32 mm), and 0.55 inches (13.97 mm), respectively. The distances E and G locating the ridges on the stem may be 0.35 inches (8.89 mm) and 0.12 inches (3.05 mm), respectively. The distance F may be 0.24 inches (6.10 mm) for Devices 2 and 5 and 0.23 inches (5.84 mm) for Devices 3, 4, and 6.

TABLE 1

Exemplary Diameters for Vaginal Insert Device

|   | Device 1 | Device 2 | Device 3 | Device 4 | Device 5 | Device 6 |
|---|----------|----------|----------|----------|----------|----------|
| A | 2.05 in (52 mm) | 1.81 in (46 mm) | 1.65 in (42 mm) | 1.50 in (38 mm) | 1.34 in (34 mm) | 1.18 in (30 mm) |

As shown in FIGS. 16 and 18, the upper portion 142 may have a cone-shaped body as depicted, although the upper portion 142 may have other shapes, such as, for example, triangular, rounded, cylindrical, umbrella or pyramid shaped. The upper portion 142 may have an open top. The upper portion 142 may have a circular transverse cross-section throughout its length (FIG. 19), or other shaped cross-sections, such as oval, square, rectangular, triangular, pentagonal, hexagonal, or octagonal. The upper portion 142 as depicted, may have a wall 149 with an interior wall or interior side 150 and an exterior wall or exterior side 152, an upper open end 154, the base or lower end 156, and a hollow interior, including a plurality of open portions 158, wherein the circumference of the upper portion 142 decreases from the upper open end 154 to the lower end 156. As illustrated, rim 146 may be circular and may surround and protrudes from the exterior side 152 of the wall 149 and may be adjacent to the upper open end 154. Ridges 148 may be circular rings which surround the exterior side 152 of wall 149. The ridges 148 may also include a logo. The ridges 148 may be any shape, including polygonal, semi-circular, triangular, square, letters, symbols, numbers, or logos, studs, knobs, buttons, bumps, etc., or combinations thereof. As further illustrated, the stem 144 may extend from the lower end 156 of the upper portion 142. The upper portion 142 and the stem 144 may be fabricated as an integral one-piece device formed of a single material. Alternatively, the upper portion 42 and the stem 44 may be made from one material or more than one materials. It may be made from one part or multiple parts that may attach and detach, expand or retract. The upper portion may be made of a semi-permeable material to allow for medications, liquid, gas or lubrication to pass through. The upper portion 142 and stem 144 may be permanently or detachably coupled together. The stem 144 may have a flat, triangular body. The flat, triangular body of the stem 144 may expand radially outward and downward from the lower end 156. The cone-shaped body of the upper portion 142 may expand radially outward from the lower end 156 to the upper open end 154. The stem 144 may be any of the stems 244a-244g.

With continued reference to FIGS. 16 and 17, the one or more ventilation openings 168 may include a ventilation hole, slit, gap, or aperture. The one or more ventilation openings 68 may include a screen, or a mesh or any other component with an opening. The vaginal insert device 100 may include a plurality of ventilation openings 168. The vaginal insert device 100 may include a plurality of ventilation openings 168 in locations other than, or in addition to, the ventilation openings 168. For example, the vaginal insert device 40 may include a ventilation opening in wall 149 of the upper portion 142, in the stem 144 (similar to FIG. 8) or in the side walls of the stem 144, in the rim 146, through a ridge 148, and/or through a rib 180. The one or more ventilation openings 168 may make the vaginal insert device more comfortable for the patient when inserted. The one or more openings may also equalize the air pressure between the inside and outside of the vagina 18, when vaginal insert device 100 is inserted. However, having a ventilation opening 168 is not required for the vaginal insert device 100 to be comfortable, useful and effective. The ventilation openings 168 may prevent a suction effect on the device.

With continued reference to FIG. 18, the rim 146 and the enlarged portion 142a may protrude from the exterior side 152 of the wall 149, with the rim 146 protruding a greater distance than the enlarged portion 142a. Multiple alternative embodiments of rim 146 and enlarged portion 142a are possible, including an embodiment in which rim 146 and/or enlarged portion 142a are omitted and the height dimension of the remaining of the rim 146 and/or enlarged portion 142a is increased such that the section is the same height as the combination of 142a and 146 according to the embodiment of FIG. 18. Certain embodiments may be made of one part or multiple parts and from one material, more than one material or a combination of materials. The parts and materials may be detachable, attachable, expandable or retractable.

With reference to FIGS. 16-20, ridges 148 may not be limited to the circular protrusions shown. Accordingly, ridges 148 may include the embodiment illustrated in FIGS. 16-20, in which ridges 148 are protrusions that may be circular rings surrounding the exterior side 152 of wall 149. However, ridges 148 may also include any protrusions that extend from the exterior side 152 of wall 149, such as a plurality of studs, knobs, buttons, bumps, letters, logos, numbers, etc. The ridges 148 may assist in preventing displacement of the device thus preventing displacement of the organs by providing friction with the internal vaginal wall. The ridges 148 may also support the device and the tissue if the user suffers from prolapse or may prevent organ displacement thus preventing prolapse. The ridges 148 may assist in reducing, managing, improving, preventing, treating, and/or eliminating incontinence. The ridges 148 may also be made from a semi-permeable material to allow for medication, liquid, gas or lubrication to pass through. The ridges 148 may apply pressure (therapy force) to the vaginal wall or organ walls. The ridges 148 may be spaced equally and/or uniformly along the upper portion 142. Where a logo, words, numbers, etc. are provided as a ridge, such as depicted in FIGS. 16 and 27-38, a line extending through the center of the logo and parallel to the remaining ridges may be spaced equally and/or uniformly along the upper portion 142 with the remaining ridges 148. Alternatively, the ridges 148 may be extend along an entire length or a partial length of the upper portion 142 and may be random or uniform or any combination thereof.

The vaginal insert device 100 may be used, inserted, manipulated, etc. similar to or the same as the vaginal insert device 40 as described with respect to FIGS. 11-15 and FIGS. 39-41. Any of the features, modifications, or uses of the vaginal insert device 40 may be used with the vaginal insert device 100 and also the reverse.

Referring now to FIGS. 21A-21F alternative embodiments for the stems 44, 144 are shown. The stems 244a, 244b, and 144c are shown in partial cross-section in FIGS. 21A-21C. In addition to the following examples, the stem may be a ball, loop, handle, tab, plus sign, etc., or combinations thereof. The stem may be a flat, rectangular stem, such as stem 244g shown in FIG. 33. The vaginal insert devices of any of FIGS. 6, 16, and 27-38 may be provided with any of the stems 244a-244f, with the stem 144 of FIG. 16, or with the stem 44 of FIG. 7. The user may determine the position of the vaginal insert device of the present disclosure while the device is inserted into the vagina based on the location of the stem 44, 144, 244. Rotation of the stem 44, 144, 244 may alter the pressure placed on the uterine wall. Rotation of the stem 44, 144, 244 may decrease and/or increase the pressure on the urethral wall. Rotation of the stem 44, 144, 244 may allow for selective and/or adjustable pressure to be applied to an organ wall. For example, a slight rotation of the stem 44, 144, 244 may result in a 50% decrease in urethral pressure, see, for example, FIG. 24. The ridges 48, 148, 248 on the stem 44, 144, 244 may be one of studs, knobs, buttons, words, numbers, symbols, logos, other shapes, including polygonal, triangular, or square, or combinations thereof. The ridges may assist in positioning, location, and/or gripping the vaginal wall.

The stem 44, 144, 244 may assist with orienting the device 40, 100 and may have markings indicating placement such as an arrow, ball, protrusion or numbering system which may be felt or seen to determine placement. The stem 44, 144, 244 may have a system in which the patient may rotate the stem to increase or decrease the amount of therapy force or pressure placed on the intravaginal wall. The stem may attach to an applicator. Both may be used together or separately to change the amount of therapy force the device places on the organs either by rotating the device or by acting as a mechanism for the device to expand or retract. Rotation of the stem may be performed with a portion of the hand on the lower end 154 of the device to assist in movement of the device. Alternatively, rotation of the stem may occur with a hand or finger(s) gripping the stem alone. The stem 44, 144, 244 may also act as a conduit for medication administration or lubrication either working together with the applicator or without need of the applicator. The stem may be made of one material, more than one material or a combination of materials. An applicator may be provided to rotate, position, and/or administer medicine, and or combinations thereof. The applicator may assist in the rotating, positioning of and/or administering medication, or combinations thereof. The applicator may be such as described in FIG. 15.

Figure 21A:
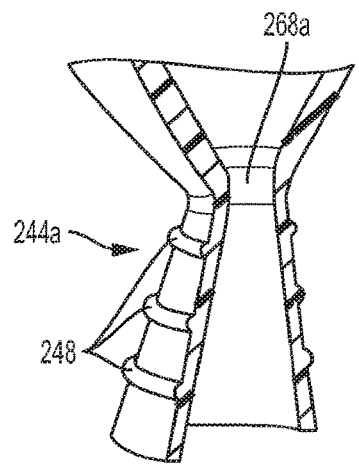
FIGS. 21A-21F illustrate perspective views of exemplary stems, in accordance with embodiments of the present disclosure.

FIG. 21A shows a stem 244a similar to the stem 44 of FIGS. 7 and 8. The stem 244a may be substantially conical in shape with ridges 248 provided circumferentially around an outer surface of the stem 244a. A ventilation opening 268a may or may not be provided in the stem 244a. The stem 244a may have a pull strength of about 12 to about 16 lbf, such as about 13 to about 15 lbf, such as about 14.03 lbf.

Figure 21B:
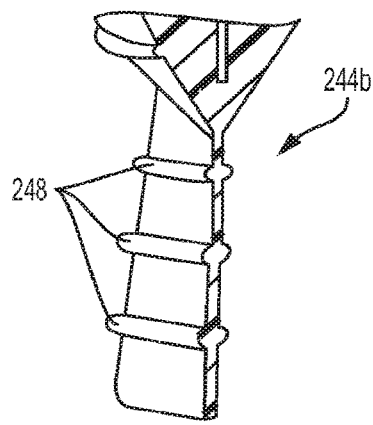

FIG. 21B shows a stem 244b similar to the stem 144 of FIG. 16. The stem 244b may be triangular in shape as depicted, or rectangular, and substantially flat or two-dimensional (the flat or two-dimensional shape creating a plane). The stem 244b may have an outwardly tapering or expanding body from the lower end of the upper portion to the distal end of the stem 244b (e.g., triangular). Alternatively, the stem 244b may have a body of constant width (e.g., rectangular). In an embodiment, the stem 244b may be flat and may have other shapes, such as inwardly tapered, polygonal, etc. The stem 244b may have ridges 248 provided on the outer surface thereof. The stem 244b may also have one or more holes, openings or other apertures that can facilitate gripping of the stem. The stem 244b may have a pull strength of about 4 to about 6 lbf, such as about 4.5 to about 5.1 lbf, such as about 4.8 lbf.

Figure 21C:
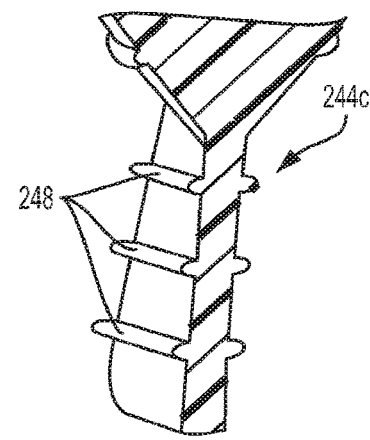

FIG. 21C shows a stem 244c similar to the stem 244b, however with the thickness of the stem 244b increased. The stem 244c may have ridges 248 provided on the outer surface thereof. As shown in FIGS. 21B and 21C, the thickness of the stem 244b, 244c may be selected to assist in grasping, insertion, removal, and repositioning of the vaginal insert devices 40, 100. The stem 244c may have the same or similar shape as stem 244b with an increased thickness. The stem 244c may have a pull strength of about 10 to about 12 lbf, such as about 11.07 lbf.

Figure 21D:
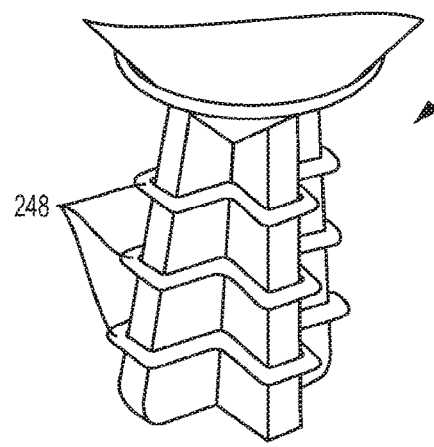

FIG. 21D shows a stem 244d that is generally cross-shaped in plan view or cross-section. The stem 244d may have ridges 248 which extend generally around the outer surface of the stem 244d. The stem 244d may be solid, that is, the stem 244d may be provided with no opening therein. Alternatively, the stem 244d may be substantially hollow (similar to stem 244a) with or without a ventilation opening therein. The stem 244d may taper or expand radially outward from the base of the upper portion to a distal end of the stem 244d. The stem 244d may be provided without the flare, that is, the stem may extend downward with constant cross-section such as shown in FIG. 21F. The stem 244d may have a pull strength of about 12 to about 14 lbf, such as about 12.8 lbf with the flare (FIG. 21D) and about 13.5 to about 15.5 lbf, such as about 14.41 bf without the flare (FIG. 21F).

Figure 21E:
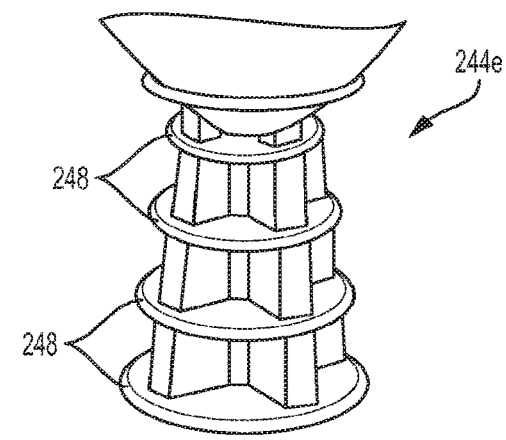
Figure 21F:
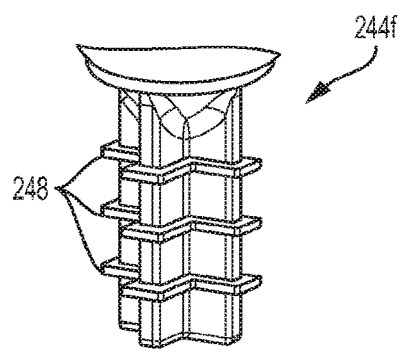

FIG. 21E shows a stem 244e that is generally conical in shape with ridges 248 provided circumferentially around an outer surface of the stem 244e. The stem 244a may be formed from a generally cross-shaped stem 244d (or 244f where the stem has a constant cross-section) with circular ridges provided around the outermost point of the cross-shaped portions of the stem 244e. The circular ridges may increase in diameter as the stem 244e increases in diameter. Alternatively, where the stem has a constant cross-section, the circular ridges may have constant diameters. The stem 244*e* may be solid, that is, the stem 244*e* may be provided with no opening there in. Alternatively, the stem 244*e* may be substantially hollow (similar to stem 244*a*) with or without a ventilation opening therein. The stem 244*e* may have a pull strength of about 13.3 to about 15.3, such as about 14.3 lbf.

FIG. 21F shows a stem 244*f* that is generally cross-shaped in plan view or cross-section. The stem 244*f* may have ridges 248 that extend generally around the outer surface or perimeter of the stem 244*f*. The stem 244*f* may be solid, that is, the stem 244*f* may be provided with no opening therein. Alternatively, the stem 244*f* may be substantially hollow (similar to stem 244*a*) with or without a ventilation opening therein. The stem 244*f* may be substantially uniform in cross-section along a length thereof. That is, the stem 244*f* may have the same outer dimension at a top and a bottom of the stem 244*f*.

The stems 44, 144, 244*a*-244*f* and 244*g* (FIG. 33C) may allow for a user to insert, remove, or adjust the device and/or administer medication or substances into the body or device and/or to reposition the vaginal insert device 40, 100. The stems 44, 144, 244*a*-244*g* may be selected based on comfort to the user once the device is inserted, ease of grip, ease of use, etc. The stem may assist in positioning of the device once inserted into the vagina. For example, the user may hold the stem and rotate the device within the vagina. A portion of the upper portion 142 near the stem 144 may also be held to assist in rotation of the device. In an embodiment, the device may be folded and/or compacted again to facilitate adjustment, with the stem still indicating the location and/or pressure applied to the intravaginal wall. The rotation of the device may adjust the pressure on the urethral sphincter, bladder neck, and/or rectum. Accordingly, the user may adjust the comfort level of the device by increasing or decreasing the pressure on the urethral sphincter or other organ wall through rotation of the stem. The stem and/or the ridges on the stem may be aligned with the ribs on the device such that when the stem is rotated, the rib is also rotated, placing greater pressure in a specific location.

FIGS. 22A-22E and FIG. 43 show a carrying case 300 for carrying the vaginal insert device of the present disclosure. The carrying case 300 may allow a user to store the vaginal insert device of the present disclosure (when not in use) in a clean and sanitary manner. The carrying case 300 may include a base 302 and a cover 304. The cover 304 may have a substantially cylindrical lower portion and a substantially semi-spherical upper portion. The base 302 may be scalloped on a bottom surface 306 (FIG. 22B) to allow for the carrying case 300 to rest flat on a surface, such as a table or counter. The base 302 may also be rounded. The bottom surface 306 may have shapes other than curves or scallops. For example, the surface 306 may have a rectangular shape, similar to turrets, or the surface 306 may be flat. The bottom of the base 302 may have a protrusion or indention that will hold an additional component such as a brush for sterilization or another sterilization technology. The base 302 may have a charging station attached. The base 302 may include a number of technologies such as infrared cleaning, recharging capabilities to recharge a certain component of the device, or communication device(s) to upload data to either a computer or mobile app. The base 302 may be made of one material, more than one material or a combination of materials. The base 302 may have one or more parts that work together or alone as well as may work together with the cover of the device.

Figure 22D:
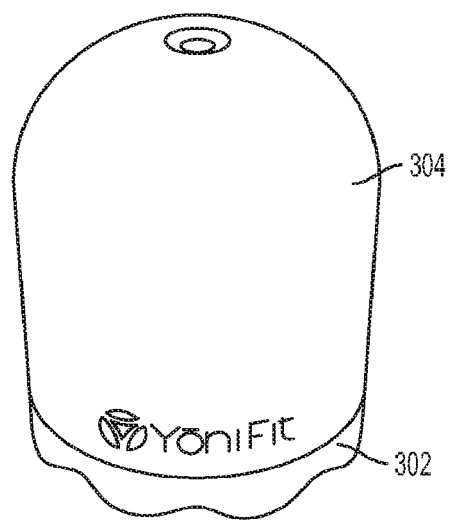
Figure 22E:
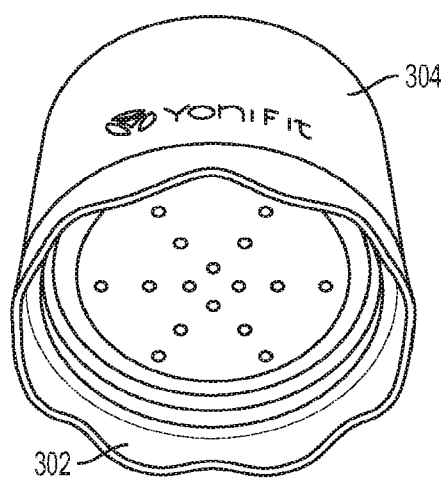
Figure 22F:
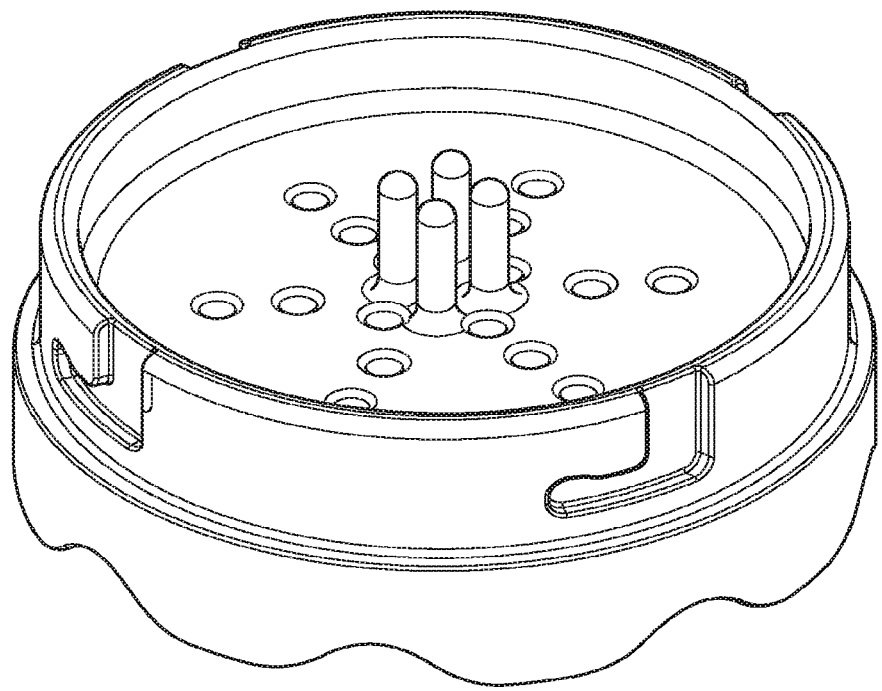
Figure 22G:
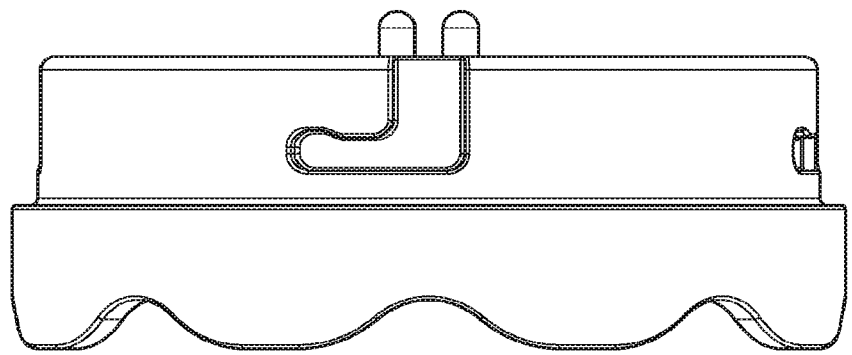
Figure 22H:
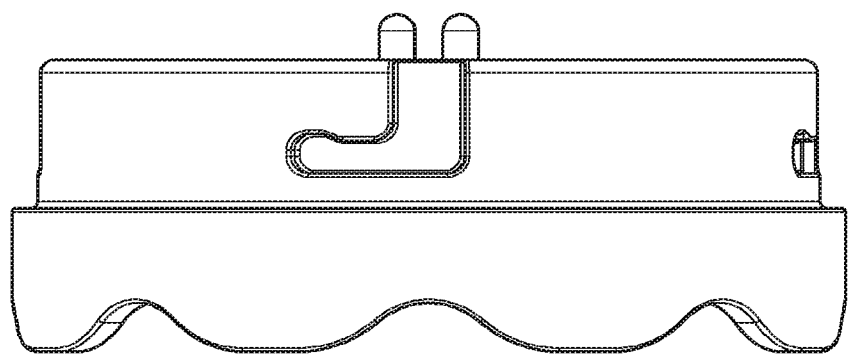
Figure 22I:
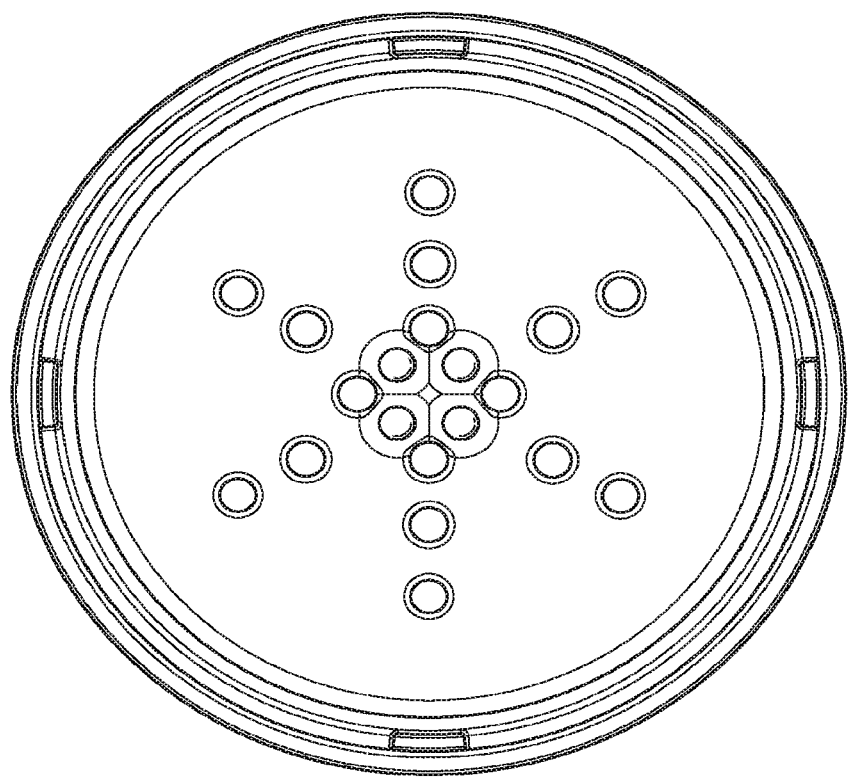
Figure 22J:
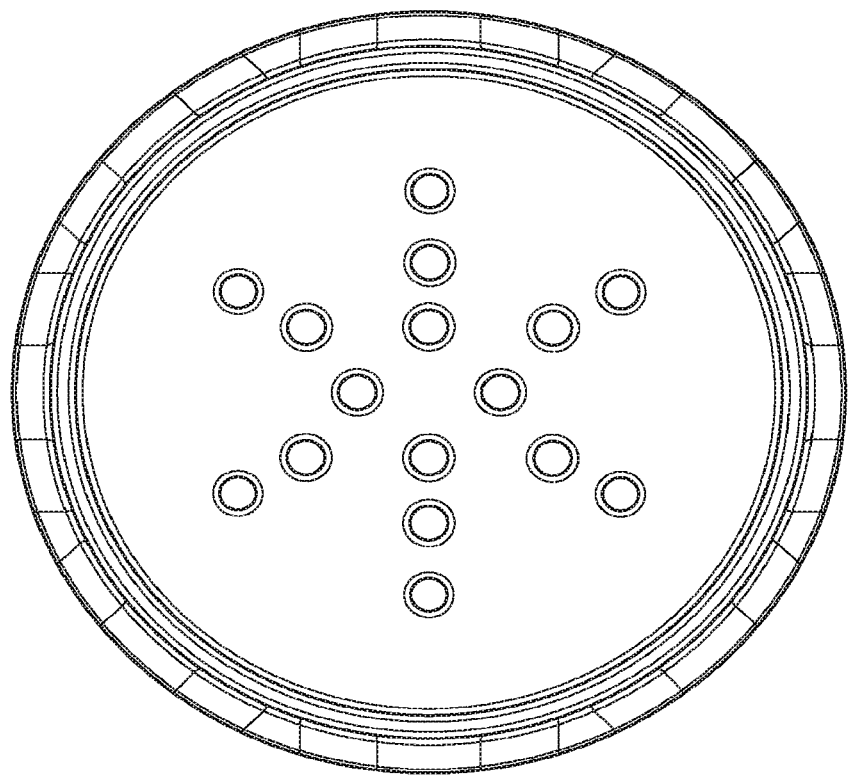
Figure 22K:
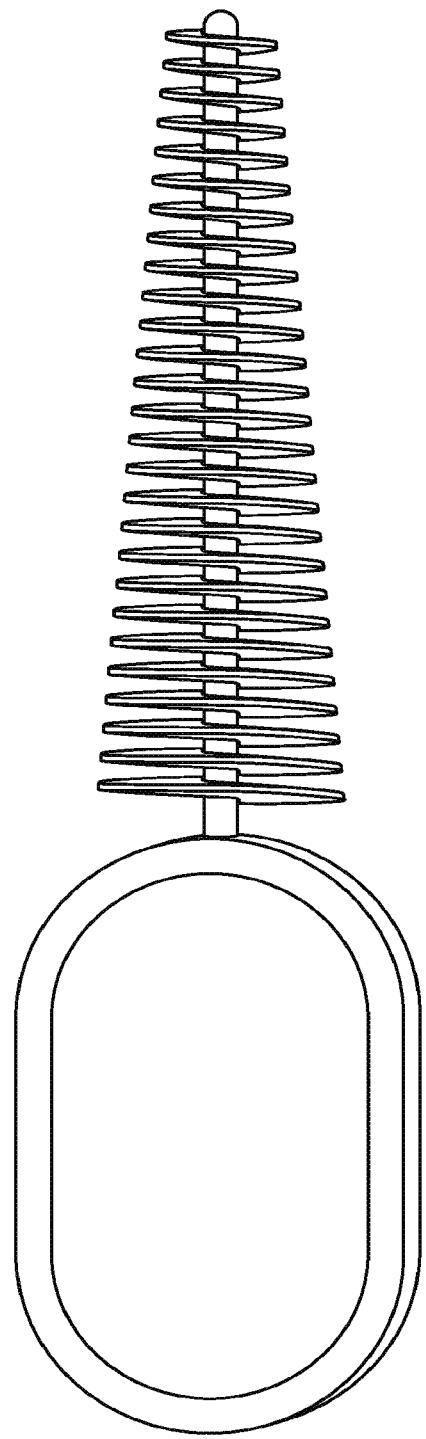
Figure 23:
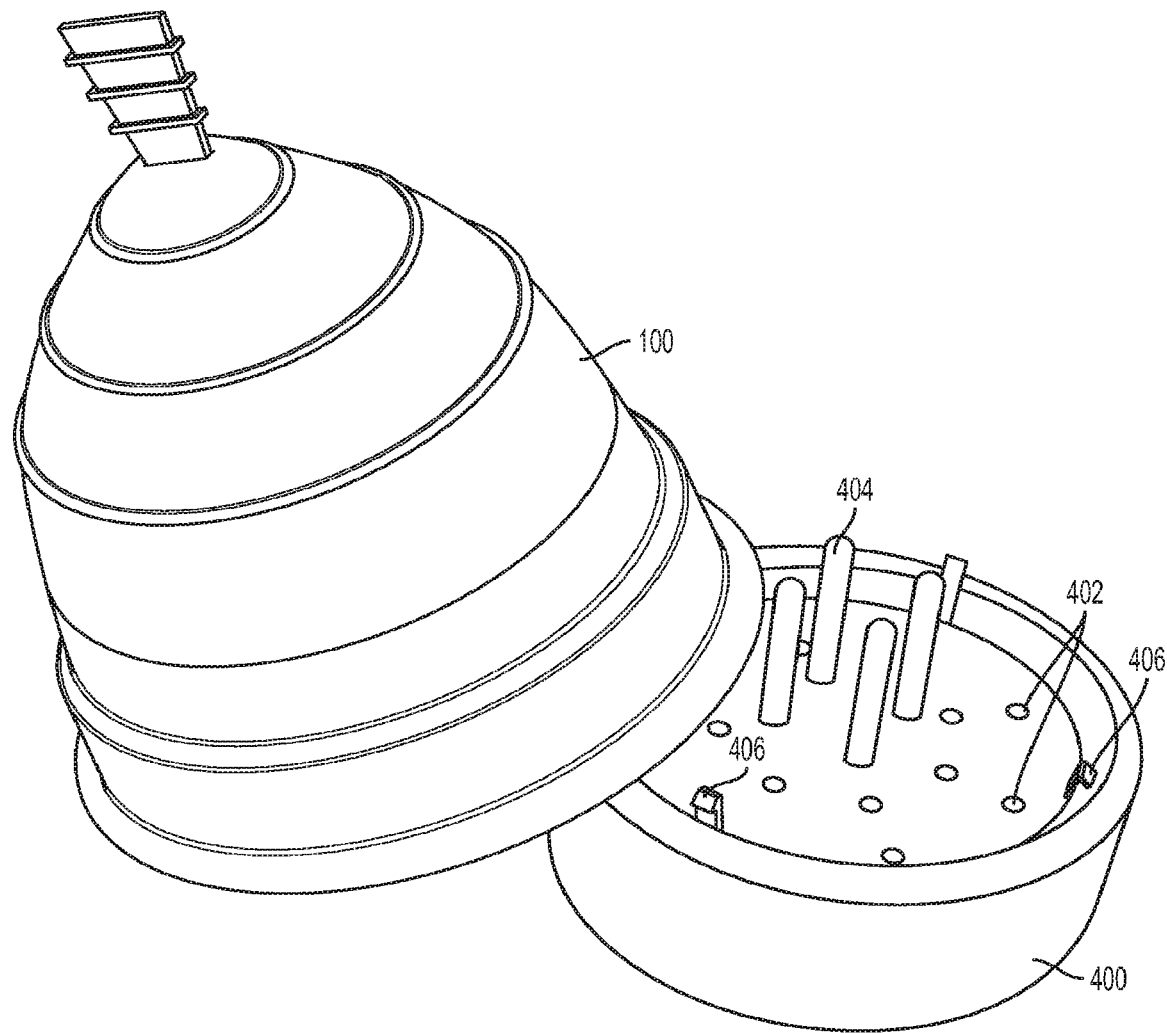
FIG. 23 illustrates a perspective view of a kit including a vaginal insert device and drying rack, in accordance with embodiments of the present disclosure.

As shown in FIGS. 22F-22J, the base 302 may be substantially cylindrical in shape to conform to the shape of the vaginal insert device and to hold it in place or allow for drying, cleaning or charging the device. 40, 100. With reference to FIG. 22C, the base 302 may have an upper cylindrical portion 308 having an uppermost surface 310. The vaginal insert device 40, 100 may be placed on top of the uppermost surface 310 such that the rim 46, 146 is flat on the uppermost surface 310. Once the vaginal insert device 40, 100 is placed on the base 302, the user may be place the cover 304 over the vaginal insert device 40, 100 and onto the surface 312 located on the base 302. The surface 312 and a cover surface 314 may mate and may snap, screw or otherwise fasten together once mated such that the cover 304 does not fall off and is only removed upon sufficient removal pressure from the user. In an embodiment, the surface 312 includes one or more (such as four regularly spaced) studs, numbs, or bumps that protrude outwardly from the surface and are sized and shaped to slide into a corresponding number of channels on the interior of the cover surface 314 to fasten the cover 304 to the base 302 (e.g., the L-shaped channels in FIGS. 22F-22H). The base 302 may provide a drying rack for the vaginal insert device 40, 100. The base 302 may be seen in FIGS. 22F-22J with the vaginal insert device 40, 100 removed. FIG. 22K depicts a brush for cleaning the vaginal insert device 40, 100. The brush may be included in a kit with the carrying case 300 and the carrying case 300 may include the drying rack 400 (FIG. 23). The container or carrying case 300 may be used for packaging shipping, and/or displaying the vaginal insert devices of the present disclosure.

Referring to FIG. 23, a drying rack 400 is depicted. The drying rack 400 may be included with the carrying case 300. The drying rack 400 may be the base 302, integrated with the base 302, coupled to the base 302, or may be a component of the base 302. The drying rack 400 may be substantially cylindrical in cross-section such that the vaginal insert device of the present disclosure fits, mates, or interfaces on the drying rack 400. The drying rack 400 may have a cylindrical base and may include one or more openings 402 and one or more protrusions 404. The openings 402 may allow for water or other liquid to drip off of the vaginal insert device 40, 100 through the drying rack 400 (or to be collected into the drying rack 400 and disposed of at a later time). The protrusions 404 may support the vaginal inset device of the present disclosure during drying, cleaning or charging. The protrusions 404 may be spaced such that when rib 180 is included, e.g., in the device 100, the protrusions 404 project into the open portions 158 (FIG. 18) and interface with the rib, for example to support either side of each member or rib portion 180*am* 180*b*, 180*c*, and 180*d*. For example, protrusions 404 may be spaced such that the members or rib portions may slide in between the protrusions 404 to releasably secure or anchor the device 100. In certain instances, the number of protrusions 404 equals the number of open portions 158 with each protrusion projecting into an open portion.

The drying, cleaning or charging rack 400 may include one or more latches, clips, fasteners, binders, protrusions, and/or indentions 406. The latches 406 may hook, slide or otherwise fasten onto the inner surface of the rim 46, 146 of the vaginal insert device of the present disclosure to support the device during drying charging or cleaning.

The carrying case 300 may be a self-sanitizing carrying case. That is, a user may place the vaginal insert device within the carrying case 300 such that the cover is secured to the base and the vaginal insert device is located within. The user may then initiate the carrying case 300 to sanitize, sterilize, or otherwise clean the vaginal insert device. The user may initiate the sterilizing of the vaginal insert device 40, 100 by pressing button and/or flipping switch, for example. The carrying case 300 may thus include a power connection, battery, power cord, or other power source to provide electricity to the carrying case. The carrying case 300 may also include a connection for wired or wireless connection to a mobile or internet connected device such that the user may remotely (e.g. through an app) operate the carrying case 300 to sanitize the vaginal insert device. In this manner, the user may not need to separately wash and dry the vaginal insert device. The user may simply place the vaginal insert device in the carrying case 300 and activate the device to sanitize or sterilize the vaginal insert device with no further action by the user. The sanitizing/sterilizing may occur with no added water, e.g., by air plasma, irradiation, ultraviolet light and/or ultrasonic means. In an embodiment, the sanitizing or sterilizing may be a water or solution. The vaginal insert device may be placed in the water or solution during a predetermined period of non-use (e.g., when a user is sleeping) for sanitizing and/or sterilizing. The user may then rinse the device after the predetermined period of time. The device may then be reinserted for the next use. In this manner, the user may have a predetermined schedule of cleansing, sanitizing and/or sterilizing the vaginal insert device (e.g., nightly, weekly, bi-weekly, etc.).

In an exemplary embodiment, the carrying case may be considered self-sanitizing/self-sterilizing, in that the case is configured to sanitize the vaginal insert device with no user intervention, except for, for example, the initiation by the user. In an exemplary embodiment, the carrying case may include air plasma technology for sanitizing and/or sterilizing the vaginal insert device. A carrying case 300 including air plasma technology may be plugged into a power source. The user may then activate (e.g. with a button or switch) the carrying case which may then use the air plasma technology to sterilize the vaginal insert device. In exemplary embodiments, the carrying case may include air plasma, ultraviolet light, ultrasonic, wet/dry heat and/or irradiation technology to sterilize and/or sanitize the vaginal insert device.

A kit may be provided for the vaginal insert device of the present disclosure. The kit may include one or more of the vaginal insert devices according to any of FIGS. 6-10, 16-20, and 27-38, a carrying case 300, and/or a drying rack 400. The kit may include devices of multiple sizes (for selection by the user and proper sizing and/or to accommodate changes to a user's body) or may include a single size, if the user has already determined the appropriate size. As the vaginal insert device may be provided in different sizes, the carrying case 300 and drying rack 400 may be sized to fit each individually sized vaginal insert device. Alternatively, the carrying case 300 may be sized to accommodate all sizes of the vaginal insert device. Accordingly, when a kit is provided, the kit may provide one or more of a vaginal insert device, carrying case 300, and drying rack 400 sized to complement one another. The kit may also include a cleanser for the vaginal insert device, and optionally a cleaning brush (e.g., the brush in FIG. 22K). The vaginal insert device may be reusable and the cleanser may allow for cleaning and/or sanitizing between uses. The kit may include towelettes to clean and/or sanitize the vaginal insert device and/or patient's hands. This may allow for insertion and/or removal of the vaginal insert device in a public facility, such as, for example, a public restroom. The kit may also include a brush or cleaning tool that may or may not fasten to the carrying case or drying rack for sanitation and cleaning purposes.

Figure 24:
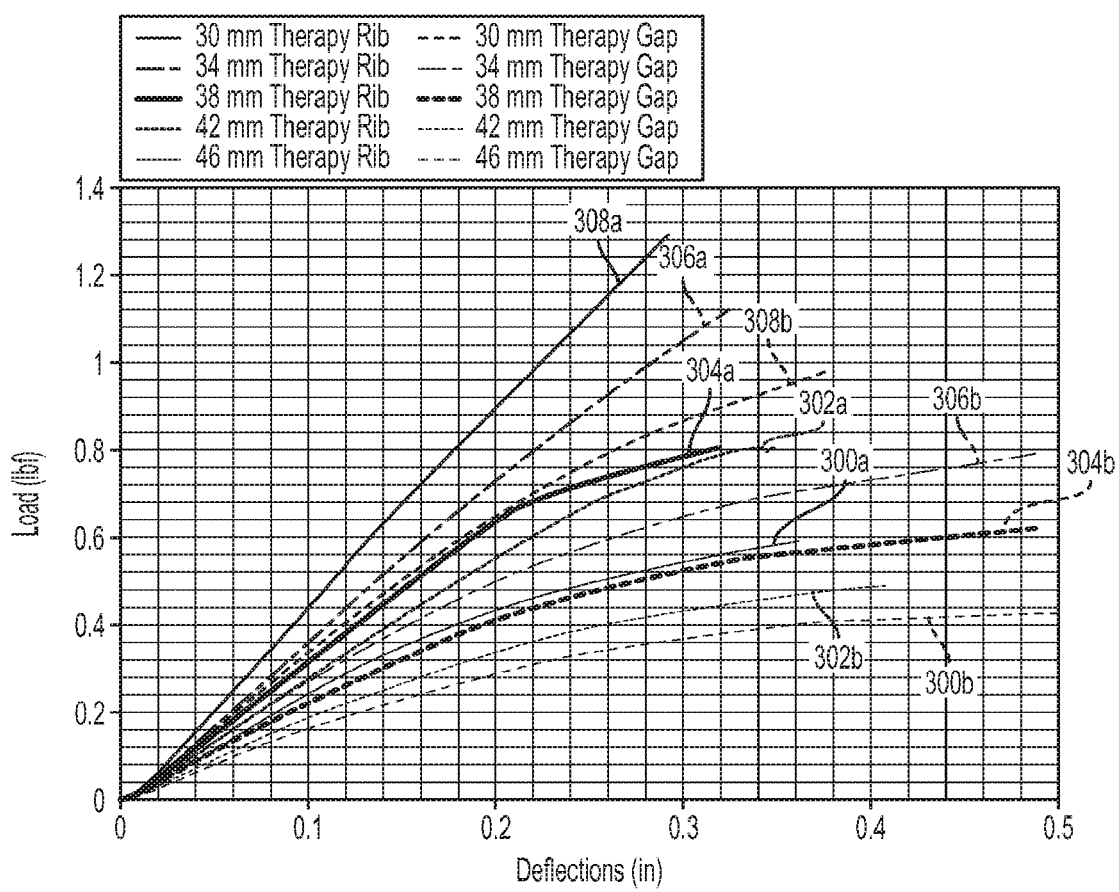
FIG. 24 illustrates a graph of forces placed on the urethral wall by the vaginal insert device, in accordance with embodiments of the present disclosure.

Referring to FIG. 24, a graphical representation of the therapy force of the vaginal insert devices according to the present disclosure, including any of FIGS. 16-20 and 27-38. The therapy force is the force applied to the bladder neck or the urethral sphincter through the intravaginal canal. That is, the force or pressure applied to the urethral sphincter. Lines 300, 302, 304, 306, and 308 align with Devices 2, 3, 4, 5, and 6, respectively, from Table 1. Lines 300*a*, 302*a*, 304*a*, 306*a*, and 308*a* depict the therapy force, or force applied to the urethral sphincter, bladder neck or rectum, at the rib. Lines 300*b*, 302*b*, 304*b*, 306*b*, and 308*b* depict the force applied at the gap or space between the rib.

Figure 25A:
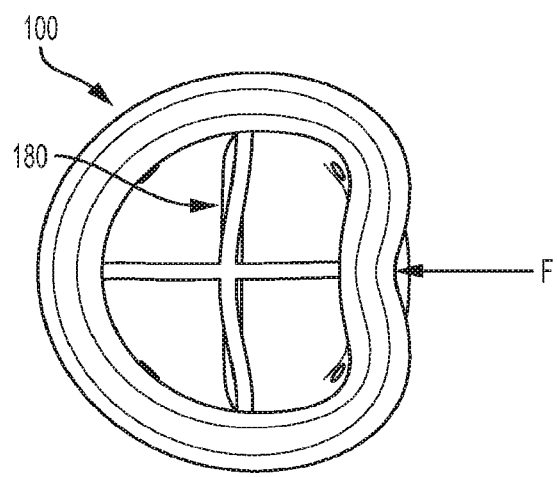
FIG. 25A illustrates force applied to a rib of a vaginal insert device, in accordance with embodiments of the present disclosure.

As shown in the graph of FIG. 24, the force (F-arrow in FIGS. 25A, 25B) applied to the urethral sphincter may be about 50% lower when the pressure is applied to a gap (FIG. 25B) as compared to pressure applied to a rib (FIG. 25A). Accordingly, in use, a patient may rotate the vaginal insert device such that the rib 180 is aligned with and places pressure on the urethral sphincter, bladder neck or rectum before high intensity activity, such as exercising, to support the organs during the activity. To facilitate such an alignment, the location of the rib or one or more rib sections or members may be correlated with the orientation of the stem (e.g., stem 144, 244*a*-244*g*, such as flat or two dimensional stems 144 and 244*b*-*c*), such that the plane created by the width of the stem is parallel or coextensive with the plane created by the rib or one or more rib portions or members (see, e.g., FIG. 18, coextensive plane created by rib 180 and stem 144 projecting from the page) or the plane created by the width of the stem is coextensive with a longitudinal axis of the device through which the rib passes (e.g., as shown in FIG. 17, the plane created by the width of the stem 144 parallel to the page and coextensive with the longitudinal axis or section line 18-18). Thus, by understanding the orientation of the stem through handling the stem, the user would also understand the orientation of the rib relative to the urethral sphincter, bladder neck or rectum when the device is inserted into the vaginal cavity.

The device may be rotated 45 degrees to achieve a 50% reduction in therapy force. When lower pressure on the urethral sphincter is desired, the patient may rotate the device such that the rib 180 is not aligned with the urethral sphincter, bladder neck or rectum and force is applied to a gap or offset between portions of the rib 180. Such alignment may be facilitated as described above. The rib may also expand or contract with rotation to apply more or less force to the urethral sphincter, bladder neck or rectum. The user may rotate the device with the stem.

Figure 25B:
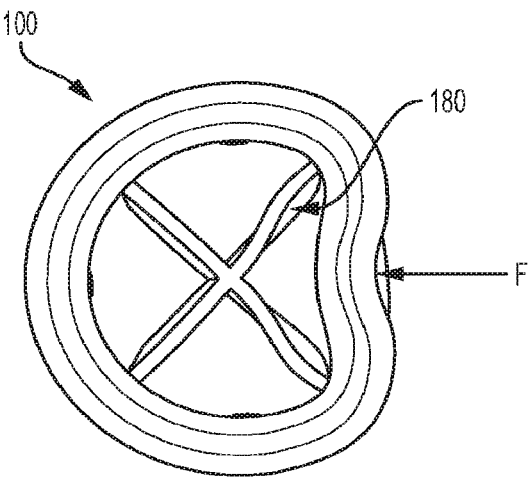
FIG. 25B illustrates force applied to a space offset from a rib of a vaginal insert device, in accordance with embodiments of the present disclosure.

Referring now to FIGS. 25A and 25B, force applied to the vaginal insert device of the present disclosure is shown. FIG. 25A depicts force, such as force at the urethral sphincter, as applied to a rib 180 of the device (e.g., Therapy Rib of FIG. 24). FIG. 25B depicts force, such as force at the urethral sphincter or rectum, as applied to a portion of the device located between portions of the rib 180 (e.g., Therapy Gap of FIG. 24). The force applied in FIG. 25B may be about 50% less than the force applied in FIG. 25A. As previously described, the force applied to the urethral sphincter, bladder neck or rectum may be less when the gap or space between the rib 180 is aligned with the urethral wall or rectum than when the rib 180 is aligned with the urethral wall, bladder neck or rectum. Thus, the force applied by the vaginal insert device of the present disclosure on the bladder neck urethral sphincter and/or rectum is adjustable and selectively adjustable.

Although previously described as reducing or eliminating urinary incontinence, the vaginal insert device of the present disclosure may be placed in the vagina such that the device 40, 100 places pressure on a bowel or colon wall. The device may be rotated to adjust pressure on the bowel or colon wall as previously described. Where rib 180 is included in the vaginal insert device, the rib may provide pressure on the rectum and/or bowel or colon wall to effectively reduce manage, treat, prevent and/or eliminate fecal incontinence. Thus, the vaginal insert device may be placed in the vagina to place pressure on the rectum to prevent fecal incontinence or a prolapsed rectum or to prevent further displacement of the rectum. The insert may also be placed in the anus to prevent, manage, reduce, treat and/or eliminate fecal incontinence.

Figure 26:
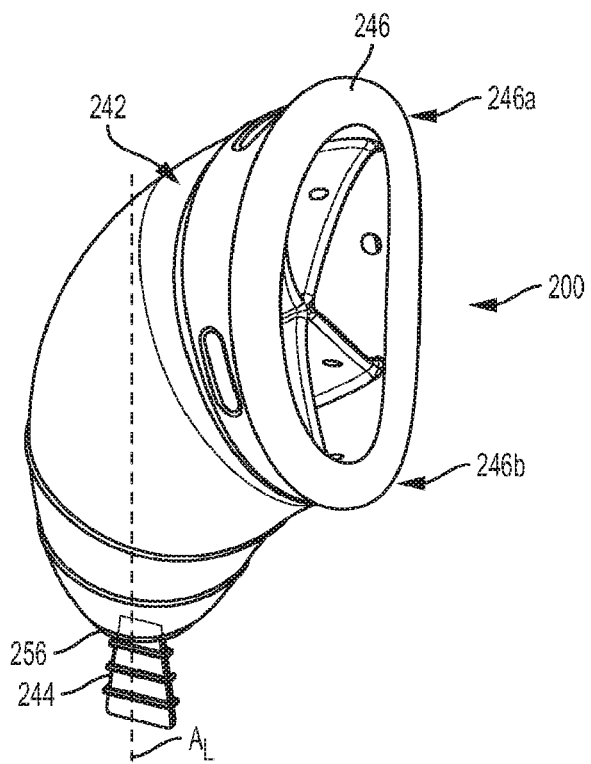
FIG. 26 illustrates a vaginal insert device, in accordance with embodiments of the present disclosure.

Referring to FIG. 26, a vaginal insert device 200 is shown. The vaginal insert device 200 may be similar to the vaginal insert devices 40, 100. The vaginal insert device 200 may have a rim 246. When the rim 246 is in included, the rim 246 may be similar to the rim 46, 146. However, the plane of the rim 246 may be substantially vertical, i.e., parallel or angled with respect to a vertical axis A through the stem 244 and the base 256 of the body 242. For instance, the device 200 may have a curved horn shape, with the rim 246 being analogous to the widest end portion of the horn and the base 256 being analogous to the narrow tip portion of the horn. The rim 246 may have a first portion 246a which is offset vertically from a second portion 246b. The first portion 246a may be higher or spaced at a location from the lower portion 246b. The first portion may also be a different thickness, durometer, density and durability as that of the lower portion or opposing side. The rim may be a different shape than the opposing side. The rim may be made of one, more than one or a combination of materials and parts. The rim may expand or retract to place the correct amount of force at the correct location in the body for the patient. The rim may be semi-permeable to allow for fluid, gas, lubrication or medication to pass through.

The rim 246, if present, may be tilted or angled as compared to the rim 46, 146 of the vaginal insert device 40, 100. The bladder neck may be at a higher location in the vagina than the rectal and/or bowl wall. Accordingly, when placed in the vagina, the vaginal insert device 200 may be placed such that the second portion 246b or lower side places pressure on the rectal wall. The higher wall may place pressure on the urethral wall. The tilted rim 246 may allow for the pressure applied to the rectal or bowel wall to be less than the pressure applied with a substantially horizontal rim, such as the rims 46, 146. Alternatively, the vaginal insert device 40, 100 may be shortened to accommodate the lower location of the rectal/bowel wall in the vagina. Although described with respect to a bowel wall, the height of the rim and/or angle of the rim may be selected to apply pressure to other parts of the vaginal wall.

The vaginal insert device 200 may place pressure on the bowel wall to eliminate and/or reduce fecal incontinence. The vaginal insert device 200 may prevent, eliminate, or reduce rectal prolapse (e.g. rectocele). The vaginal insert device 200 may treat, manage, prevent, eliminate, or reduce urinary and fecal incontinence due to the pressure placed on both the urethral wall and the bowel wall. As shown and described, the optional rim 246 (and/or rim 46, 146) may be lopsided, titled, or otherwise angled to place pressure at different locations in the vaginal canal based on anatomy and type of incontinence and/or prolapse to be prevented or reduced. The first portion may also be a different thickness, durometer, density and durability as that of the lower portion or opposing side. The rim may be a different shape than the opposing side. The rim may be made of one, more than one or a combination of materials and parts. The rim may expand or retract to place the correct amount of force at the correct location in the body for the patient. The rim may be semi-permeable to allow for fluid, gas, lubrication or medication to pass through.

Figure 27A:
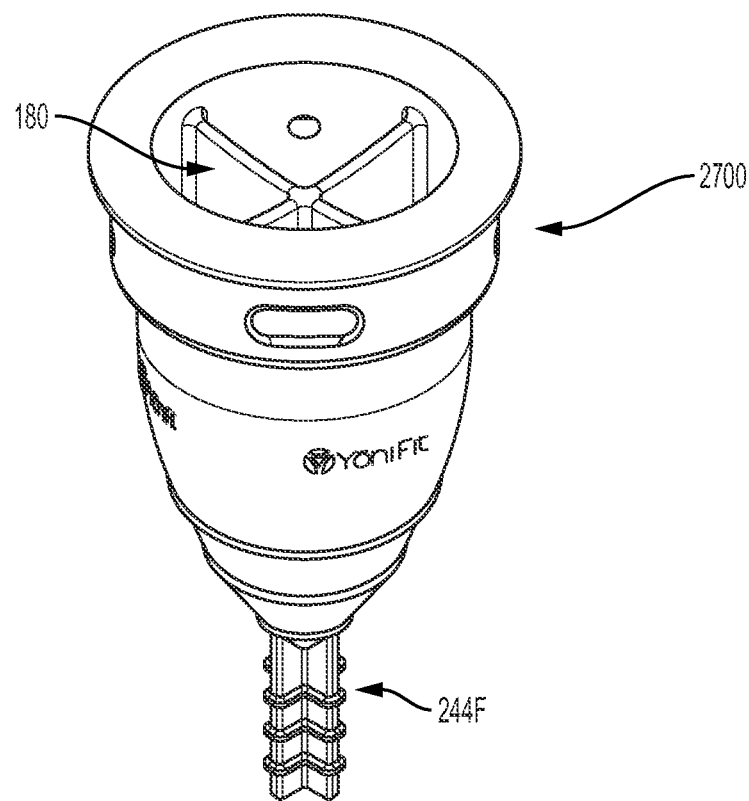
FIG. 27A illustrates a perspective view of a vaginal insert device, according to an embodiment of the present disclosure.

Referring to FIGS. 27A-27H, a vaginal insert device 2700 is shown. The vaginal insert device 2700 may be similar to the vaginal insert device 100 except that the stem 244F may be the cross-shaped stem 244f of FIG. 21F (although the stem also may be one of the stems 244a-244e, including the two dimensional stems 144 and 244b-c). Accordingly, any of the previously described variations, uses, modifications, or features described with respect to any of the vaginal insert devices herein may be used, applied, or modified to the vaginal insert device 2700. For example, any of the variations, uses, modifications, or features with respect to the ribs 180, shape, ventilation openings, etc. may be provided on the vaginal insert device 2700. Additionally, any of the uses or accessories (e.g., the carrying case) may apply to the vaginal insert device 2700 as previously described. Referring to FIG. 27A, a perspective view of the vaginal insert device 2700 is shown with the rib 180 spaced a distance below the top surface of the device 2700. The upper portion, rim, ribs, ventilation openings, methods of insertion, rotation, adjusting pressure, use, and any other features or embodiments described herein may be presented with the vaginal insert device 2700.

Figure 27B:
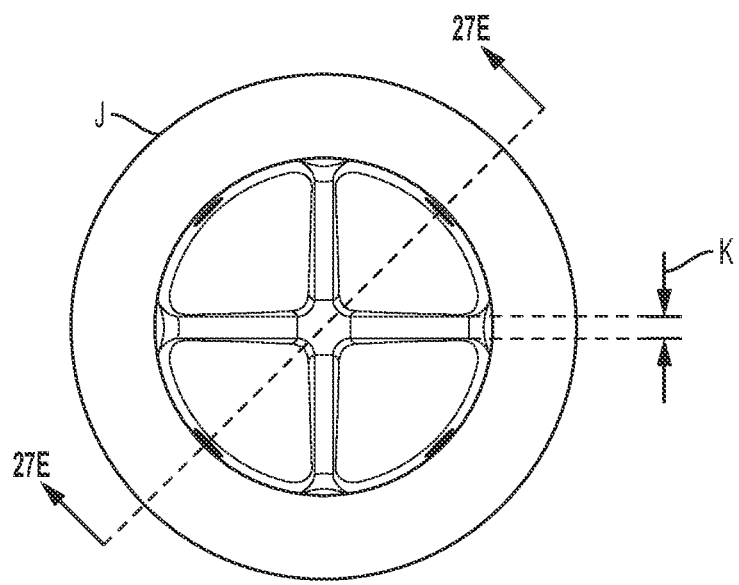
FIG. 27B illustrates a top view of the vaginal insert device of FIG. 27A, according to an embodiment of the present disclosure.

Referring to FIG. 27B, a top view of the vaginal insert device 2700 is shown. The vaginal insert device 2700 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 30 mm. The vaginal insert device 2700 may also have a width K of a rib 180 that is about 1 to about 1.6 mm, such as about 1.3 mm. Each of the four portions of the cross-shaped rib may have the dimension K. Referring to FIG. 27C, a side view of the vaginal insert device 2700 is shown. The ridges and optional logo may be spaced equidistant along the outer surface of the upper portion of the vaginal insert device 2700, as described with respect to previous embodiments. Referring to FIG. 27D, a side view rotated 90 degrees from the view of FIG. 27C is depicted. The ridges on the stem 244F may be spaced for each other. The lowermost ridge may be spaced a distance Z of about 2.7 to about 3.1 mm, such as about 2.9 mm from the bottom of the vaginal insert device 2700. The middle ridge may be spaced a distance Y of about 3.1 to about 3.5, such as about 3.3 mm from the lowermost ridge. The uppermost ridge may be spaced a distance X of about 3.1 to about 3.5, such as about 3.3 mm from the middle ridge.

Figure 27E:
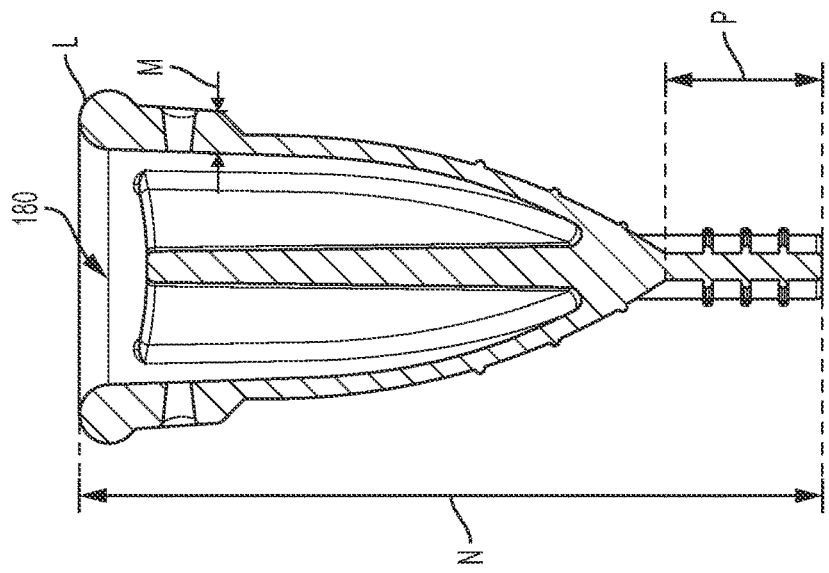
FIG. 27E illustrates a cross-sectional view of the vaginal insert device of FIG. 27A across the section line 27E-27E of FIG. 27B, according to an embodiment of the present disclosure.
Figure 27D:
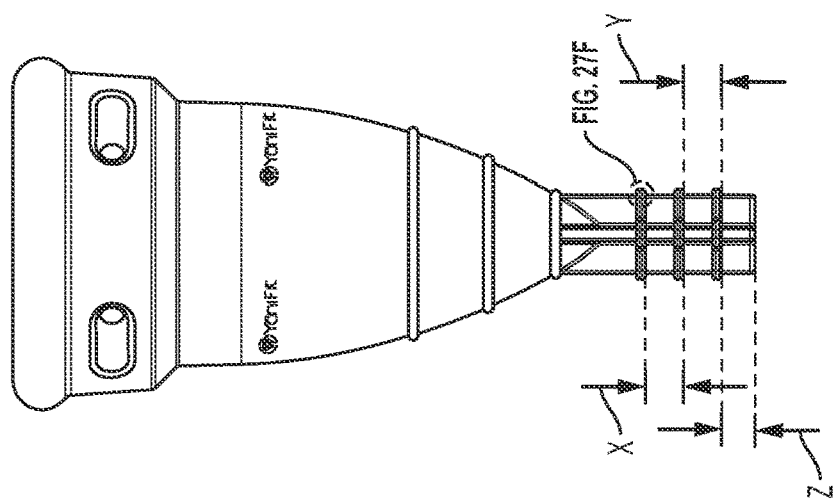
FIG. 27D illustrates a side view, rotated 90 degrees from the side view of FIG. 27C, of the vaginal insert device of FIG. 27A, according to an embodiment of the present disclosure.
Figure 27C:
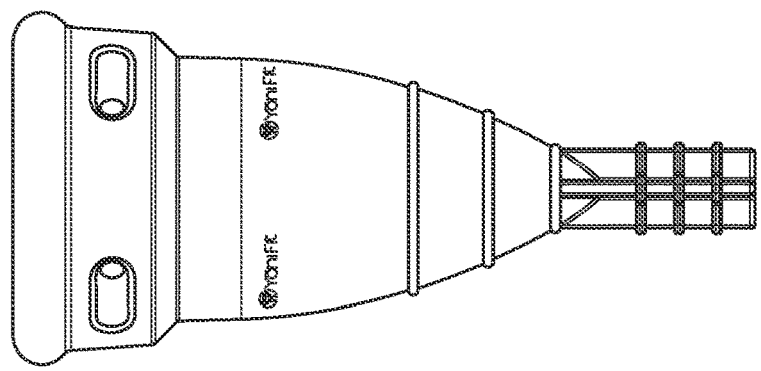
FIG. 27C illustrates a side view of the vaginal insert device of FIG. 27A, according to an embodiment of the present disclosure.

Referring to FIG. 27E, a side cross-sectional view of the vaginal insert device 2700 is depicted. The distance from the bottom of the device to the base of the upper portion may be a distance P of about 13 to about 14 mm, such as about 13.3 to about 13.7 mm, for example about 13.5 mm. The vaginal insert device 2700 may have a length N of about 50 to about 76 mm, such as about 55 to about 71 mm, for example about 57, 58, 59, 60, 61, 62, 63, 64, 65, 66, 67, 68, or 69 mm, including about 58 or about 63 mm. A width M of the enlarged portion may be about 3.5 to about 4.1 mm, such as about 3.8 mm. A width L of the rim may be about 4 to about 6 mm, such as about 5 mm.

Figure 27H:
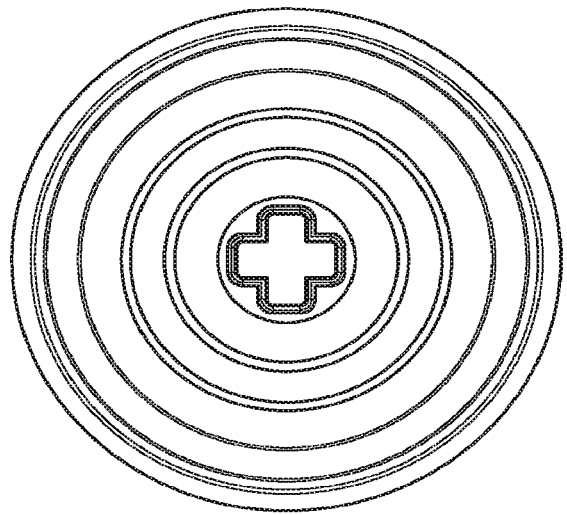
FIG. 27H illustrates a bottom view of the vaginal insert device of FIG. 27A, according to an embodiment of the present disclosure.
Figure 27G:
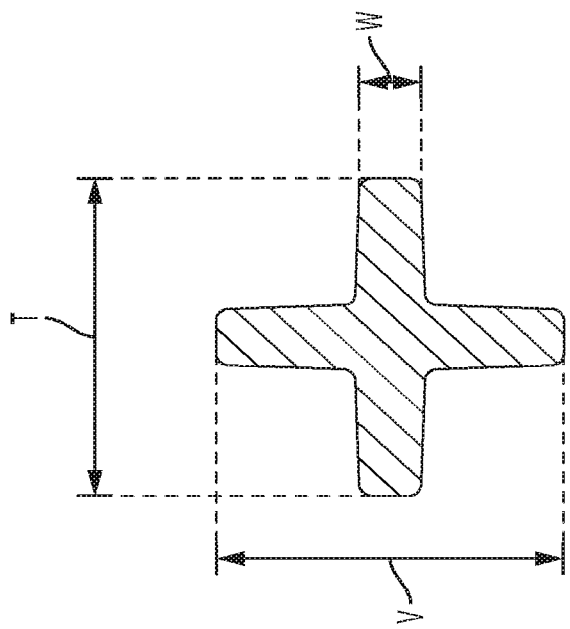
FIG. 27G illustrates a plan view of a stem of the vaginal insert device of FIG. 27A, according to an embodiment of the present disclosure.
Figure 27F:
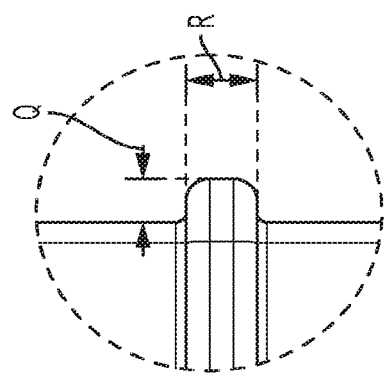
FIG. 27F illustrates a detail view of the vaginal insert device of FIG. 27A within the section of FIG. 27F in FIG. 27D, according to an embodiment of the present disclosure.

Referring to FIG. 27F, a detailed view of the ridges on the stem 244F is depicted. Each of the ridges may extend from the stem 244F by a distance Q of about 0.4 to about 0.6 mm, such as about 0.5 mm. Each of the ridges may have a thickness R of about 0.7 to about 0.9 mm, such as about 0.8 mm. Referring to FIG. 27G, a cross-sectional view of the stem 244F is depicted. The stem 244F may have an overall width T of about 6.6 to about 7 mm, such as about 6.8 mm and an overall width C of about 6.6 to about 7 mm, such as about 6.8 mm. Each leg of the cross-shaped stem 244F may have a width W of about 1.3 to about 1.5 mm, such as about 1.4 mm. Referring to FIG. 27H, a bottom view of the device 2700 is depicted.

Figure 28A:
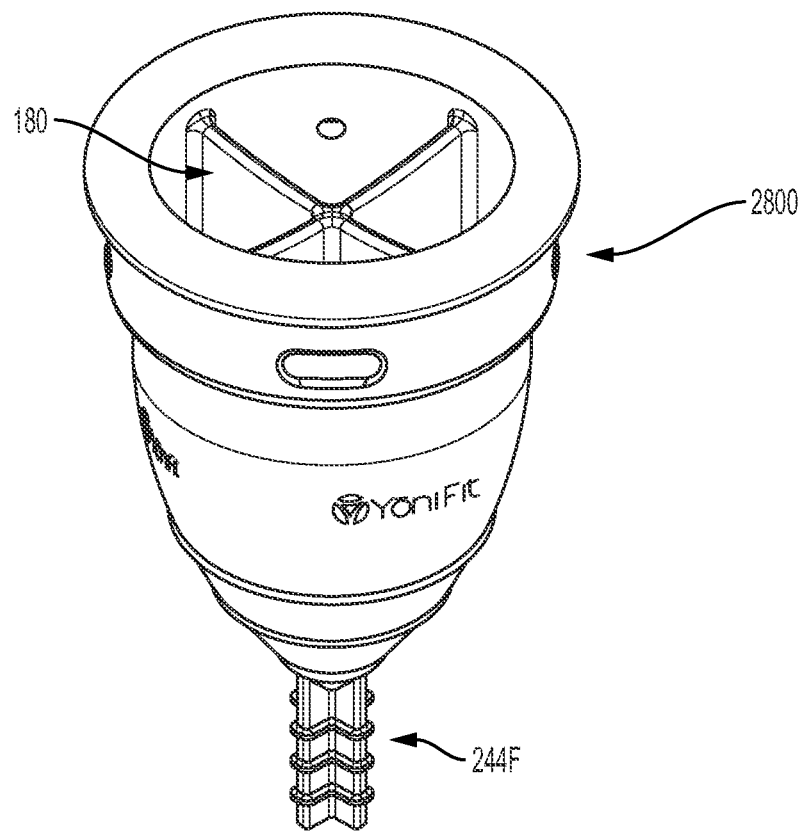
FIGS. 28A-28H illustrate a vaginal insert device, according to an embodiment of the present disclosure.

Referring to FIGS. 28A-28H, a vaginal insert device 2800 is shown. The vaginal insert device 2800 may similar to the vaginal insert device 100 except that the stem 244F may be the cross-shaped stem 244f of FIG. 21F (although the stem also may be one of the stems 244a-244e, including the two dimensional stems 144 and 244b-c). The vaginal insert device 2800 may be similar to the vaginal insert device 2700 except the sizing may be different. Accordingly, any of the previously described variations, uses, modifications, or features described with respect to any of the vaginal insert devices herein may be used, applied, or modified to the vaginal insert device 2800. For example, any of the variations, uses, modifications, or features with respect to the ribs 180, shape, ventilation openings, etc. may be provided on the vaginal insert device 2800. Additionally, any of the uses or accessories (e.g., the carrying case) may apply to the vaginal insert device 2800 as previously described. Referring to FIG. 28A, a perspective view of the vaginal insert device 2800 is shown with the rib 180 spaced a distance below the top surface of the device 2800. The upper portion, rim, ribs, ventilation openings, methods of insertion, rotation, adjusting pressure, use, and any other features or embodiments described herein may be presented with the vaginal insert device 2800.

Figure 28B:
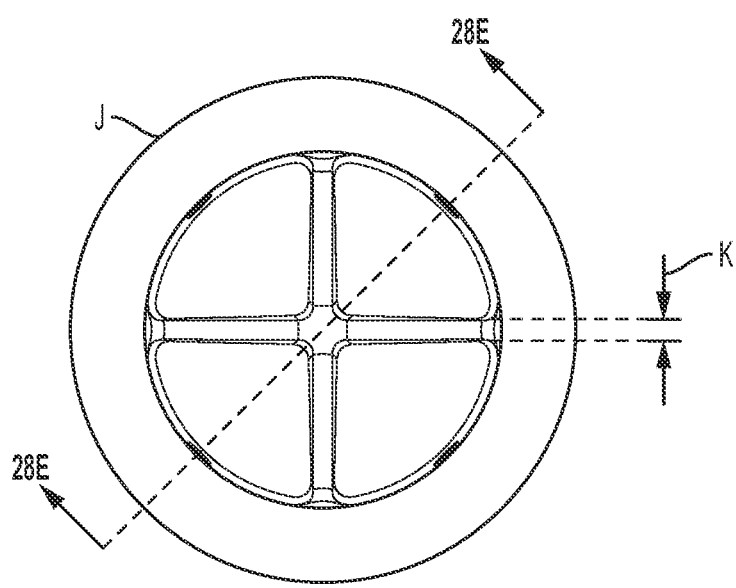

Referring to FIG. 28B, a top view of the vaginal insert device 2800 is shown. The vaginal insert device 2800 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 34 mm. The vaginal insert device 2700 may also have a width K of a rib 180 that is about 1 to about 1.6 mm, such as about 1.3 mm. Each of the four portions of the cross-shaped rib may have the dimension K. Referring to FIG. 28C, a side view of the vaginal insert device 2800 is shown. The ridges and optional logo may be spaced equidistant along the outer surface of the upper portion of the vaginal insert device 2800, as described with respect to previous embodiments. Referring to FIG. 28D, a side view rotated 90 degrees from the view of FIG. 28C is depicted. The ridges on the stem 244F may be spaced for each other. The lowermost ridge may be spaced a distance Z of about 2.7 to about 3.1 mm, such as about 2.9 mm from the bottom of the vaginal insert device 2800. The middle ridge may be spaced a distance Y of about 3.1 to about 3.5, such as about 3.3 mm from the lowermost ridge. The uppermost ridge may be spaced a distance X of about 3.1 to about 3.5, such as about 3.3 mm from the middle ridge.

Figure 28E:
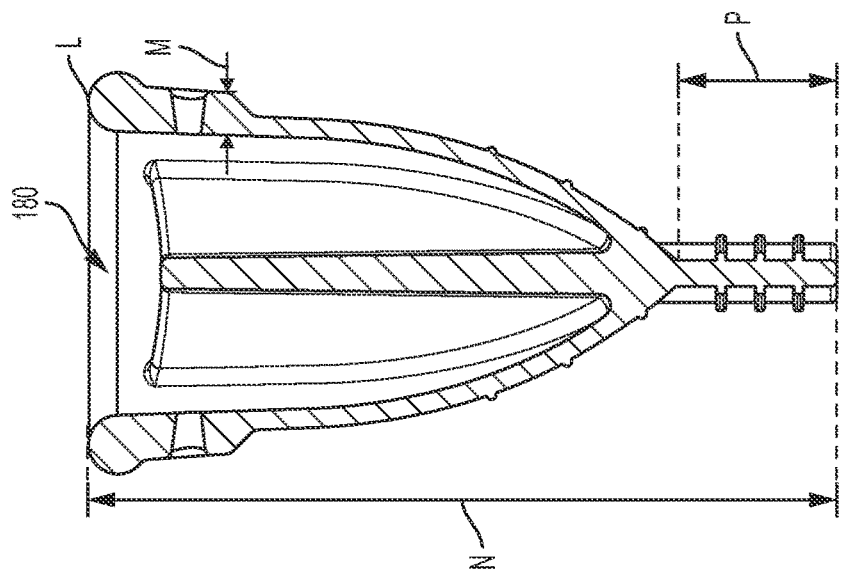
Figure 28D:
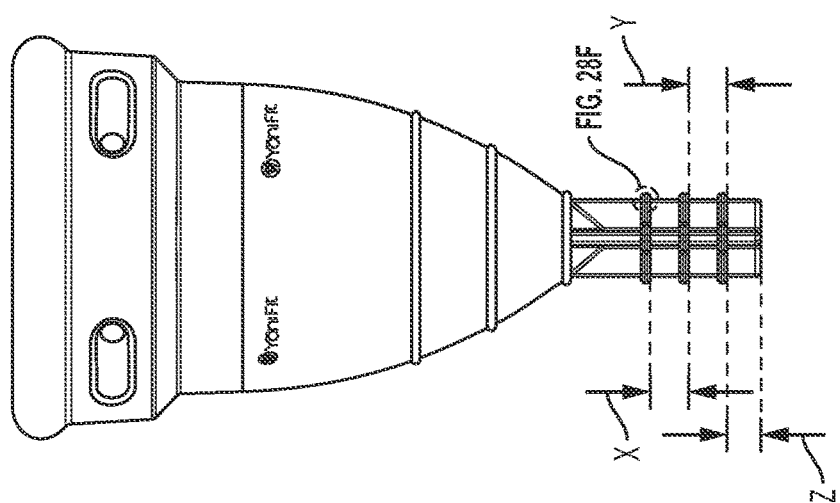
Figure 28C:
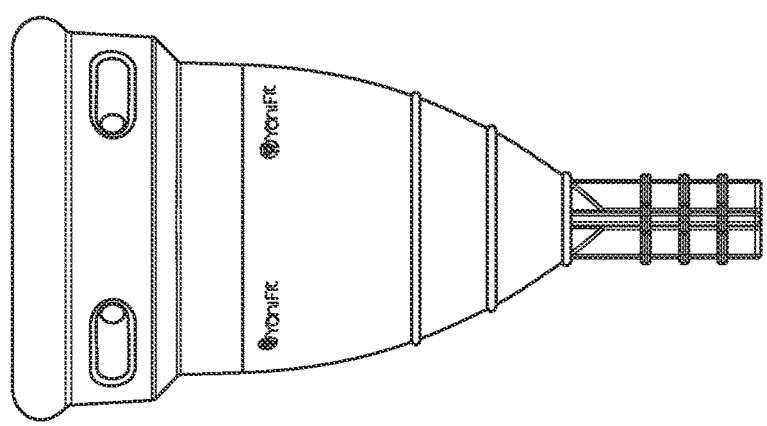

Referring to FIG. 28E, a side cross-sectional view of the vaginal insert device 2800 is depicted. The distance from the bottom of the device to the base of the upper portion may be a distance P of about 13 to about 14 mm, such as about 13.3 to about 13.7 mm, for example about 13.5 mm. The vaginal insert device 2800 may have a length N of about 50 to about 76 mm, such as about 55 to about 71 mm, for example about 57, 58, 59, 60, 61, 62, 63, 64, 65, 66, 67, 68, or 69 mm, including about 58 or about 63 mm. A width M of the enlarged portion may be about 3.5 to about 4.1 mm, such as about 3.8 mm. A width L of the rim may be about 4 to about 6 mm, such as about 5 mm.

Figure 28H:
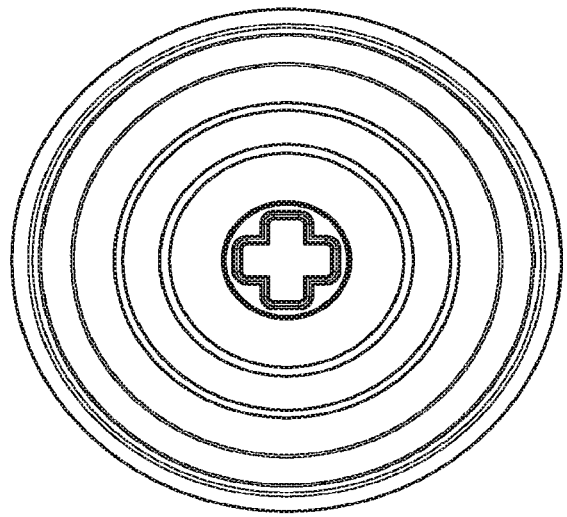
Figure 28G:
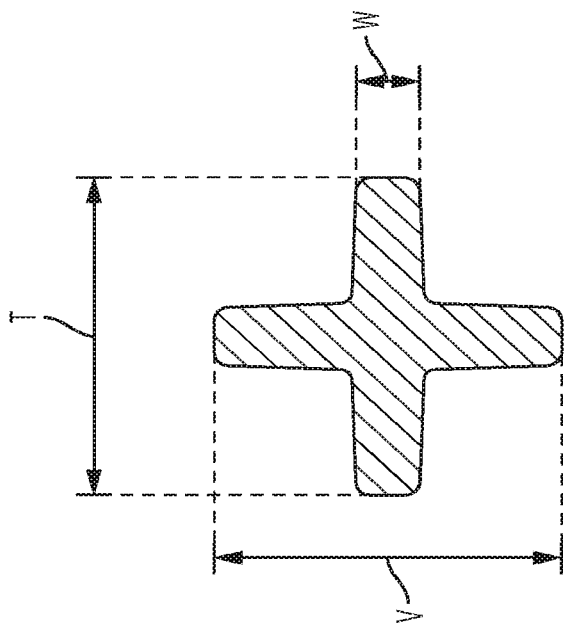
Figure 28F:
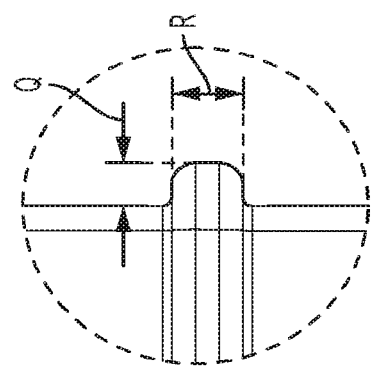

Referring to FIG. 28F, a detailed view of the ridges on the stem 244F is depicted. Each of the ridges may extend from the stem 244F by a distance Q of about 0.4 to about 0.6 mm, such as about 0.5 mm. Each of the ridges may have a thickness R of about 0.7 to about 0.9 mm, such as about 0.8 mm. Referring to FIG. 28G, a cross-sectional view of the stem 244F is depicted. The stem 244F may have an overall width T of about 6.6 to about 7 mm, such as about 6.8 mm and an overall width C of about 6.6 to about 7 mm, such as about 6.8 mm. Each leg of the cross-shaped stem 244F may have a width W of about 1.3 to about 1.5 mm, such as about 1.4 mm. Referring to FIG. 28H, a bottom view of the device 2800 is depicted.

Figure 29A:
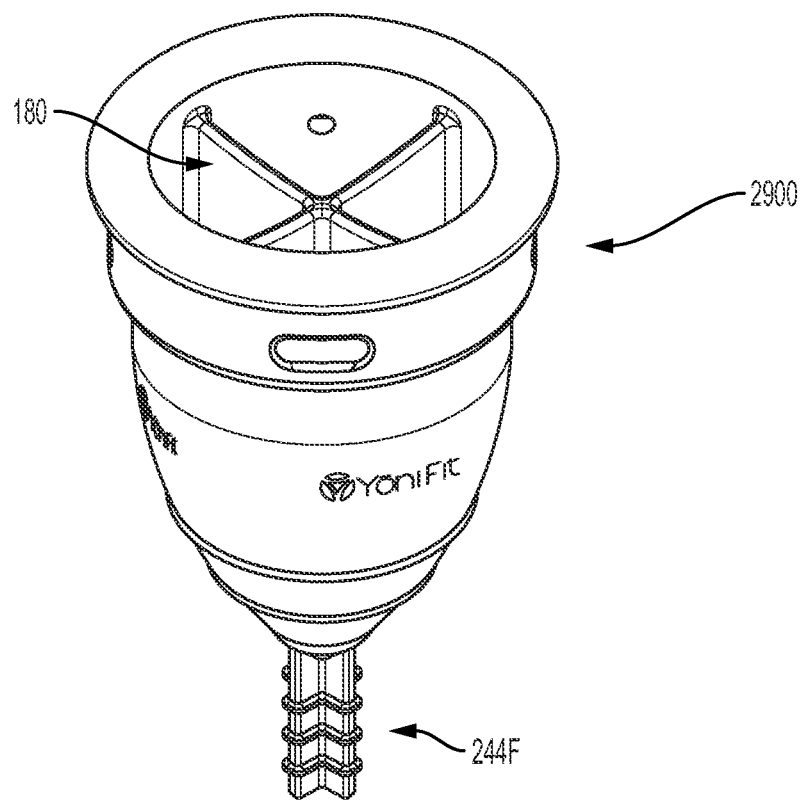
FIGS. 29A-29H illustrate a vaginal insert device, according to an embodiment of the present disclosure.

Referring to FIGS. 29A-29H, a vaginal insert device 2900 is shown. The vaginal insert device 2900 may be similar to the vaginal insert device 100 except that the stem 244F may be the cross-shaped stem 244f of FIG. 21F (although the stem also may be one of the stems 244a-244e, including the two dimensional stems 144 and 244b-c). The vaginal insert device 2900 may be similar to the vaginal insert devices 2700, 2800 except the sizing may be different. Accordingly, any of the previously described variations, uses, modifications, or features described with respect to any of the vaginal insert devices herein may be used, applied, or modified to the vaginal insert device 2900. For example, any of the variations, uses, modifications, or features with respect to the ribs 180, shape, ventilation openings, etc. may be provided on the vaginal insert device 2900. Additionally, any of the uses or accessories (e.g., the carrying case) may apply to the vaginal insert device 2900 as previously described. Referring to FIG. 29A, a perspective view of the vaginal insert device 2900 is shown with the rib 180 spaced a distance below the top surface of the device 2900. The upper portion, rim, ribs, ventilation openings, methods of insertion, rotation, adjusting pressure, use, and any other features or embodiments described herein may be presented with the vaginal insert device 2900.

Figure 29B:
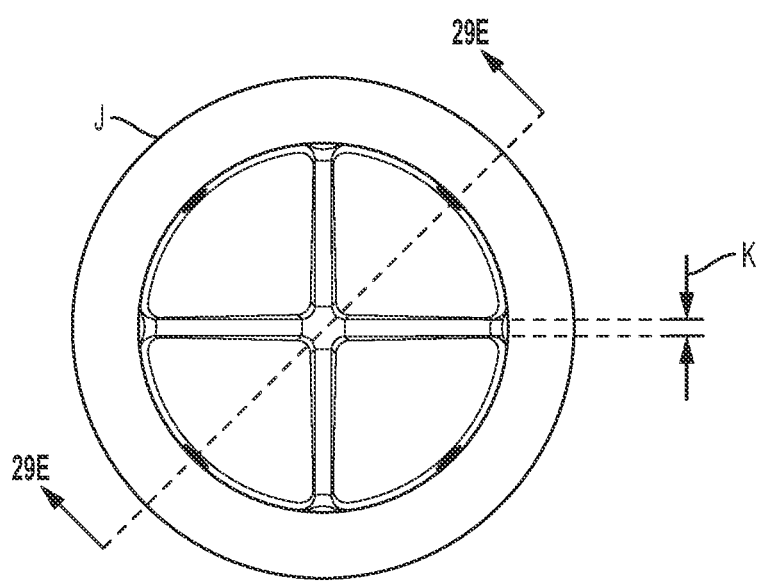

Referring to FIG. 29B, a top view of the vaginal insert device 2900 is shown. The vaginal insert device 2900 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 38 mm. The vaginal insert device 2700 may also have a width K of a rib 180 that is about 1 to about 1.6 mm, such as about 1.3 mm. Each of the four portions of the cross-shaped rib may have the dimension K. Referring to FIG. 29C, a side view of the vaginal insert device 2900 is shown. The ridges and optional logo may be spaced equidistant along the outer surface of the upper portion of the vaginal insert device 2900, as described with respect to previous embodiments. Referring to FIG. 29D, a side view rotated 90 degrees from the view of FIG. 29C is depicted. The ridges on the stem 244F may be spaced for each other. The lowermost ridge may be spaced a distance Z of about 2.7 to about 3.1 mm, such as about 2.9 mm from the bottom of the vaginal insert device 2900. The middle ridge may be spaced a distance Y of about 3.1 to about 3.5, such as about 3.3 mm from the lowermost ridge. The uppermost ridge may be spaced a distance X of about 3.1 to about 3.5, such as about 3.3 mm from the middle ridge.

Figure 29E:
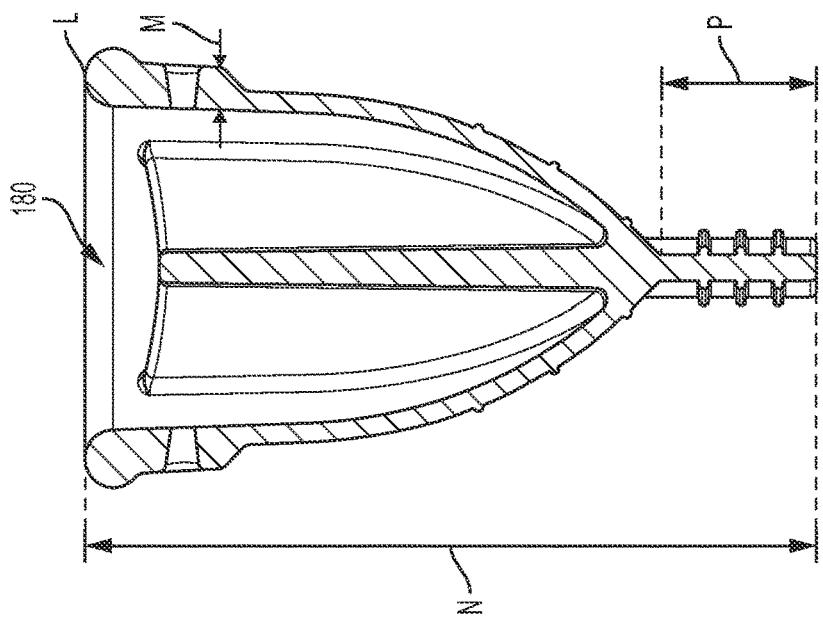
Figure 29D:
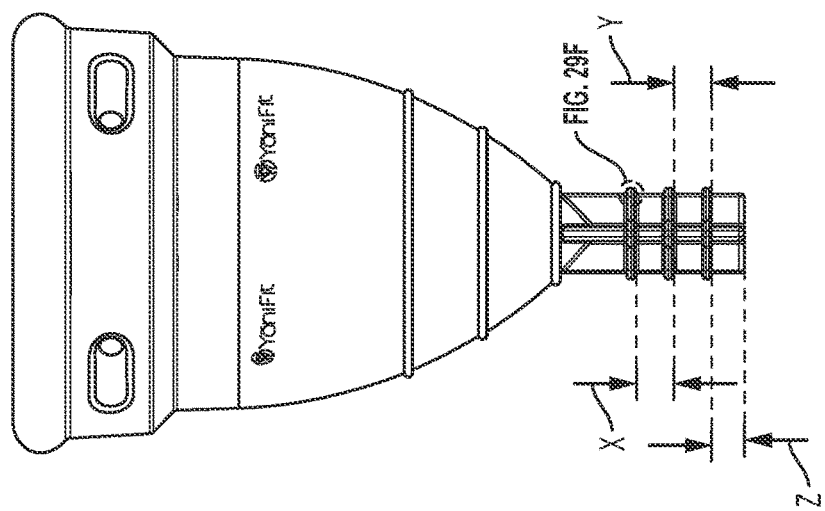
Figure 29C:
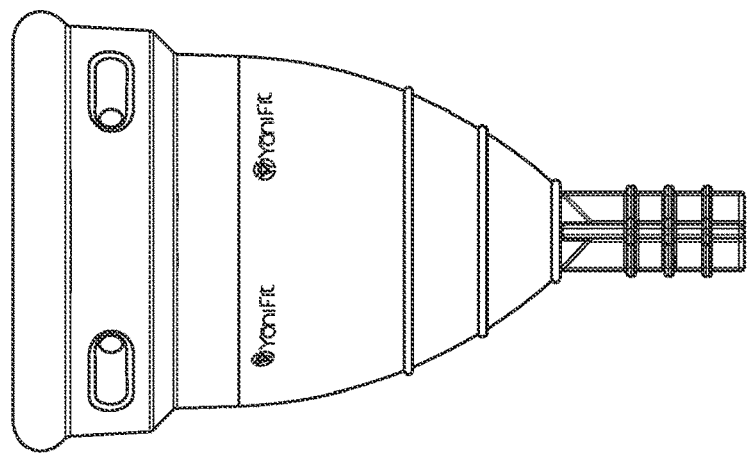

Referring to FIG. 29E, a side cross-sectional view of the vaginal insert device 2900 is depicted. The distance from the bottom of the device to the base of the upper portion may be a distance P of about 13 to about 14 mm, such as about 13.3 to about 13.7 mm, for example about 13.4 mm. The vaginal insert device 2900 may have a length N of about 50 to about 76 mm, such as about 55 to about 71 mm, for example about 57, 58, 59, 60, 61, 62, 63, 64, 65, 66, 67, 68, or 69 mm, including about 58 or about 63 mm. A width M of the enlarged portion may be about 3.5 to about 4.1 mm, such as about 3.8 mm. A width L of the rim may be about 4 to about 6 mm, such as about 5 mm.

Figure 29H:
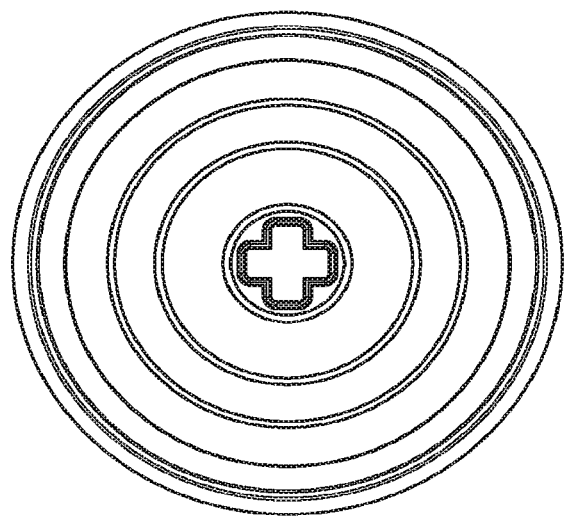
Figure 29G:
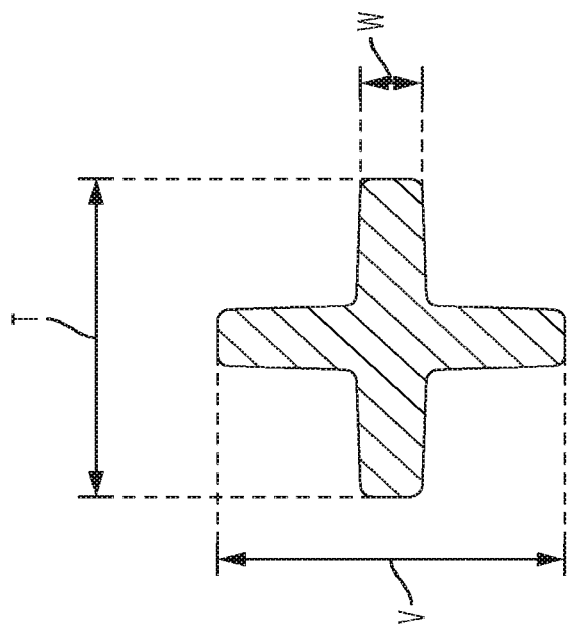
Figure 29F:
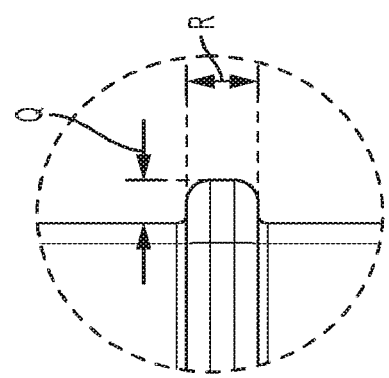

Referring to FIG. 29F, a detailed view of the ridges on the stem 244F is depicted. Each of the ridges may extend from the stem 244F by a distance Q of about 0.4 to about 0.6 mm, such as about 0.5 mm. Each of the ridges may have a thickness R of about 0.7 to about 0.9 mm, such as about 0.8 mm. Referring to FIG. 29G, a cross-sectional view of the stem 244F is depicted. The stem 244F may have an overall width T of about 6.6 to about 7 mm, such as about 6.8 mm and an overall width C of about 6.6 to about 7 mm, such as about 6.8 mm. Each leg of the cross-shaped stem 244F may have a width W of about 1.3 to about 1.5 mm, such as about 1.4 mm. Referring to FIG. 29H, a bottom view of the device 2900 is depicted.

Figure 30A:
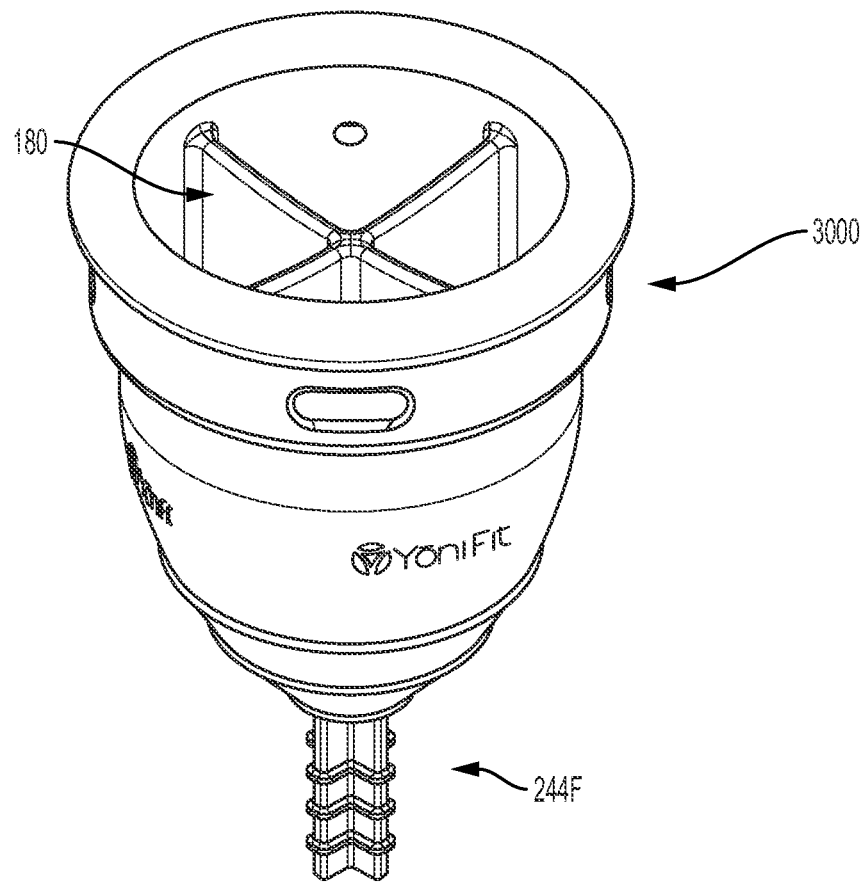
FIGS. 30A-30H illustrate a vaginal insert device, according to an embodiment of the present disclosure.

Referring to FIGS. 30A-30H, a vaginal insert device 3000 is shown. The vaginal insert device 3000 may be similar to the vaginal insert device 100 except that the stem 244F may be the cross-shaped stem 244f of FIG. 21F (although the stem also may be one of the stems 244a-244e, including the two dimensional stems 144 and 244b-c). The vaginal insert device 3000 may be similar to the vaginal insert devices 2700, 2800, 2900 except the sizing may be different. Accordingly, any of the previously described variations, uses, modifications, or features described with respect to any of the vaginal insert devices herein may be used, applied, or modified to the vaginal insert device 3000. For example, any of the variations, uses, modifications, or features with respect to the ribs 180, shape, ventilation openings, etc. may be provided on the vaginal insert device 3000. Additionally, any of the uses or accessories (e.g., the carrying case) may apply to the vaginal insert device 3000 as previously described. Referring to FIG. 30A, a perspective view of the vaginal insert device 3000 is shown with the rib 180 spaced a distance below the top surface of the device 3000. The upper portion, rim, ribs, ventilation openings, methods of insertion, rotation, adjusting pressure, use, and any other features or embodiments described herein may be presented with the vaginal insert device 3000.

Figure 30B:
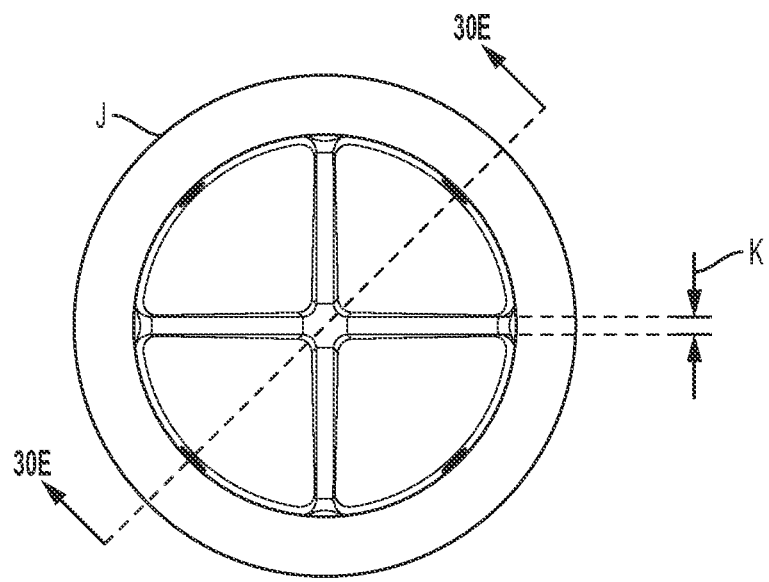
Figure 30C:
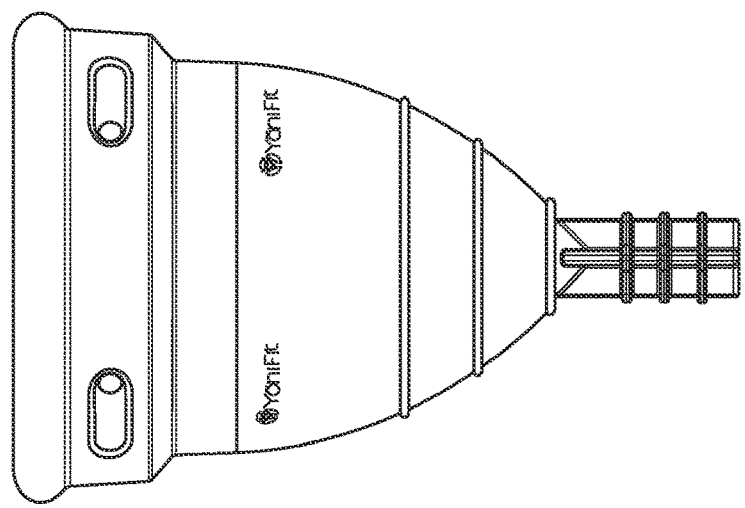
Figure 30D:
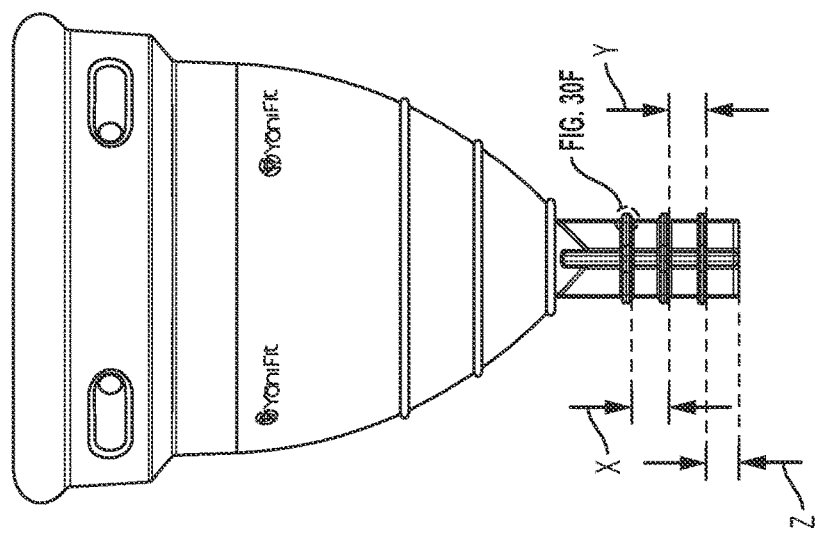

Referring to FIG. 30B, a top view of the vaginal insert device 3000 is shown. The vaginal insert device 3000 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 42 mm. The vaginal insert device 3000 may also have a width K of a rib 180 that is about 1 to about 1.6 mm, such as about 1.3 mm. Each of the four portions of the cross-shaped rib may have the dimension K. Referring to FIG. 30C, a side view of the vaginal insert device 3000 is shown. The ridges and optional logo may be spaced equidistant along the outer surface of the upper portion of the vaginal insert device 3000, as described with respect to previous embodiments. Referring to FIG. 30D, a side view rotated 90 degrees from the view of FIG. 30C is depicted. The ridges on the stem 244F may be spaced for each other. The lowermost ridge may be spaced a distance Z of about 2.7 to about 3.1 mm, such as about 2.9 mm from the bottom of the vaginal insert device 3000. The middle ridge may be spaced a distance Y of about 3.1 to about 3.5, such as about 3.3 mm from the lowermost ridge. The uppermost ridge may be spaced a distance X of about 3.1 to about 3.5, such as about 3.3 mm from the middle ridge.

Figure 30E:
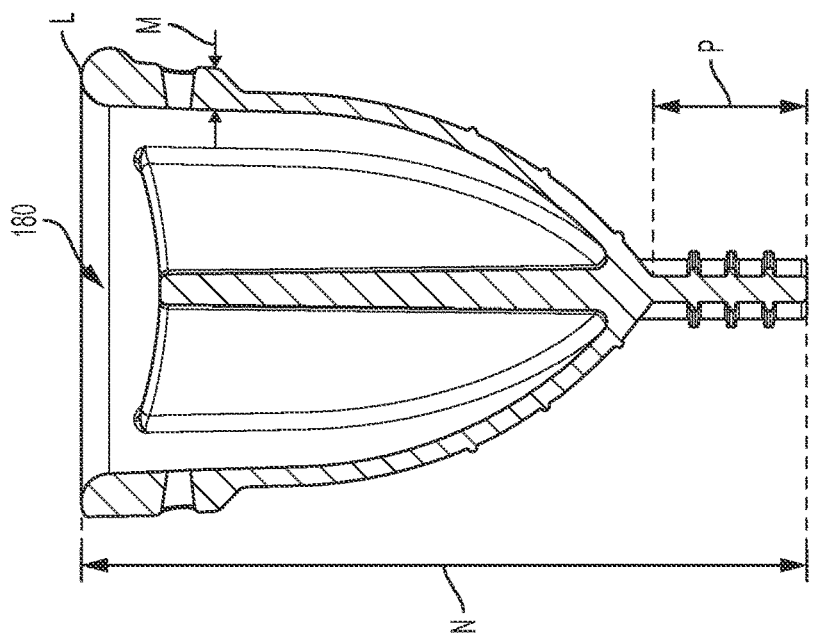

Referring to FIG. 30E, a side cross-sectional view of the vaginal insert device 3000 is depicted. The distance from the bottom of the device to the base of the upper portion may be a distance P of about 13 to about 14 mm, such as about 13.3 to about 13.7 mm, for example about 13.4 mm. The vaginal insert device 3000 may have a length N of about 50 to about 76 mm, such as about 55 to about 71 mm, for example about 57, 58, 59, 60, 61, 62, 63, 64, 65, 66, 67, 68, or 69 mm, including about 58 or about 63 mm. A width M of the enlarged portion may be about 3.5 to about 4.1 mm, such as about 3.8 mm. A width L of the rim may be about 4 to about 6 mm, such as about 5 mm.

Figure 30H:
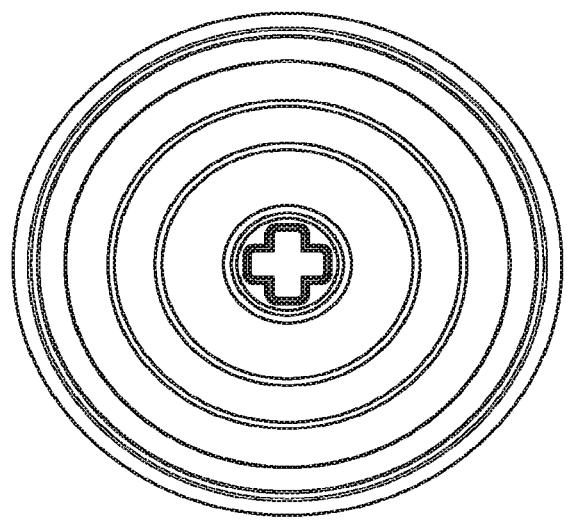
Figure 30G:
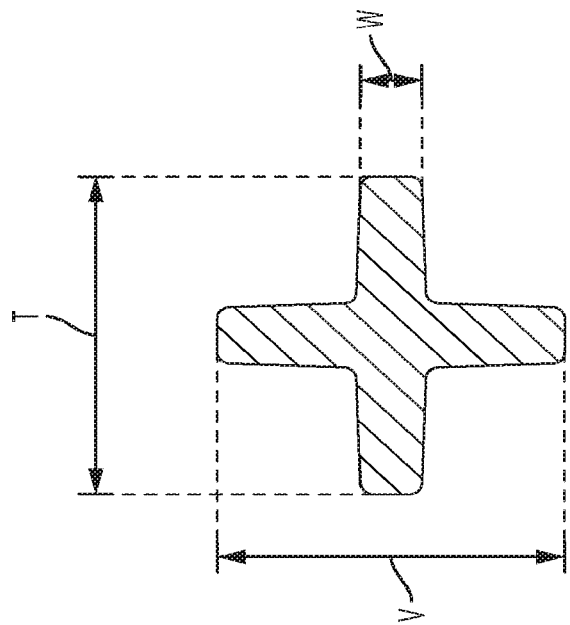
Figure 30F:
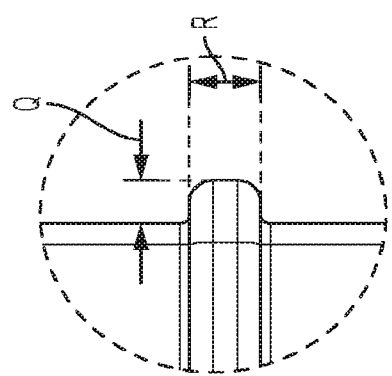

Referring to FIG. 30F, a detailed view of the ridges on the stem 244F is depicted. Each of the ridges may extend from the stem 244F by a distance Q of about 0.4 to about 0.6 mm, such as about 0.5 mm. Each of the ridges may have a thickness R of about 0.7 to about 0.9 mm, such as about 0.8 mm. Referring to FIG. 30G, a cross-sectional view of the stem 244F is depicted. The stem 244F may have an overall width T of about 6.6 to about 7 mm, such as about 6.8 mm and an overall width C of about 6.6 to about 7 mm, such as about 6.8 mm. Each leg of the cross-shaped stem 244F may have a width W of about 1.3 to about 1.5 mm, such as about 1.4 mm. Referring to FIG. 30H, a bottom view of the device 3000 is depicted.

Figure 31A:
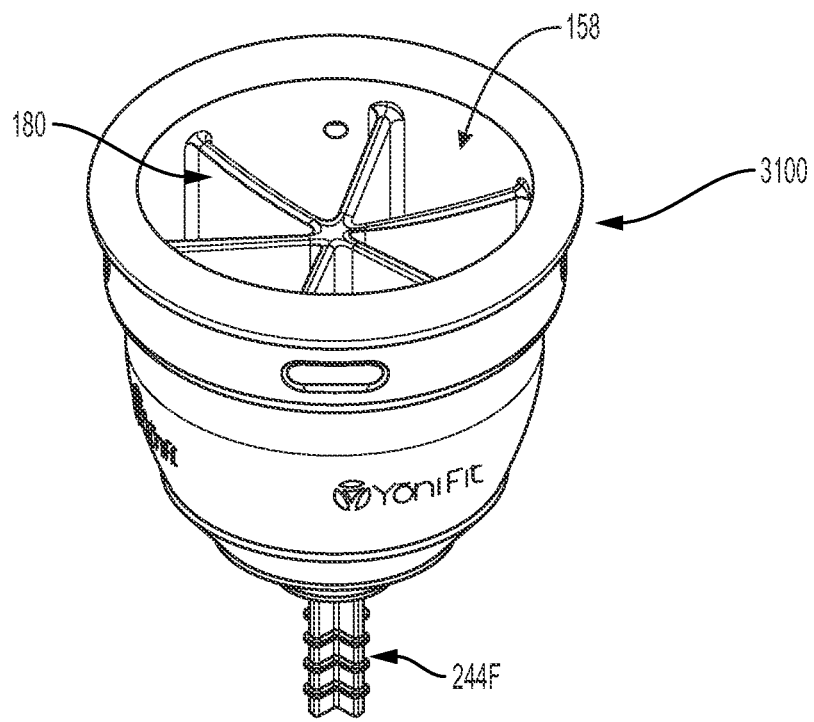
FIGS. 31A-31H illustrate a vaginal insert device, according to an embodiment of the present disclosure.

Referring to FIGS. 31A-31H, a vaginal insert device 3100 is shown. The vaginal insert device 3100 may be similar to the vaginal insert device 100 except that the stem 244F may be the cross-shaped stem 244f of FIG. 21F (although the stem also may be one of the stems 244a-244e, including the two-dimensional stems 144 and 244b-c). The vaginal insert device 3100 may be similar to the vaginal insert devices 2700, 2800, 2900, 3000 except the sizing may be different. Accordingly, any of the previously described variations, uses, modifications, or features described with respect to any of the vaginal insert devices herein may be used, applied, or modified to the vaginal insert device 3100. For example, any of the variations, uses, modifications, or features with respect to the ribs 180, shape, ventilation openings, etc. may be provided on the vaginal insert device 3100. Additionally, any of the uses or accessories (e.g., the carrying case) may apply to the vaginal insert device 3100 as previously described. Referring to FIG. 31A, a perspective view of the vaginal insert device 3100 is shown with the rib 180 spaced a distance below the top surface of the device 3100. The upper portion, rim, ribs, ventilation openings, methods of insertion, rotation, adjusting pressure, use, and any other features or embodiments described herein may be presented with the vaginal insert device 3100.

size of the vaginal insert device 3100, an additional rib section may be provided to the rib 180 such that there are six individual rib portions or members, and six open portions 158. The additional rib portions may allow for added force to be applied to the organ walls as well as added support for the device. The additional rib portions may also assist in preventing and inhibiting prolapse in the larger size device 3100. That is, since the device 3100 has a larger open internal diameter, the six ribs portions of rib 180 may result in smaller open space than if only four rib portions were provided, as in previous embodiments. The smaller open space may assist in preventing prolapse.

Figure 31B:
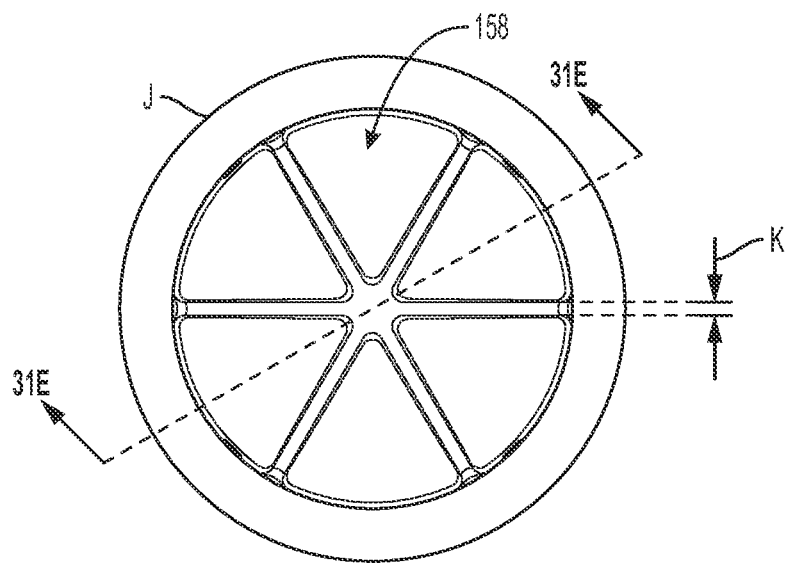

Referring to FIG. 31B, a top view of the vaginal insert device 3100 is shown. The vaginal insert device 3100 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 48 mm. The vaginal insert device 3100 may also have a width K of a rib 180 that is about 1 to about 1.6 mm, such as about 1.3 mm. Each of the six portions of the cross-shaped rib may have the dimension K. Referring to FIG. 31C, a side view of the vaginal insert device 3100 is shown. The ridges and optional logo may be spaced equidistant along the outer surface of the upper portion of the vaginal insert device 3100, as described with respect to previous embodiments. Referring to FIG. 31D, a side view rotated 90 degrees from the view of FIG. 31C is depicted. The ridges on the stem 244F may be spaced for each other. The lowermost ridge may be spaced a distance Z of about 2.7 to about 3.1 mm, such as about 2.9 mm from the bottom of the vaginal insert device 3100. The middle ridge may be spaced a distance Y of about 3.1 to about 3.5, such as about 3.3 mm from the lowermost ridge. The uppermost ridge may be spaced a distance X of about 3.1 to about 3.5, such as about 3.3 mm from the middle ridge.

Figure 31E:
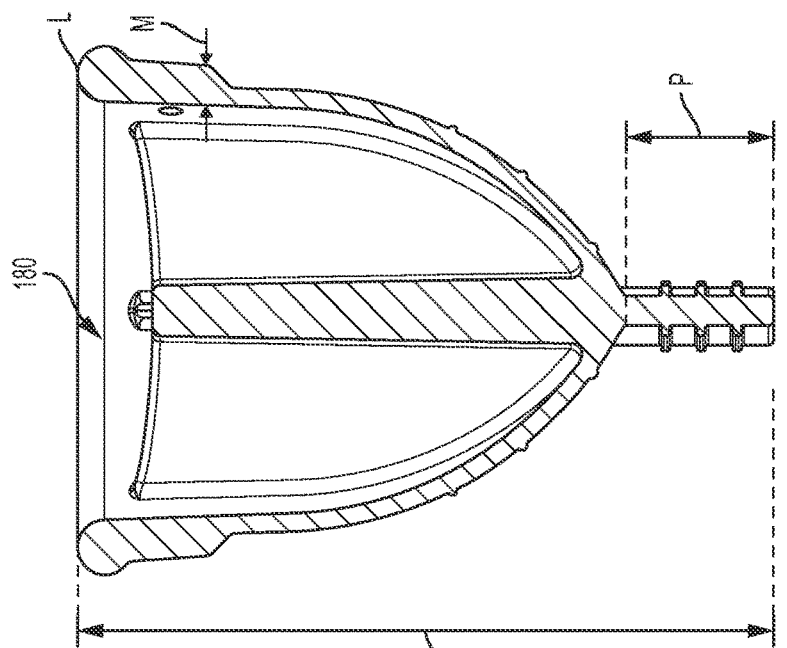
Figure 31D:
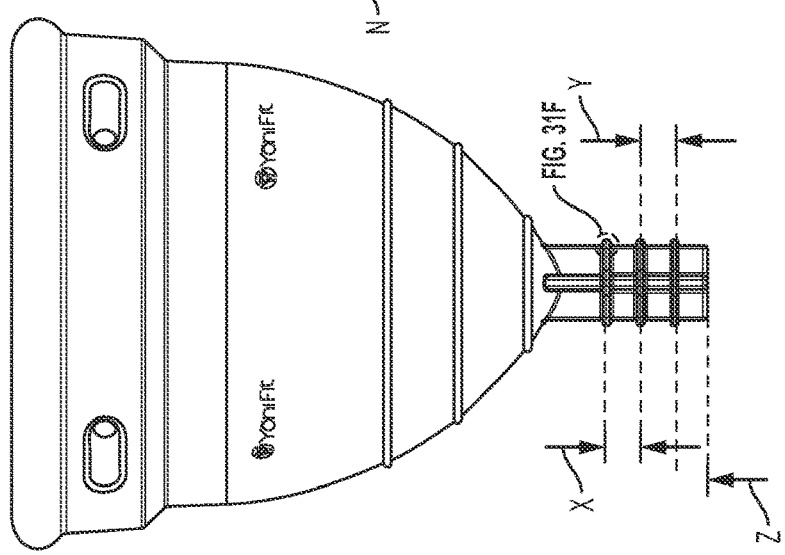
Figure 31C:
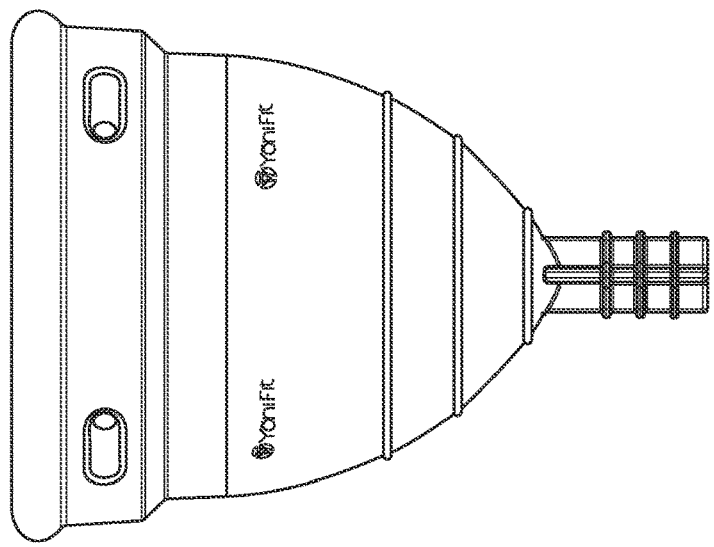

Referring to FIG. 31E, a side cross-sectional view of the vaginal insert device 3100 is depicted. The distance from the bottom of the device to the base of the upper portion may be a distance P of about 13 to about 14 mm, such as about 13.3 to about 13.7 mm, for example about 13.5 mm. The vaginal insert device 3100 may have a length N of about 50 to about 76 mm, such as about 55 to about 71 mm, for example about 57, 58, 59, 60, 61, 62, 63, 64, 65, 66, 67, 68, or 69 mm, including about 58 or about 63 mm. A width M of the enlarged portion may be about 3.5 to about 4.1 mm, such as about 3.8 mm. A radius L of the rim may be about 4 to about 6 mm, such as about 5 mm.

Figure 31H:
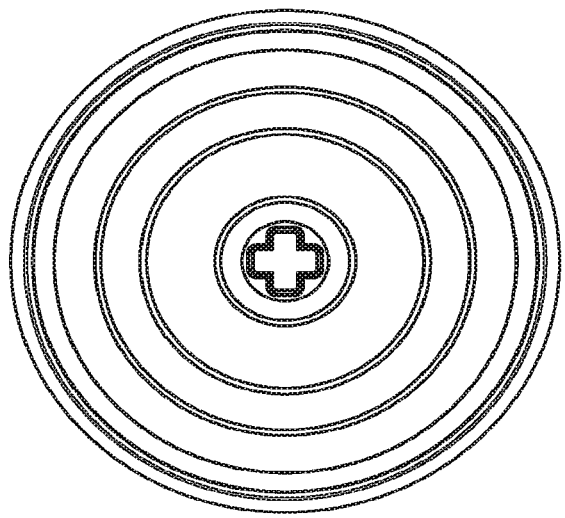
Figure 31G:
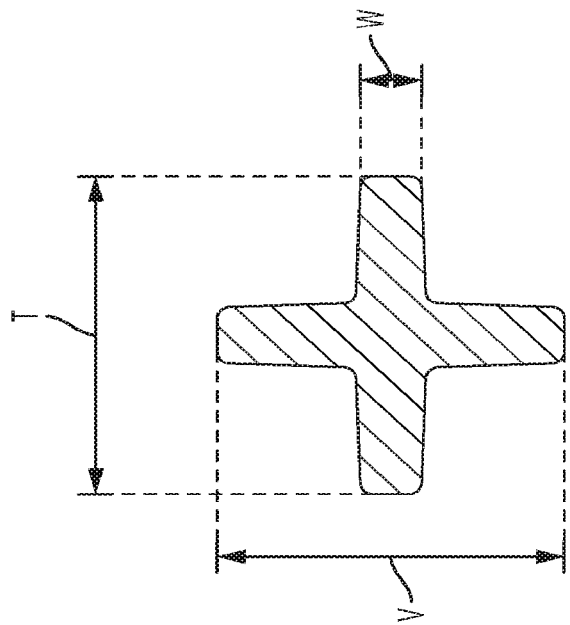
Figure 31F:
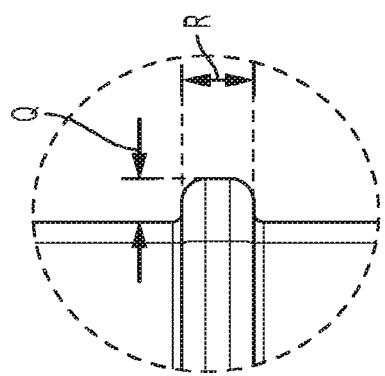

Referring to FIG. 31F, a detailed view of the ridges on the stem 244F is depicted. Each of the ridges may extend from the stem 244F by a distance Q of about 0.4 to about 0.6 mm, such as about 0.5 mm. Each of the ridges may have a thickness R of about 0.7 to about 0.9 mm, such as about 0.8 mm. Referring to FIG. 31G, a cross-sectional view of the stem 244F is depicted. The stem 244F may have an overall width T of about 6.6 to about 7 mm, such as about 6.8 mm and an overall width C of about 6.6 to about 7 mm, such as about 6.8 mm. Each leg of the cross-shaped stem 244F may have a width W of about 1.3 to about 1.5 mm, such as about 1.4 mm. Referring to FIG. 31H, a bottom view of the device 3100 is depicted.

Figure 32A:
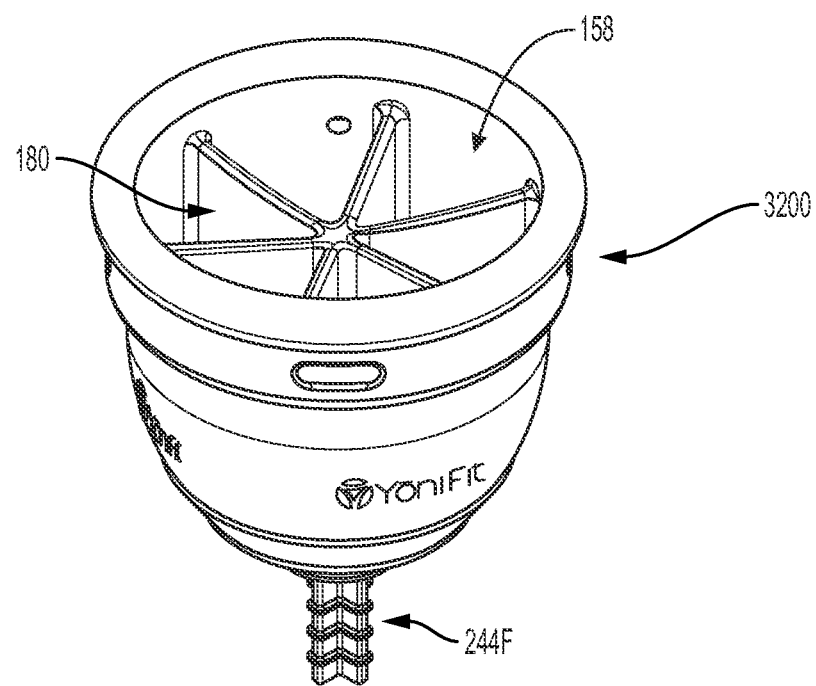
FIGS. 32A-32H illustrate a vaginal insert device, according to an embodiment of the present disclosure.
Figure 32B:
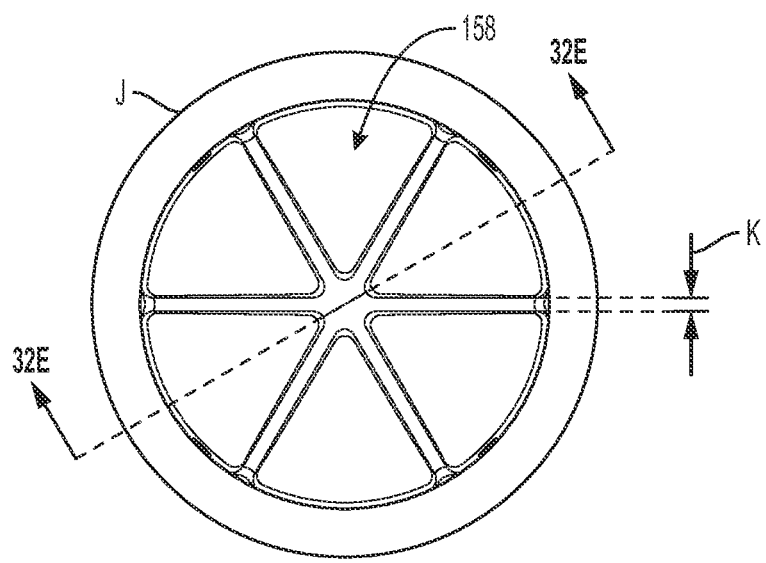

Referring to FIGS. 32A-32H, a vaginal insert device 3200 is shown. The vaginal insert device 3200 may be similar to the vaginal insert device 100 except that the stem 244F may be the cross-shaped stem 244f of FIG. 21F (although the stem also may be one of the stems 244a-244e, including the two dimensional stems 144 and 244b-c). The vaginal insert device 3100 may be similar to the vaginal insert devices 2700, 2800, 2900, 3000, 3100 except the sizing may be different. Accordingly, any of the previously described variations, uses, modifications, or features described with respect to any of the vaginal insert devices herein may be used, applied, or modified to the vaginal insert device 3200. For example, any of the variations, uses, modifications, or features with respect to the ribs 180, shape, ventilation openings, etc. may be provided on the vaginal insert device 3200. Additionally, any of the uses or accessories (e.g., the carrying case) may apply to the vaginal insert device 3200 as previously described. Referring to FIG. 32A, a perspective view of the vaginal insert device 3200 is shown with the rib 180 spaced a distance below the top surface of the device 3200. The upper portion, rim, ribs, ventilation openings, methods of insertion, rotation, adjusting pressure, use, and any other features or embodiments described herein may be presented with the vaginal insert device 3200.

As depicted in FIG. 32A, due to the larger size of the vaginal insert device 3200, an additional rib section may be provided to the rib 180 such that there are six individual rib portions or members, and six open portions 158. The additional rib portions may allow for added force to be applied to the organ walls as well as added support for the device. The additional rib portions may also assist in preventing and inhibiting prolapse in the larger size device 3200. That is, since the device 3200 has a larger open internal diameter, the six ribs portions of rib 180 may result in smaller open space than if only four rib portions were provided, as in previous embodiments. The smaller open space may assist in preventing prolapse.

Referring to FIG. 32B, a top view of the vaginal insert device 3200 is shown. The vaginal insert device 3200 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 52 mm. The vaginal insert device 3200 may also have a width K of a rib 180 that is about 1 to about 1.6 mm, such as about 1.3 mm. Each of the six portions of the cross-shaped rib may have the dimension K. Referring to FIG. 32C, a side view of the vaginal insert device 3200 is shown. The ridges and optional logo may be spaced equidistant along the outer surface of the upper portion of the vaginal insert device 3200, as described with respect to previous embodiments. Referring to FIG. 32D, a side view rotated 90 degrees from the view of FIG. 32C is depicted. The ridges on the stem 244F may be spaced for each other. The lowermost ridge may be spaced a distance Z of about 2.7 to about 3.1 mm, such as about 2.9 mm from the bottom of the vaginal insert device 3200. The middle ridge may be spaced a distance Y of about 3.1 to about 3.5, such as about 3.3 mm from the lowermost ridge. The uppermost ridge may be spaced a distance X of about 3.1 to about 3.5, such as about 3.3 mm from the middle ridge.

Figure 32E:
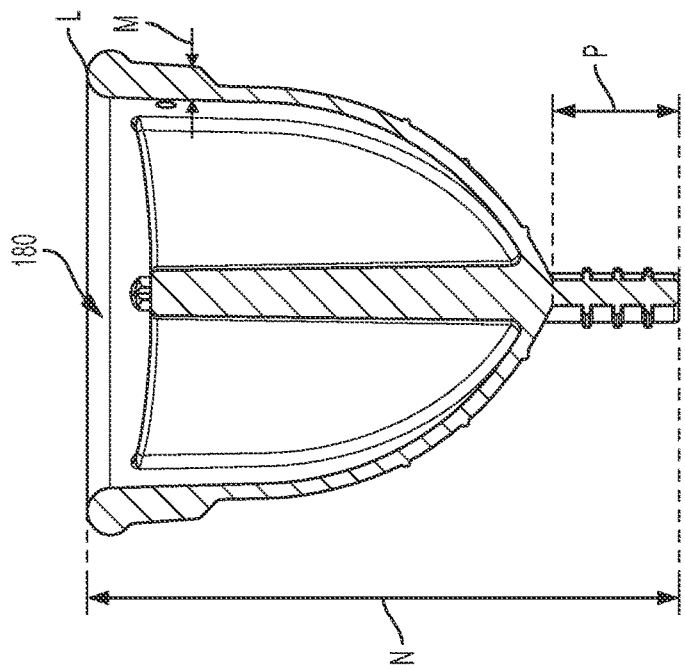
Figure 32D:
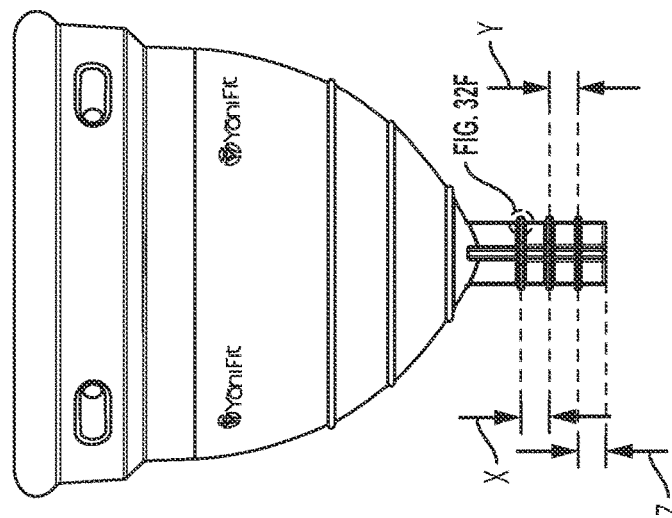
Figure 32C:
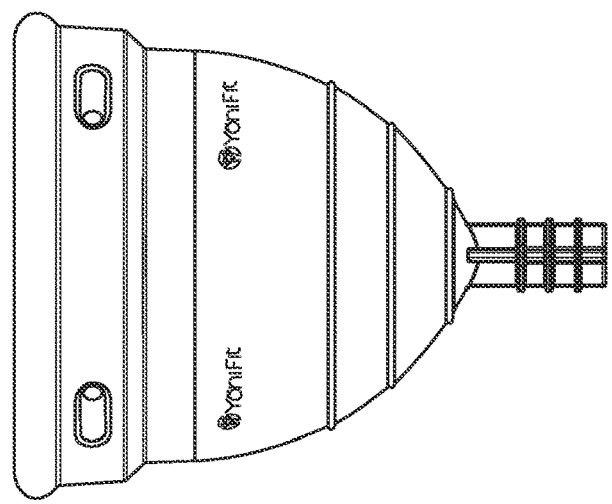

Referring to FIG. 32E, a side cross-sectional view of the vaginal insert device 3200 is depicted. The distance from the bottom of the device to the base of the upper portion may be a distance P of about 13 to about 14 mm, such as about 13.3 to about 13.7 mm, for example about 13.5 mm. The vaginal insert device 3200 may have a length N of about 50 to about 76 mm, such as about 55 to about 71 mm, for example about 57, 58, 59, 60, 61, 62, 63, 64, 65, 66, 67, 68, or 69 mm, including about 58 or about 63 mm. A width M of the enlarged portion may be about 3.5 to about 4.1 mm, such as about 3.8 mm. A width L of the rim may be about 4 to about 6 mm, such as about 5 mm.

Figure 32H:
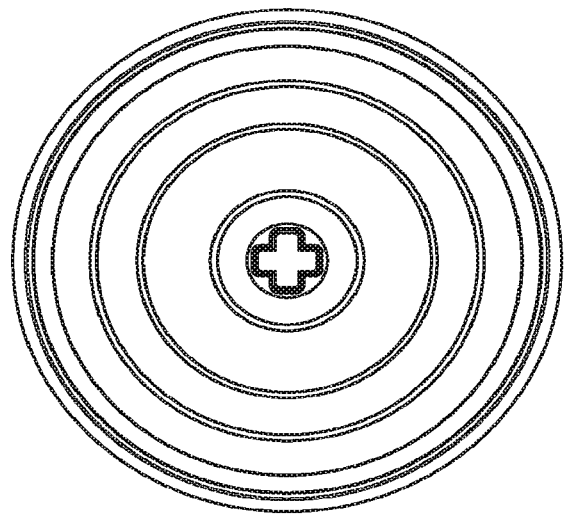
Figure 32G:
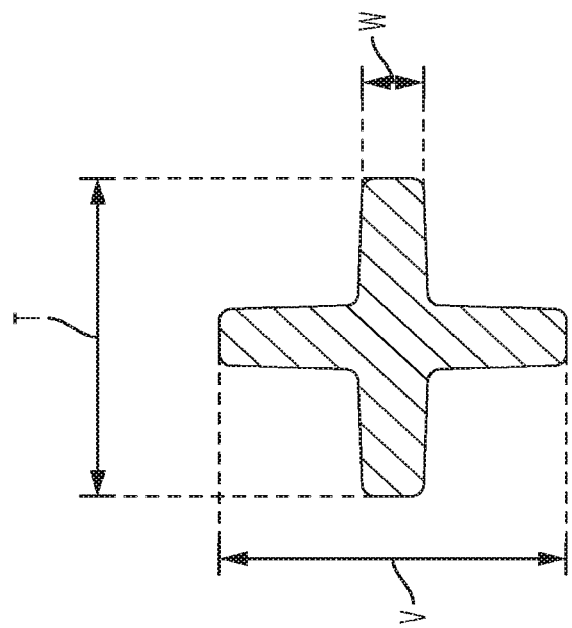
Figure 32F:
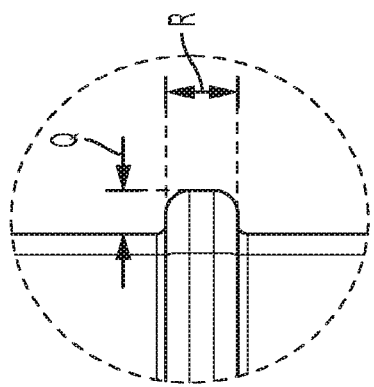

Referring to FIG. 32F, a detailed view of the ridges on the stem 244F is depicted. Each of the ridges may extend from the stem 244F by a distance Q of about 0.4 to about 0.6 mm, such as about 0.5 mm. Each of the ridges may have a thickness R of about 0.7 to about 0.9 mm, such as about 0.8 mm. Referring to FIG. 32G, a cross-sectional view of the stem 244F is depicted. The stem 244F may have an overall width T of about 6.6 to about 7 mm, such as about 6.8 mm and an overall width C of about 6.6 to about 7 mm, such as about 6.8 mm. Each leg of the cross-shaped stem 244F may have a width W of about 1.3 to about 1.5 mm, such as about 1.4 mm. Referring to FIG. 32H, a bottom view of the device 3200 is depicted.

Figure 33A:
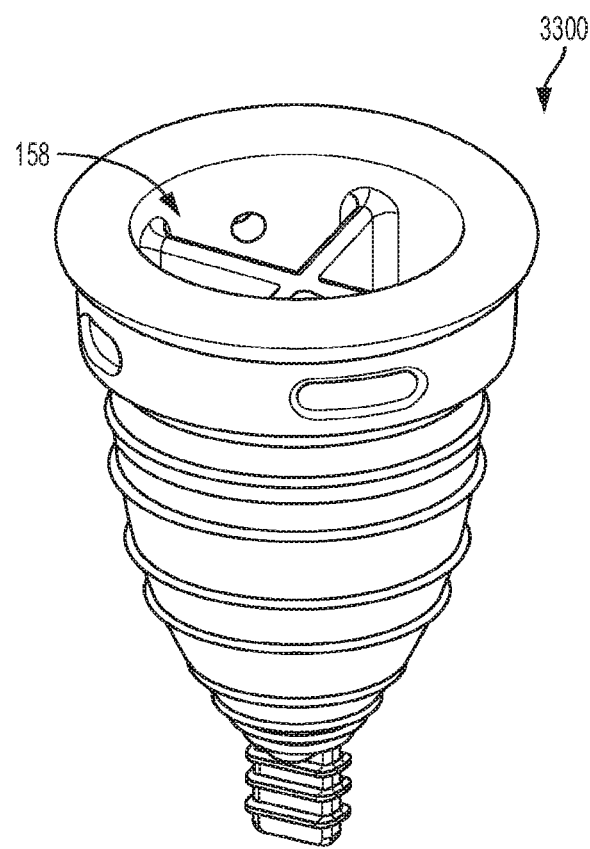
FIGS. 33A-33L illustrate a vaginal insert device, according to an embodiment of the present disclosure.

Referring to FIGS. 33A-33L, a vaginal insert device 3300 is shown. The vaginal insert device 3300 may be similar to the vaginal insert devices described in FIGS. 27-32 except that the stem 244g may be a flat, rectangular, two dimensional stem. Accordingly, any of the previously described variations, uses, modifications, or features described with respect to any of the vaginal insert devices herein may be used, applied, or modified to the vaginal insert device 3300. For example, any of the variations, uses, modifications, or features with respect to the ribs 180, shape, ventilation openings, etc. may be provided on the vaginal insert device 3300. Additionally, any of the uses or accessories (e.g., the carrying case) may apply to the vaginal insert device 3300 as previously described. Referring to FIG. 33A, a perspective view of the vaginal insert device 3300 is shown with the rib 180 spaced a distance below the top surface of the device 3300. The upper portion, rim, ribs, ventilation openings, methods of insertion, rotation, adjusting pressure, use, and any other features or embodiments described herein may be presented with the vaginal insert device 3300.

Figure 33B:
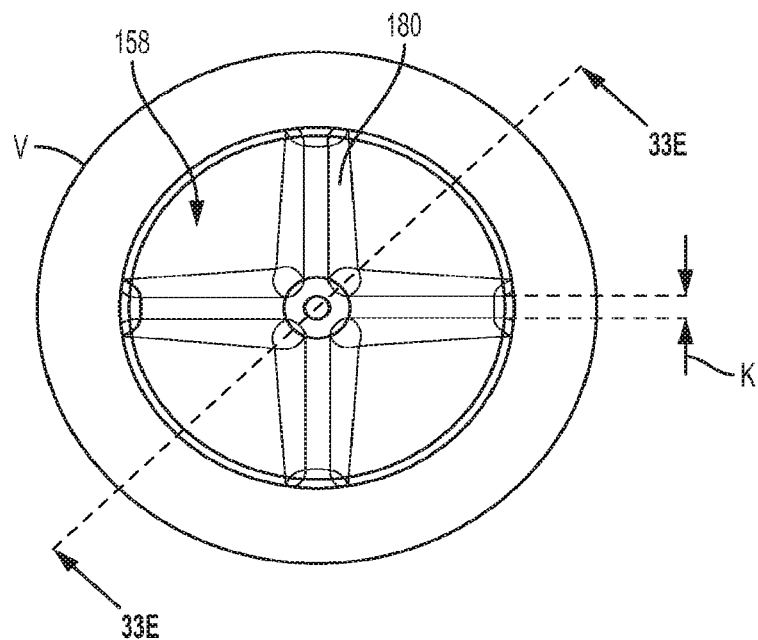

Referring to FIG. 33B, a top view of the vaginal insert device 3300 is shown. The vaginal insert device 3300 may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 34 mm. The vaginal insert device 3300 may also have a width K of a rib 180 that is about 1 to about 1.6 mm, such as about 1.3 mm. Each of the four portions of the cross-shaped rib may have the dimension K. Referring to FIG. 33C, a side view of the vaginal insert device 3300 is shown. The ridges and optional logo may be spaced equidistant along the outer surface of the upper portion of the vaginal insert device 3300, as described with respect to previous embodiments. Referring to FIG. 33D, a side view rotated 90 degrees from the view of FIG. 33C is depicted. The ridges on the stem 244g may be spaced for each other. The lowermost ridge may be spaced a distance Z of about 2.2 to about 2.6 mm, such as about 2.4 mm from the bottom of the vaginal insert device 3300. The middle ridge may be spaced a distance Y of about 2.0 to about 2.4, such as about 2.2 mm from the lowermost ridge. The uppermost ridge may be spaced a distance X of about 2.0 to about 2.4, such as about 2.2 mm from the middle ridge.

Figure 33E:
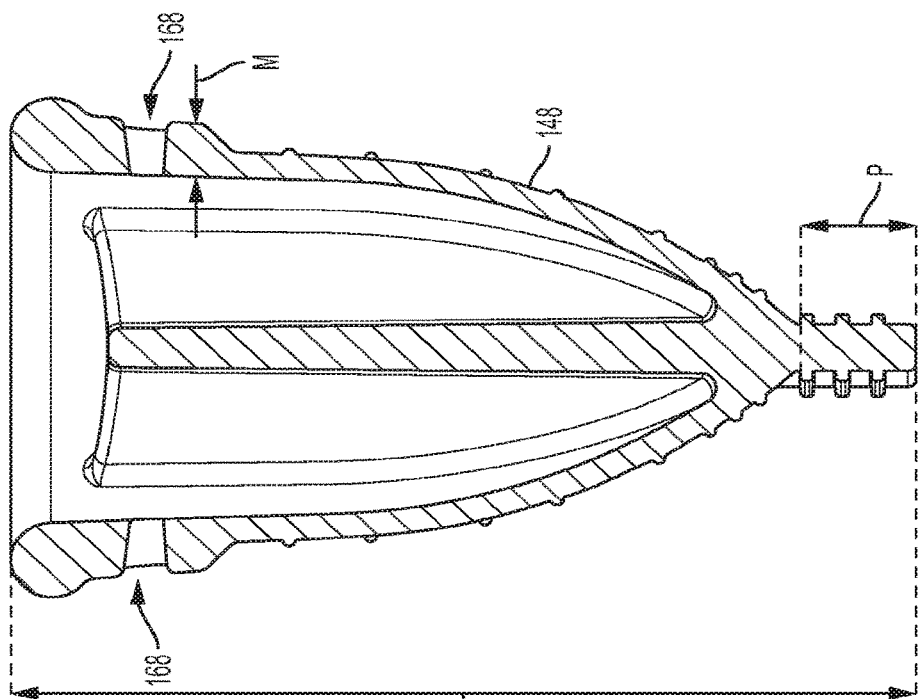
Figure 33D:
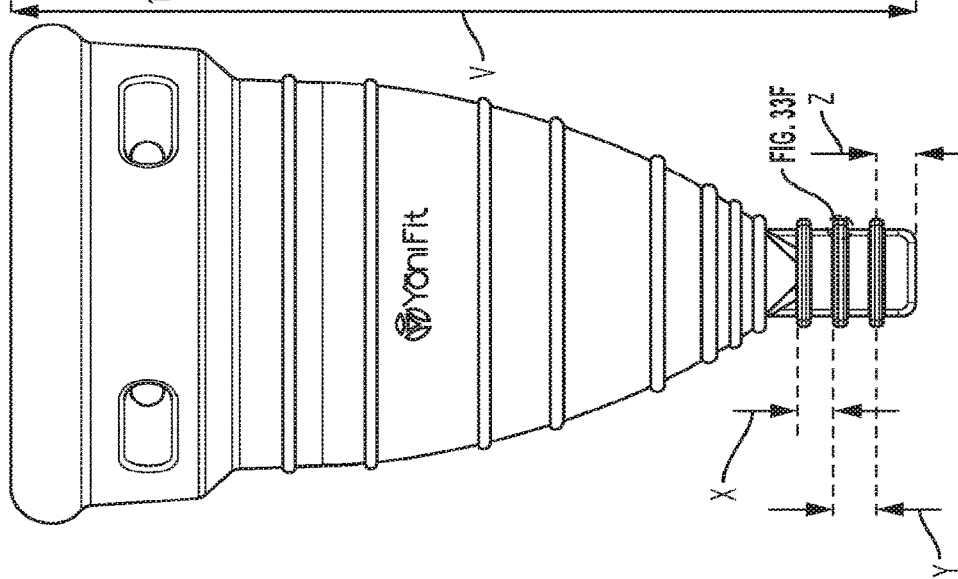
Figure 33C:
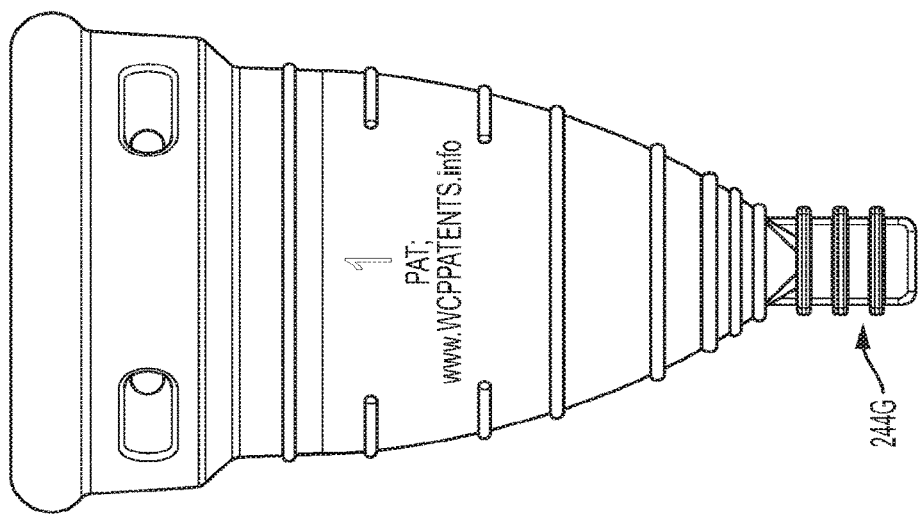

Referring to FIG. 33E, a side cross-sectional view of the vaginal insert device 3300 is depicted. The distance from the bottom of the device to the base of the upper portion may be a distance P of about 7 to about 8 mm, such as about 7.1 to about 7.4 mm, for example about 7.3 mm. The vaginal insert device 3300 may have a length N of about 45 to about 75 mm, such as about 50 to about 70 mm, such as about 54 to about 58 mm, such as about 54.5 to about 58.4 mm, for example about 46, 46.5, 48, 48.5, 50, 50.5, 52, 52.5, 54, 54.5, 56, 56.5, 58, 58.5, 60, 60.6, 62, 62.5, 63, 63.5, 64, 64.5, 66, 66.5, 68, 68.5, 70, 70.5, 72, 72.5, 74, 74/5 mm+/−1 mm or +/−0.1 mm, including 56.4 mm/−1 mm. A width M of the enlarged portion may be about 3.5 to about 4.1 mm, such as about 3.8 mm. A width L of the rim may be about 4 to about 6 mm, such as about 5 mm.

Figure 33F:
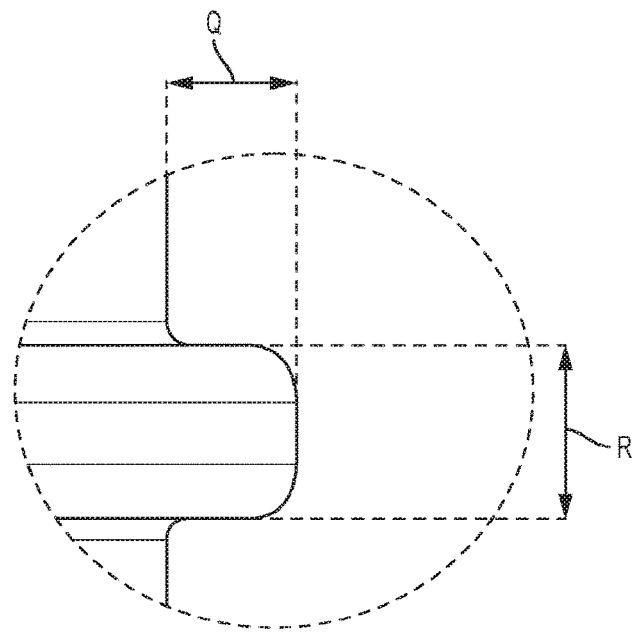
Figure 33G:
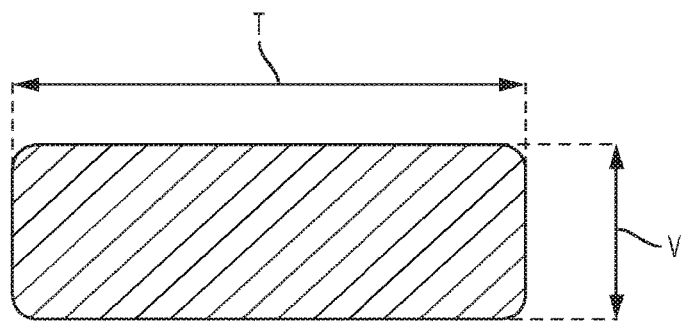
Figure 33H:
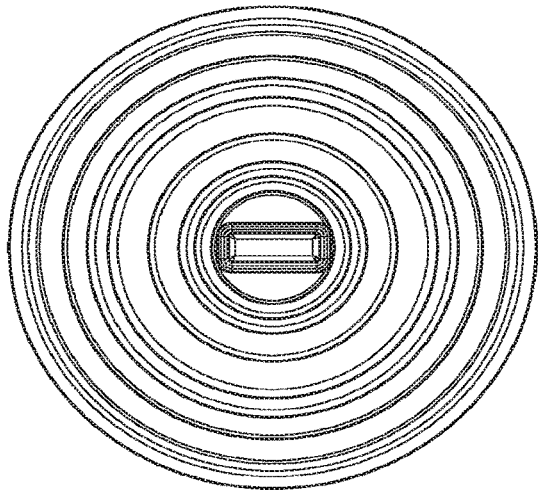
Figure 33I:
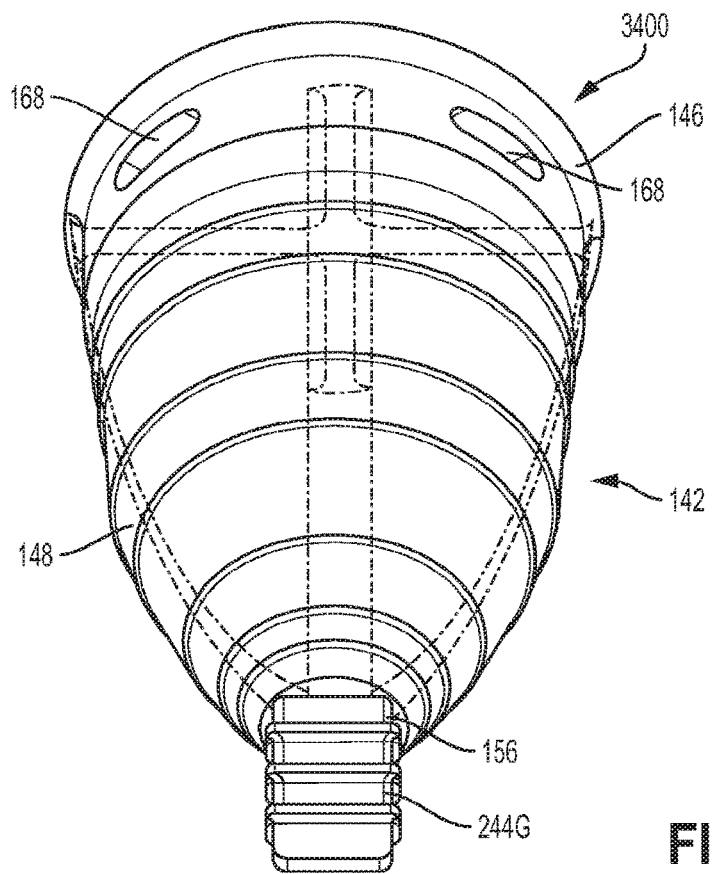
Figure 33J:
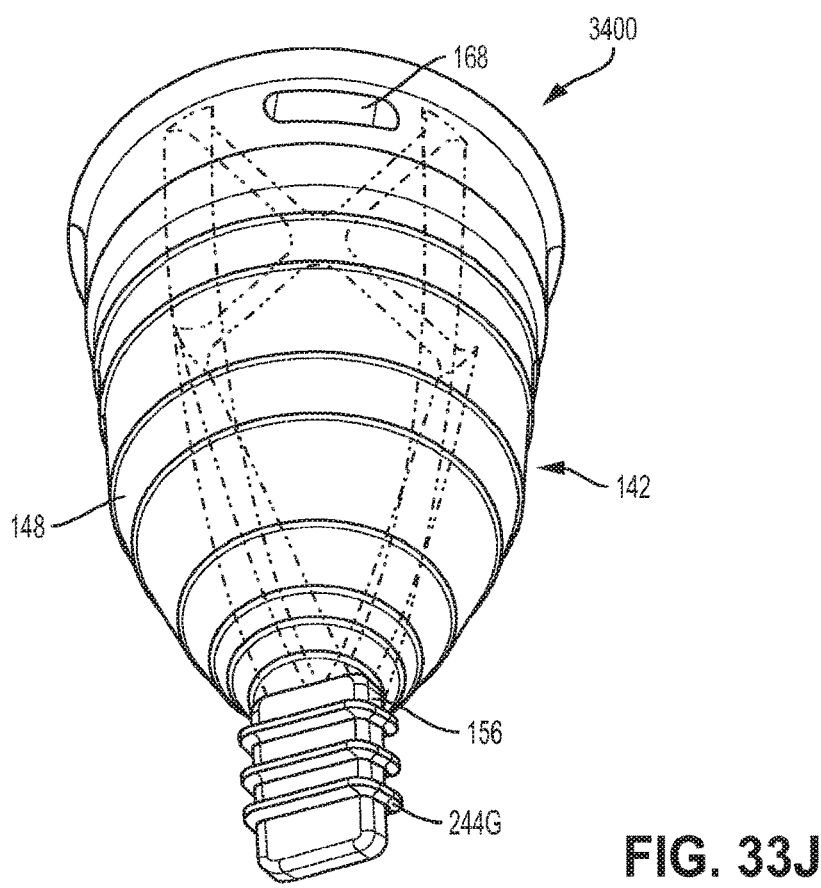
Figure 33K:
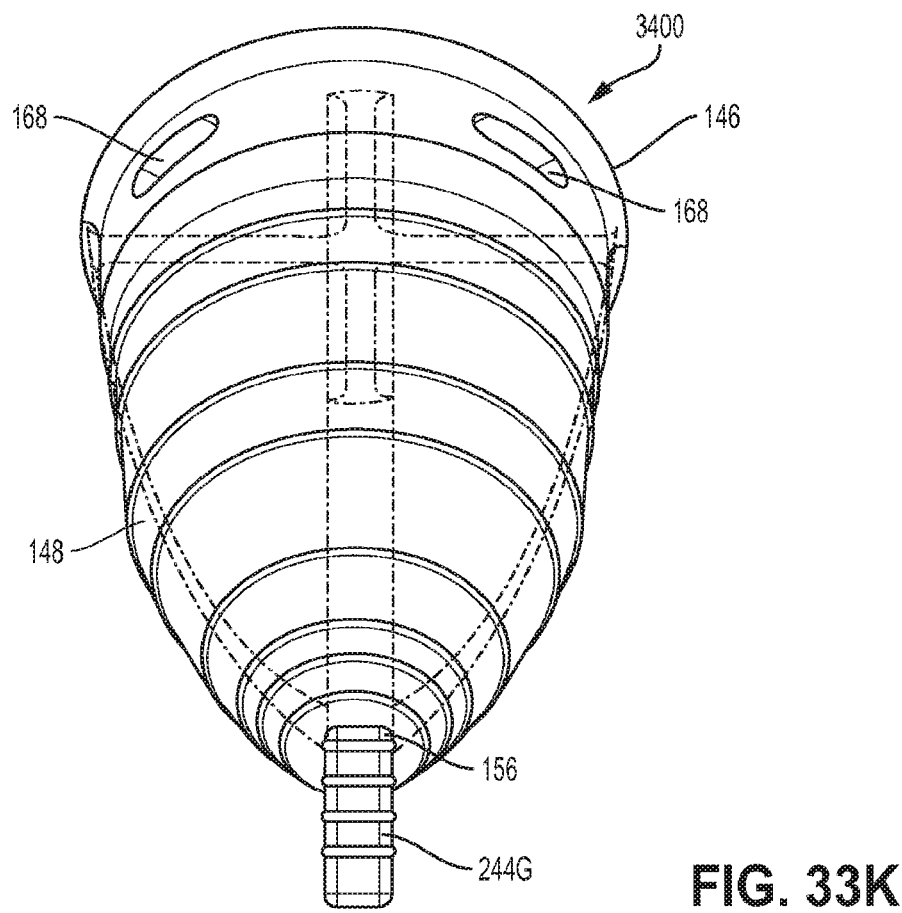
Figure 33L:
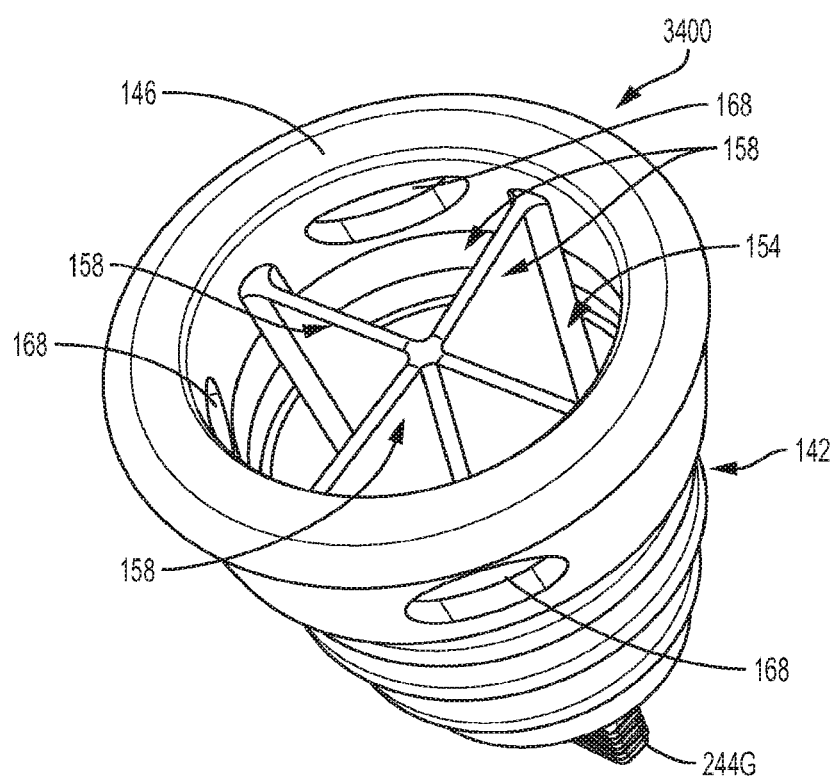
Figure 34B:
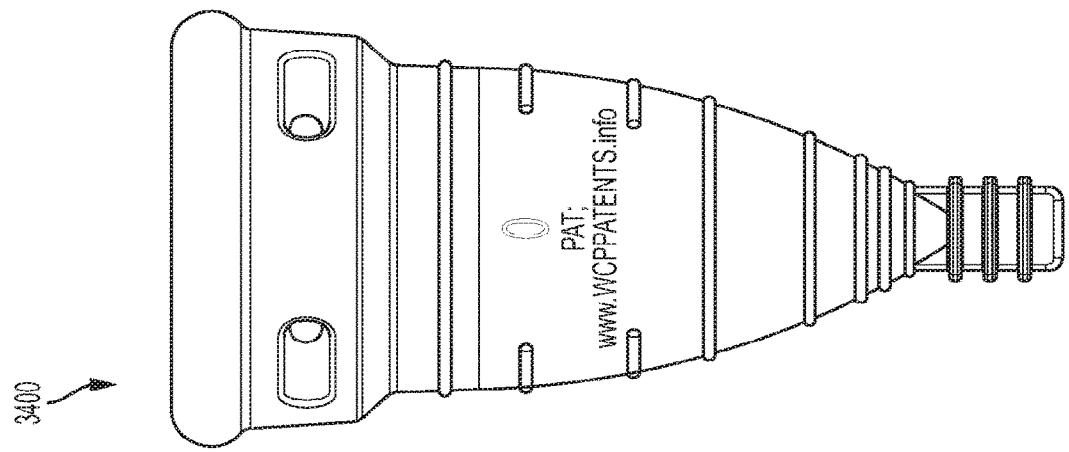
FIGS. 34A-34D illustrate a vaginal insert device, according to an embodiment of the present disclosure.
Figure 34A:
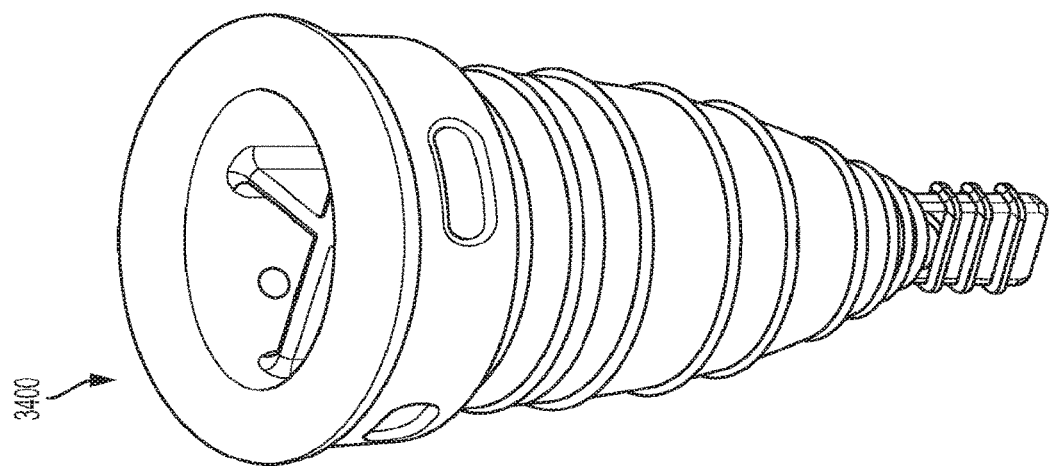
Figure 34D:
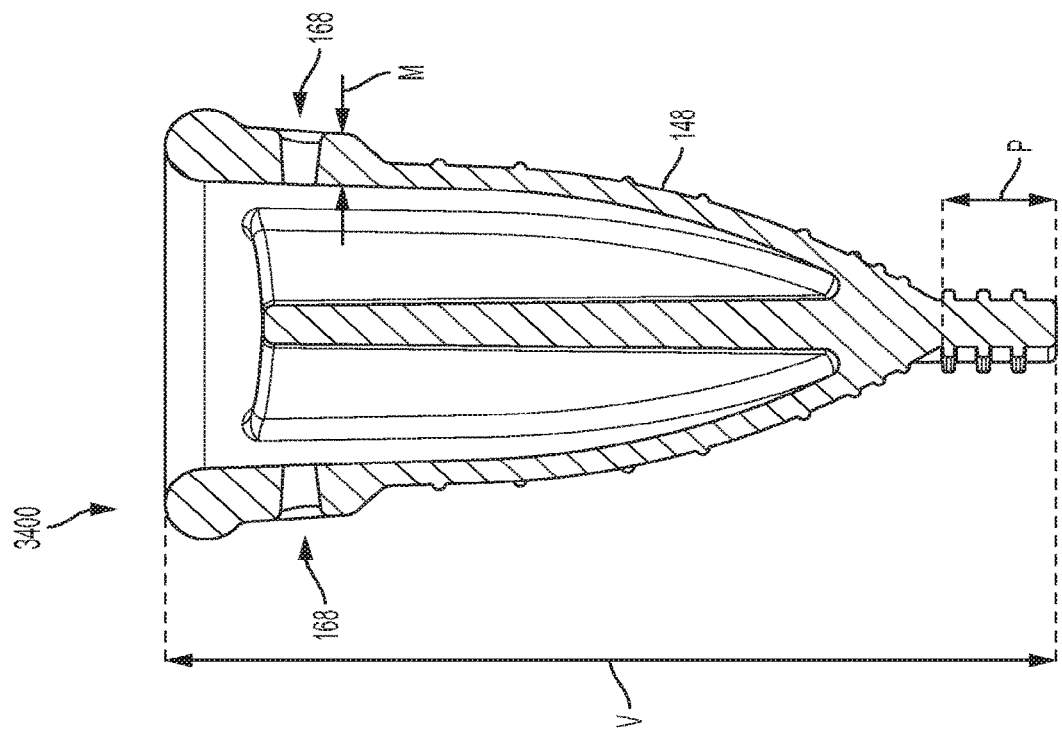
Figure 34C:
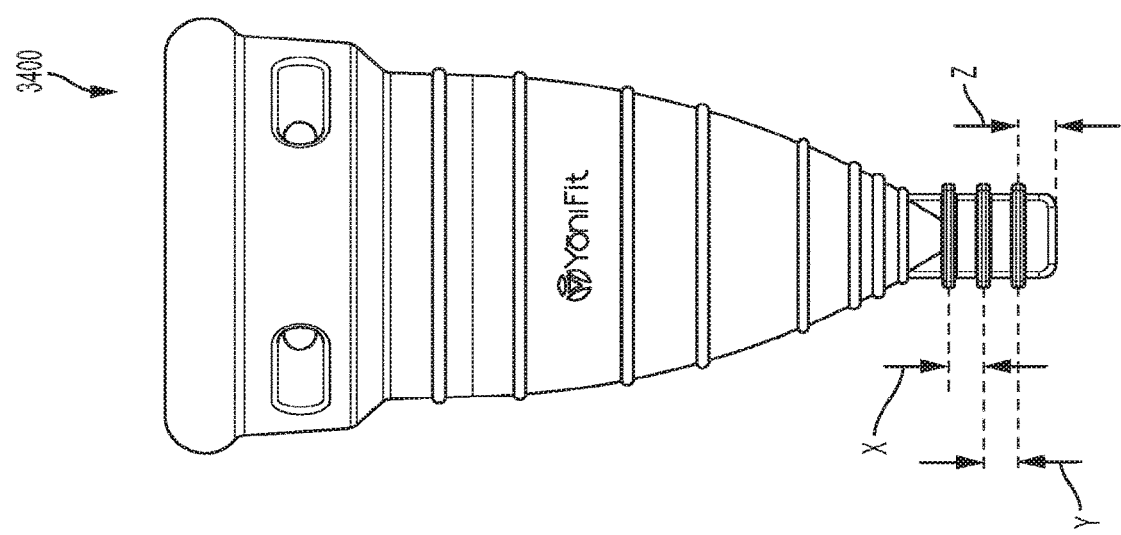
Figure 35A:
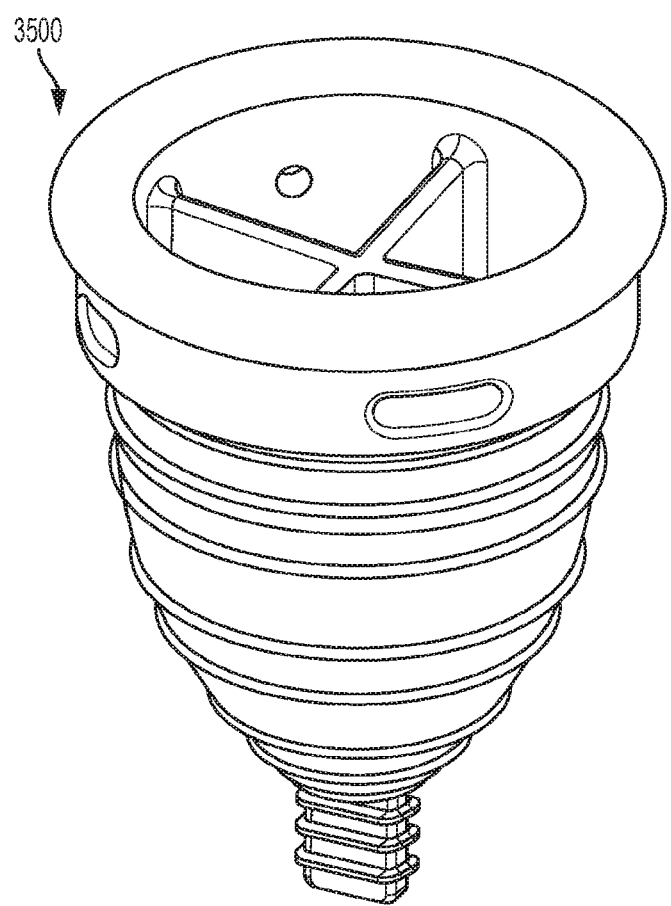
FIGS. 35A-35D illustrate a vaginal insert device, according to an embodiment of the present disclosure.
Figure 35D:
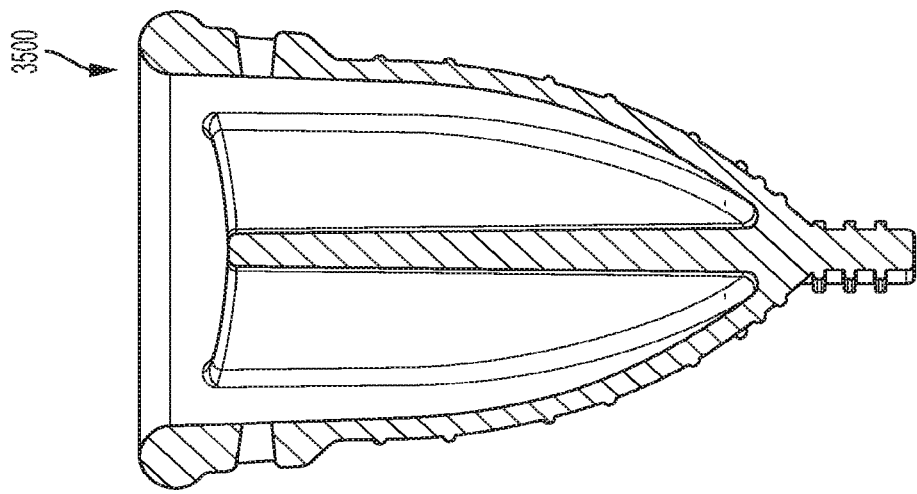
Figure 35C:
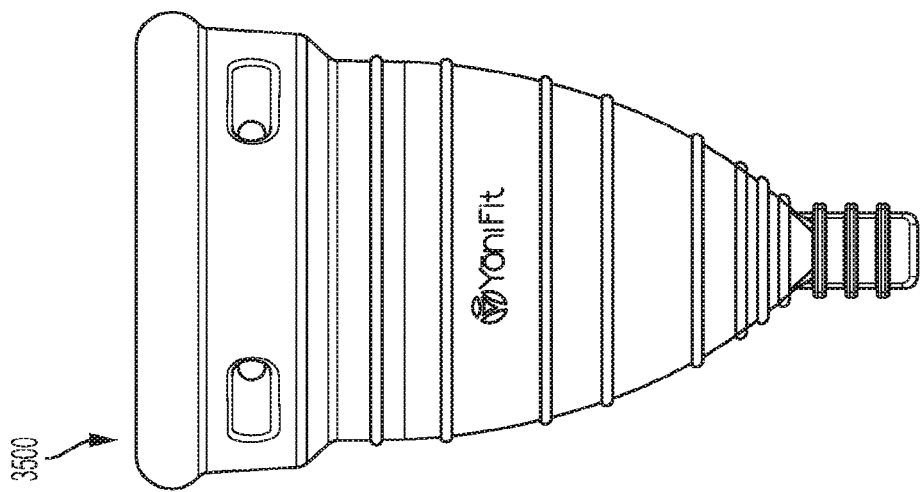
Figure 35B:
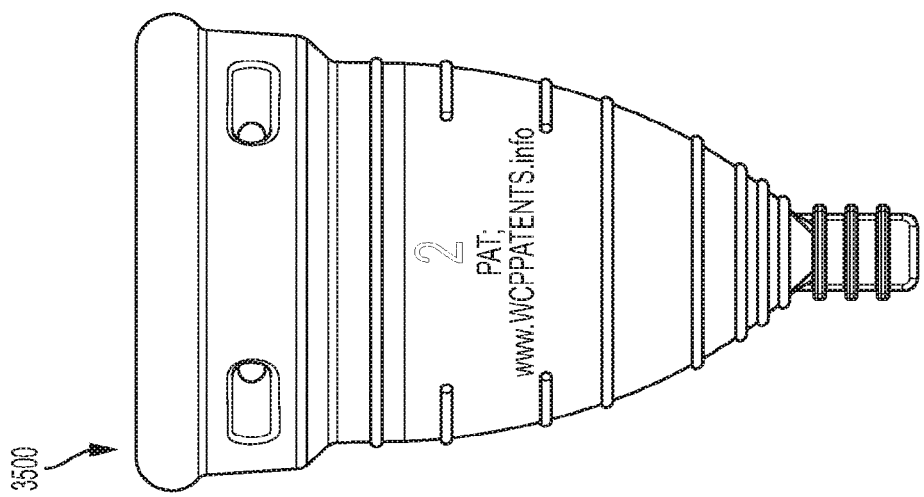
Figure 36B:
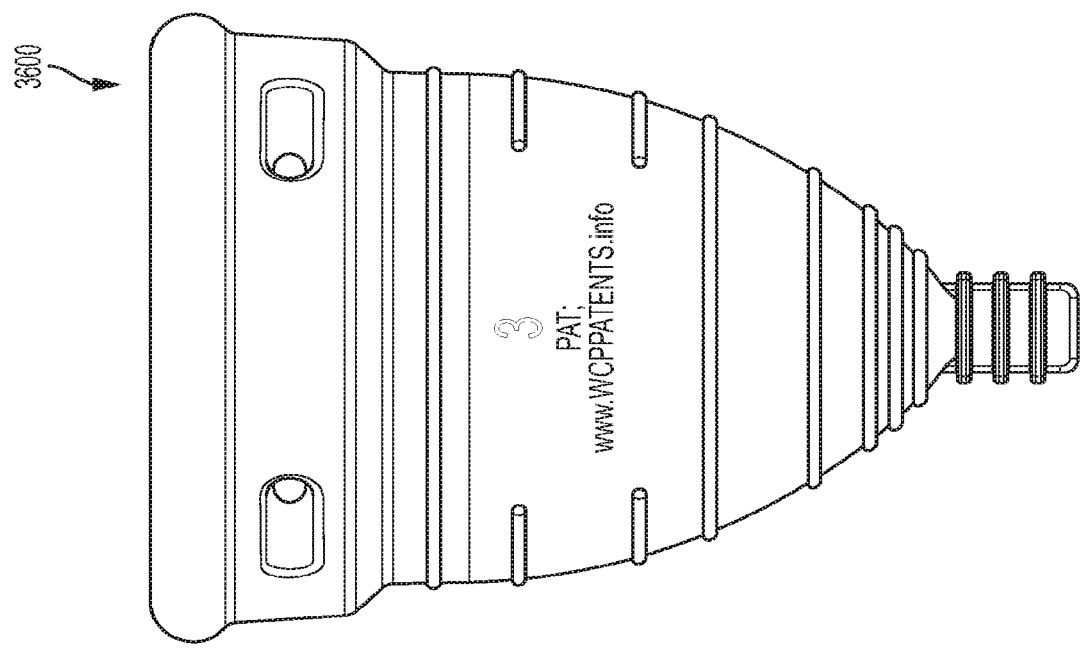
FIGS. 36A-36D illustrate a vaginal insert device, according to an embodiment of the present disclosure.
Figure 36A:
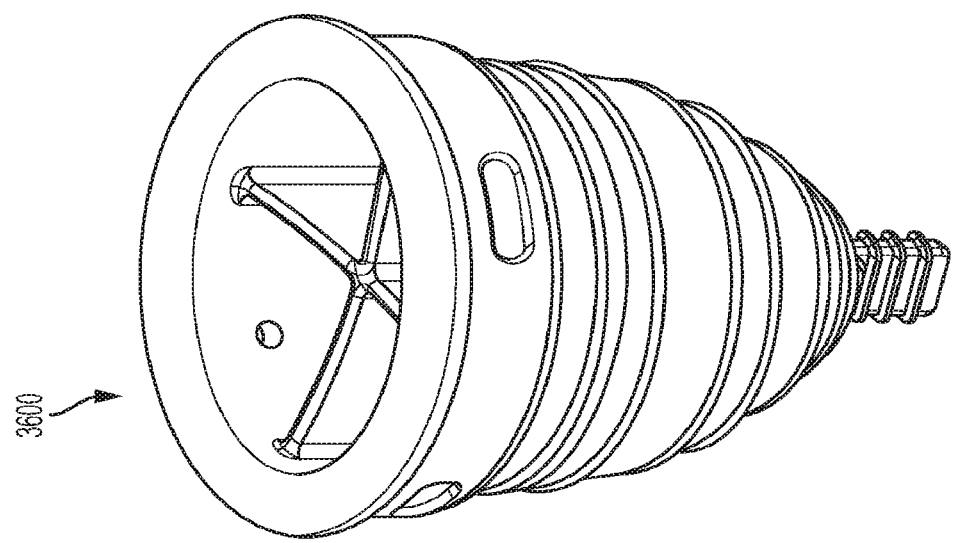
Figure 36D:
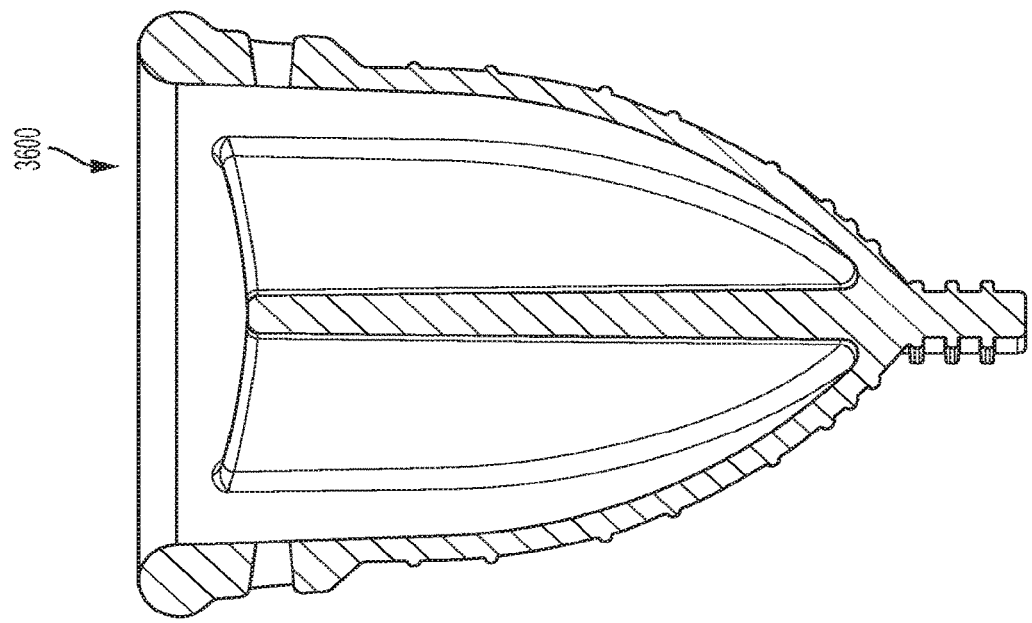
Figure 36C:
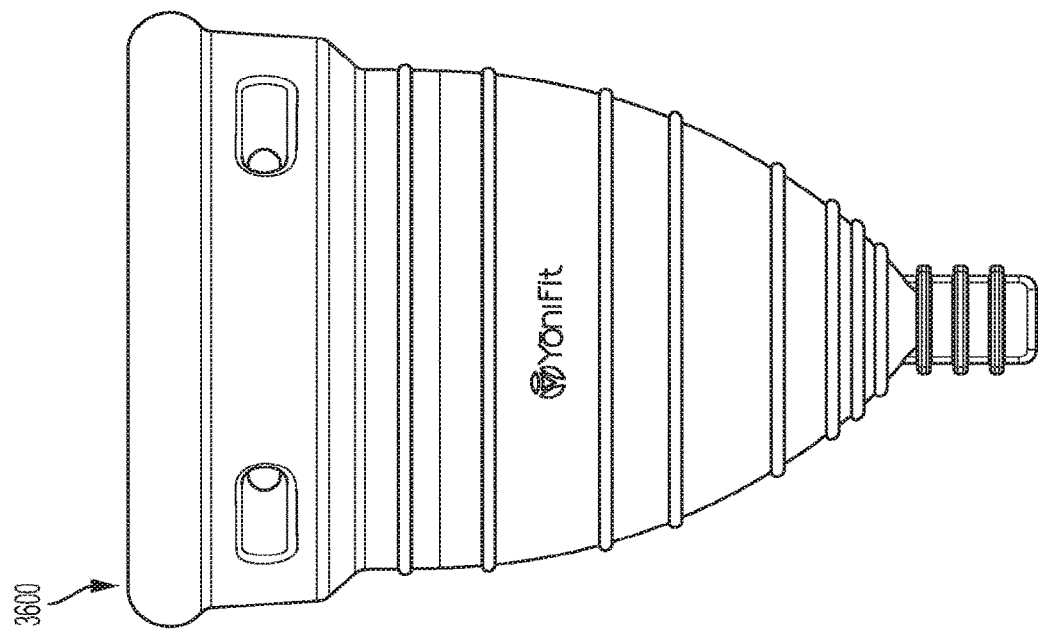
Figure 37B:
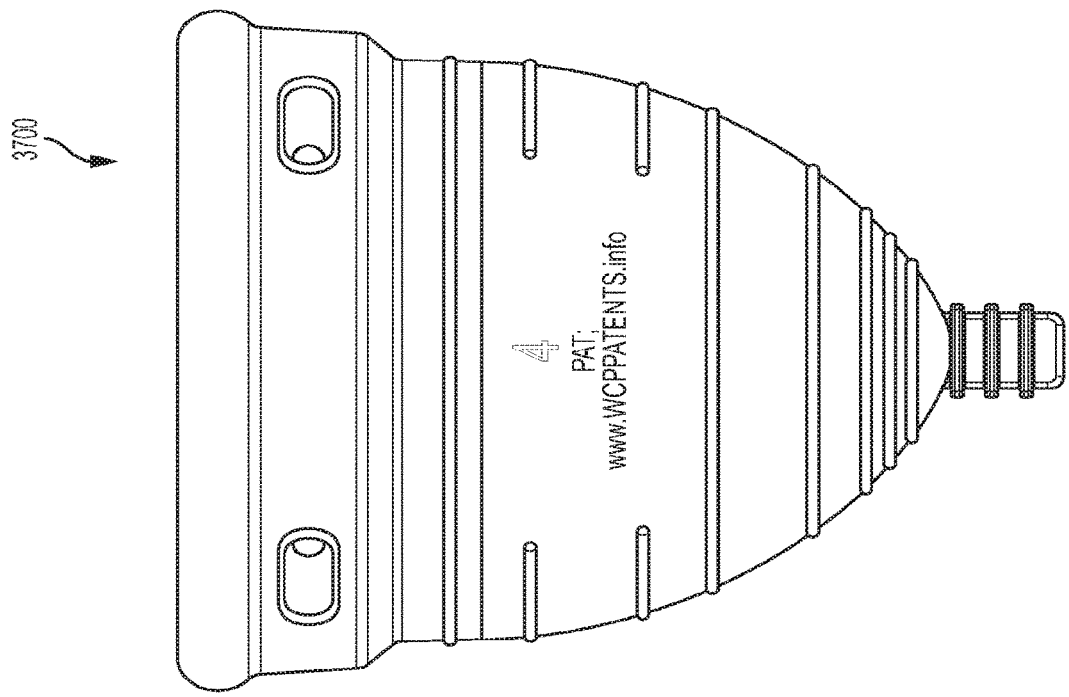
FIGS. 37A-37D illustrate a vaginal insert device, according to an embodiment of the present disclosure.
Figure 37A:
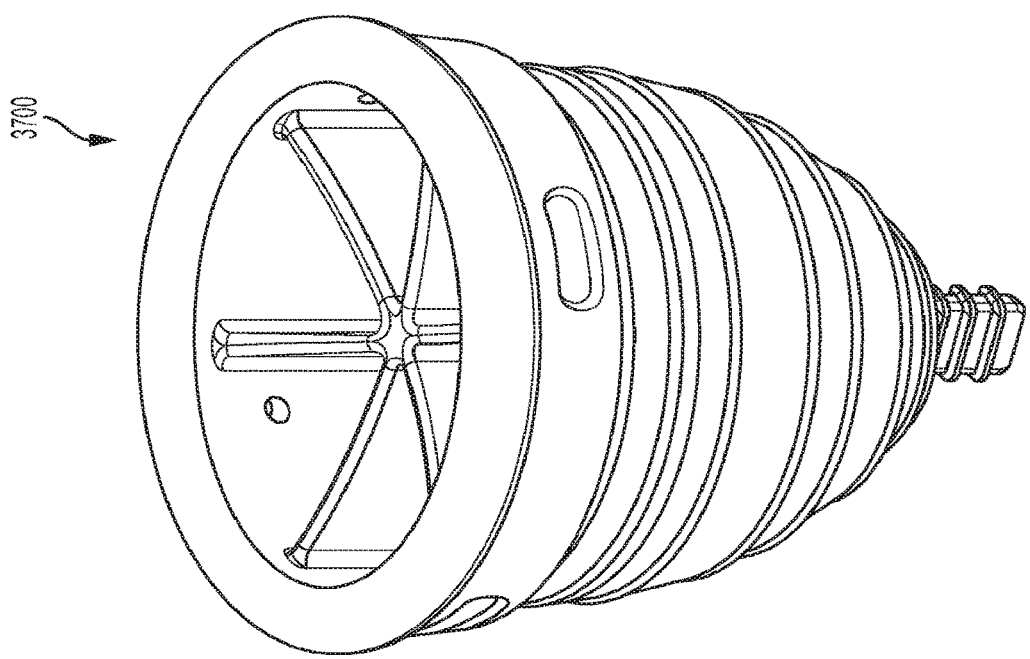
Figure 37D:
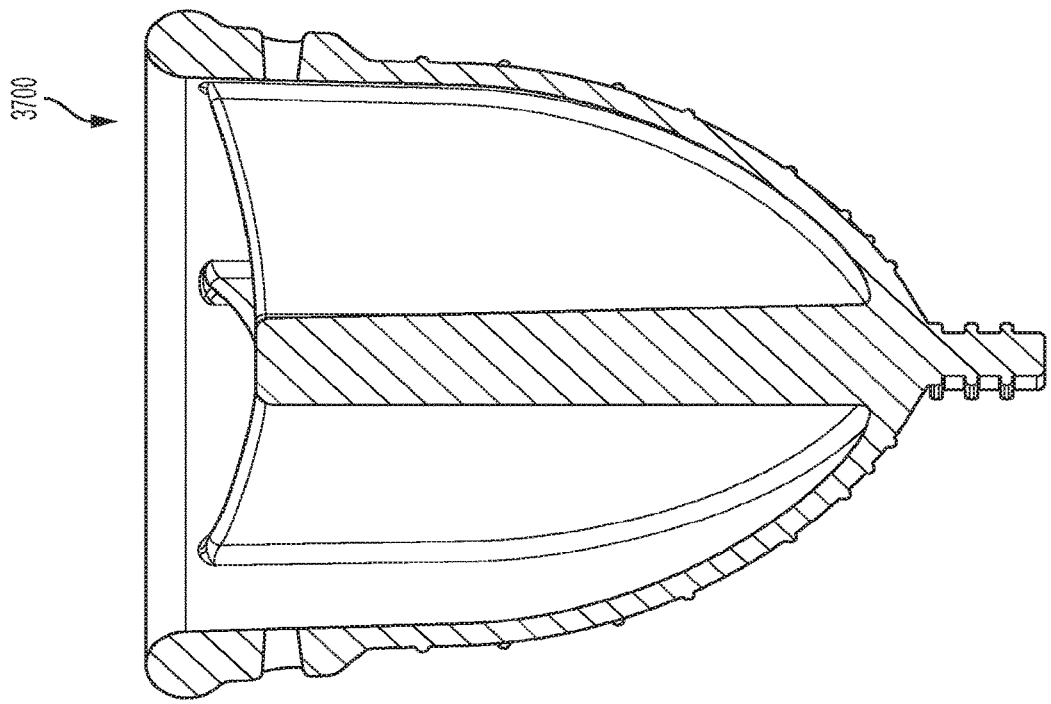
Figure 37C:
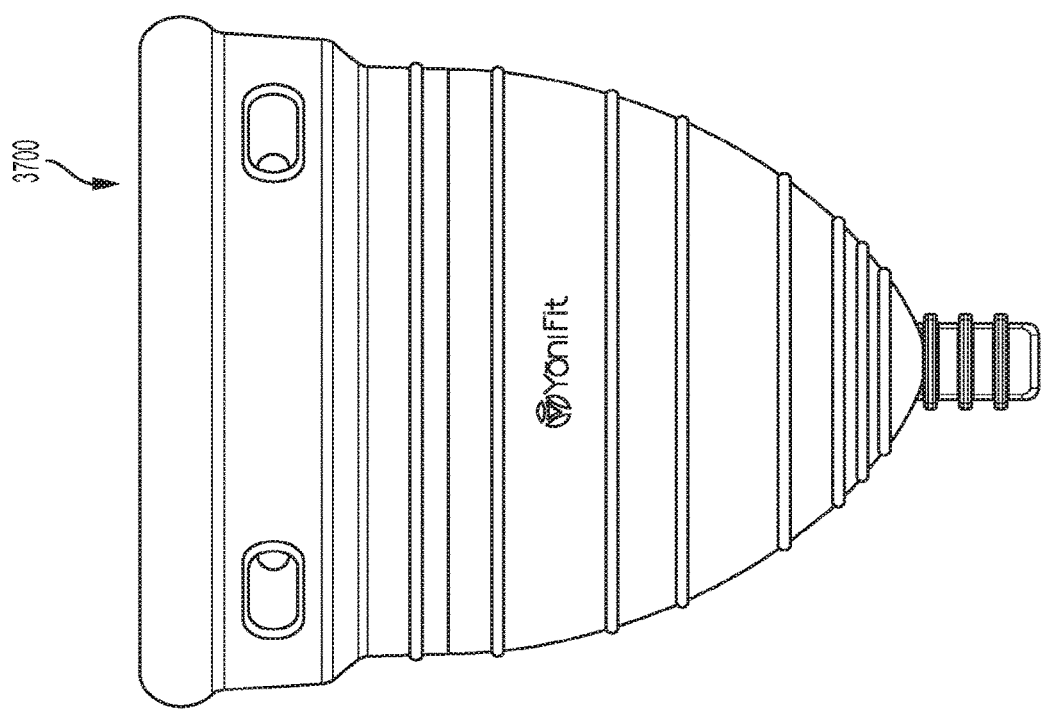
Figure 38A:
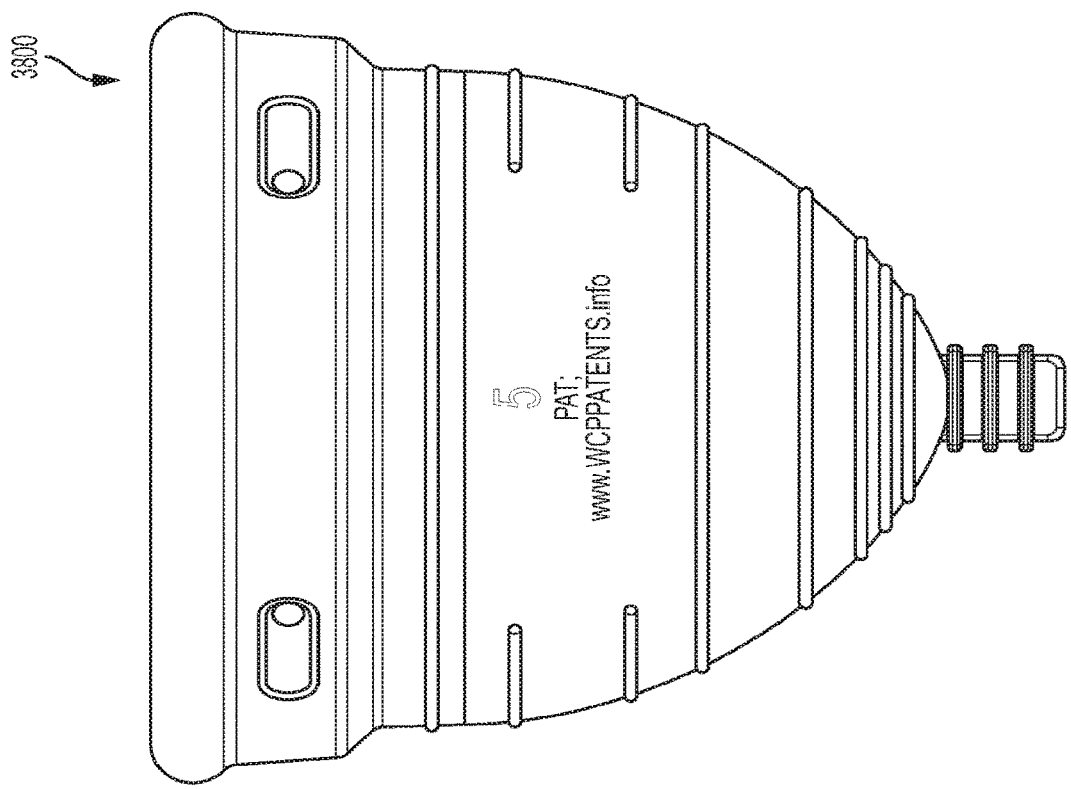
FIGS. 38A-38D illustrate a vaginal insert device, according to an embodiment of the present disclosure.
Figure 38B:
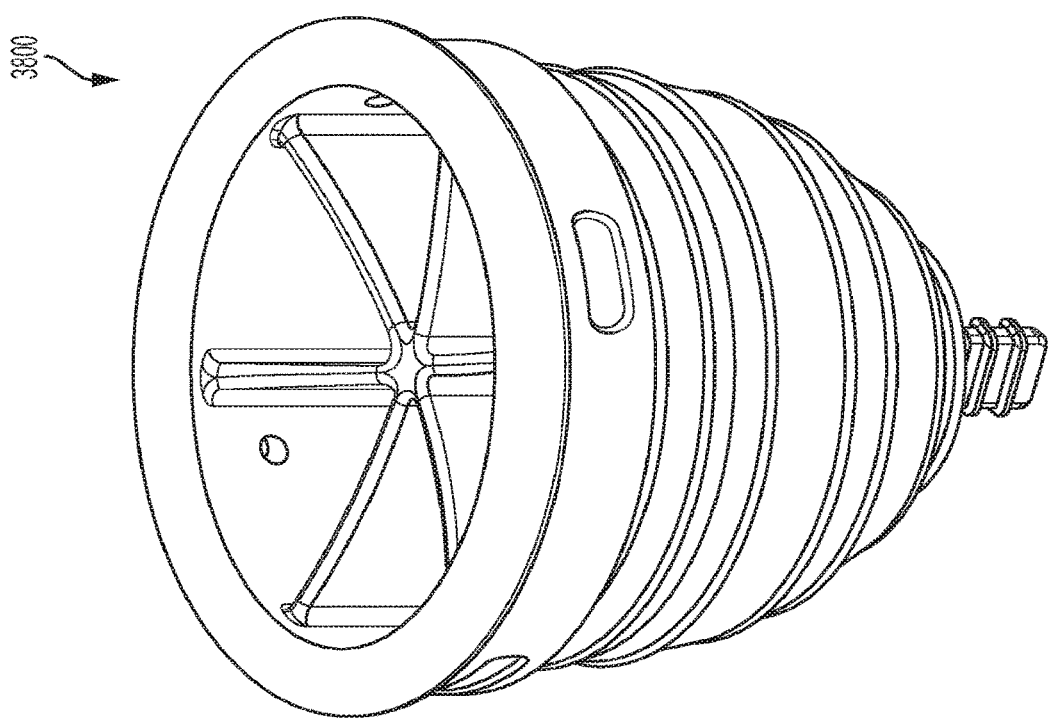
Figure 38D:
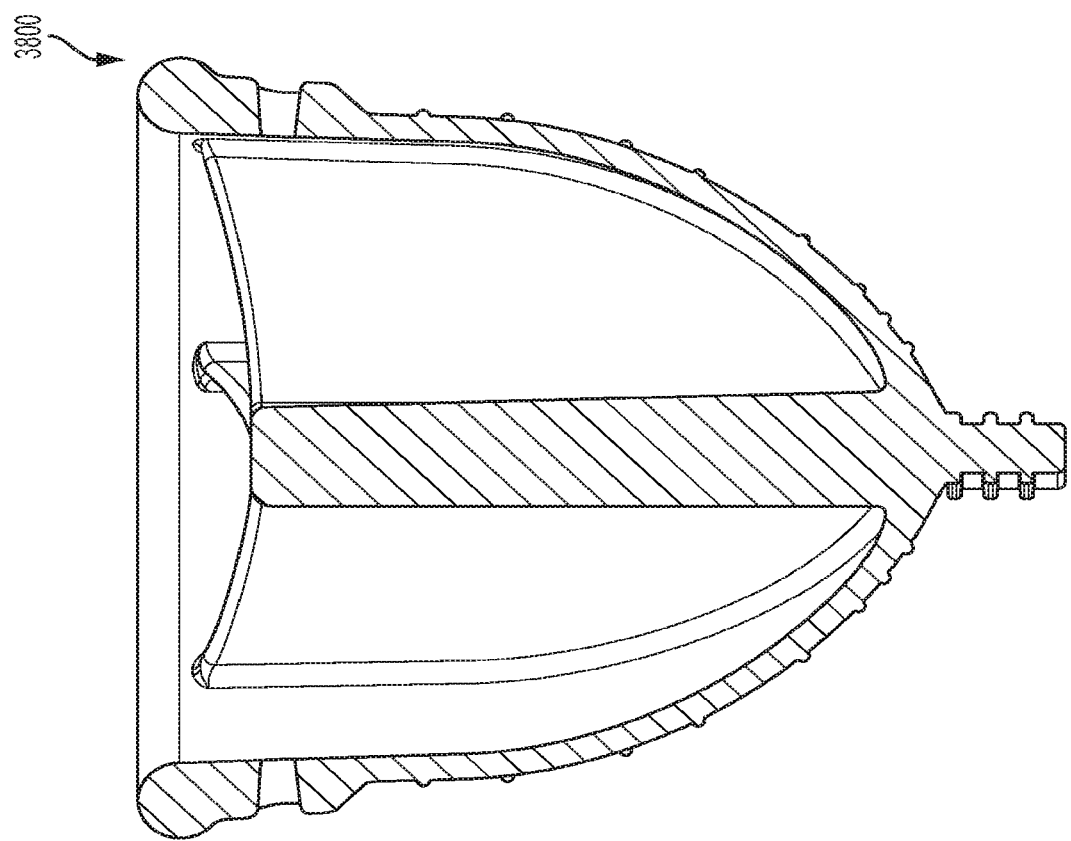
Figure 38C:
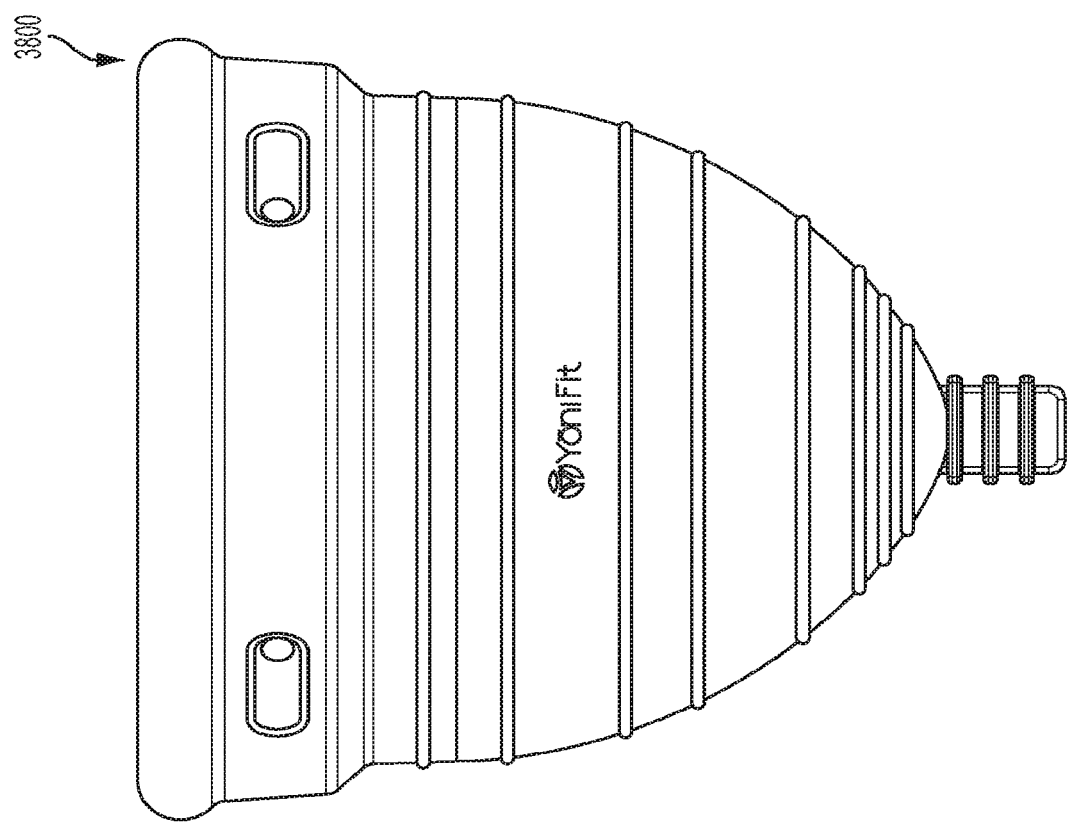

Referring to FIG. 33F, a detailed view of the ridges on the stem 244g is depicted. Each of the ridges may extend from the stem 244g by a distance Q of about 0.4 to about 0.6 mm, such as about 0.5 mm. Each of the ridges may have a thickness R of about 0.7 to about 0.9 mm, such as about 0.8 mm. Referring to FIG. 33G, a plan view of the stem 244g is depicted. The stem 244g may have an overall width T of about 5.8 to about 6.2 mm, such as about 6.0 mm and an overall width V of about 2.1 to about 2.5 mm, such as about 2.3 mm. Referring to FIG. 33H, a bottom view of the device 3300 is depicted.

Referring to FIGS. 33I-33L, perspective views of the device 3300 are shown. As shown, the stem 244g may be aligned with the rib 180. That is, a plane extending through a longitudinal center of the stem 244g may extend through a longitudinal center of at least a portion of the ribs. As shown in FIG. 34I, this results in the stem 244g being aligned with one rib 180 and perpendicular to the other rib 180. This alignment may allow for the device to be positioned within the vagina. This alignment may allow a user to know, just by touching the stem, that the rib is aligned with an intravaginal wall or that the rib is misaligned with the intravaginal wall. The alignment may assist in controlling the pressure and support applied by the device.

Referring to FIGS. 34-38, vaginal insert devices 3400, 3500, 3600, 3700, and 3800 are shown, respectively. The vaginal insert devices may be similar to the vaginal insert devices described in FIG. 33 with a different overall outer diameter. Accordingly, any of the previously described variations, uses, modifications, or features described with respect to any of the vaginal insert devices herein may be used, applied, or modified to the vaginal insert devices of FIGS. 34-38. For example, any of the variations, uses, modifications, or features with respect to the ribs 180, shape, ventilation openings, etc. may be provided on the vaginal insert devices of FIGS. 34-38. Additionally, any of the uses or accessories (e.g., the carrying case) may apply to the vaginal insert device of FIGS. 34-38 as previously described. Referring to FIGS. 34A-38A, a perspective view of each of the vaginal insert devices is shown with the rib 180 spaced a distance below the top surface of the device. The upper portion, rim, ribs, ventilation openings, methods of insertion, rotation, adjusting pressure, use, and any other features or embodiments described herein may be presented with the vaginal insert device. Referring to FIGS. 34B-38B, a side view of the vaginal insert devices is shown. The ridges and optional logo may be spaced equidistant along the outer surface of the upper portion of the vaginal insert device, as described with respect to previous embodiments. Referring to FIGS. 34C-38C, a side view rotated 90 degrees from the view of FIG. 34B-38B is depicted. The ridges on the stem 244g may be spaced for each other. Referring to FIG. 34D, a side cross-sectional view of the vaginal insert devices is depicted.

The vaginal insert devices may have a diameter J that is about 25 to about 50 mm, such as about 30 to about 45 mm, about 30 to about 36 mm (including about 33 mm), about 34 to about 40 mm (including about 37 mm), about 39 to about 45 mm (including about 42 mm), and including about 30 mm (FIG. 34), about 38 mm (FIG. 35), 42 mm (FIG. 36), 48 mm (FIG. 37), and about 52 mm (FIG. 38). The dimensions K, L, M, N, P, Q, R, T, V, X, Y, Z may be the same or within the same ranges for all of FIGS. 33-38. Alternatively, any of the dimensions may be different between the sizes to accommodate for changing anatomy of a woman. For example, in a smaller diameter device, the height, length of the stem, width of the rim and/or ridges, or combinations thereof may be sized differently (e.g., smaller) than a device having a larger diameter. In each of FIGS. 33-38, the stem 244g may be aligned with the rib 180 as described in IGS. 33I-33L. As previously described, the devices may include more than four ribs, such as six ribs. For example, in the larger sizes of FIGS. 37 and 38, six ribs may be provided in the manner previously described.

Figure 39:
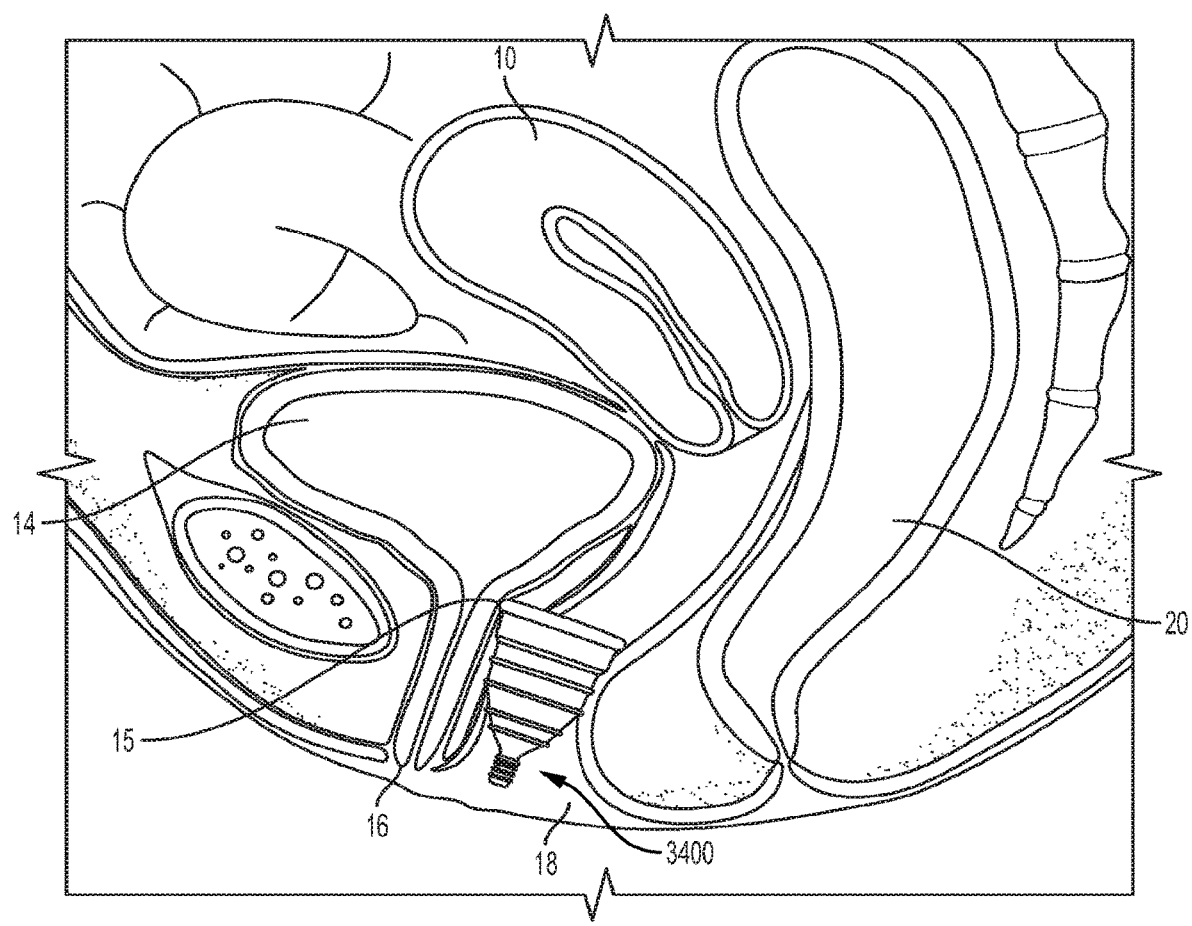
FIG. 39 illustrates a cross-section of the pelvic region of a female with an embodiment of the vaginal insert device inserted in the vagina.
Figure 40:
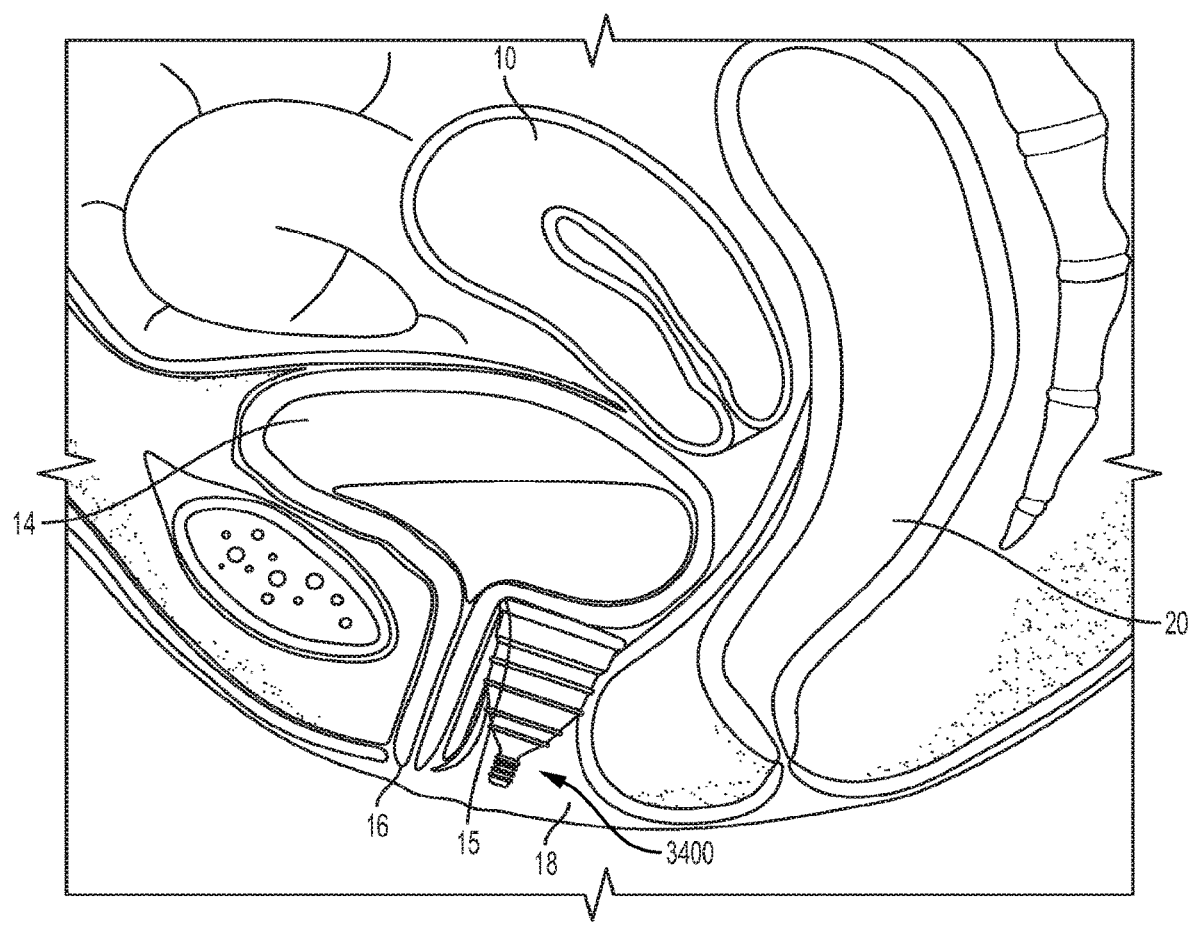
FIG. 40 illustrates a cross-section of the pelvic region of a female with an embodiment of the vaginal insert device inserted in the vagina.
Figure 41:
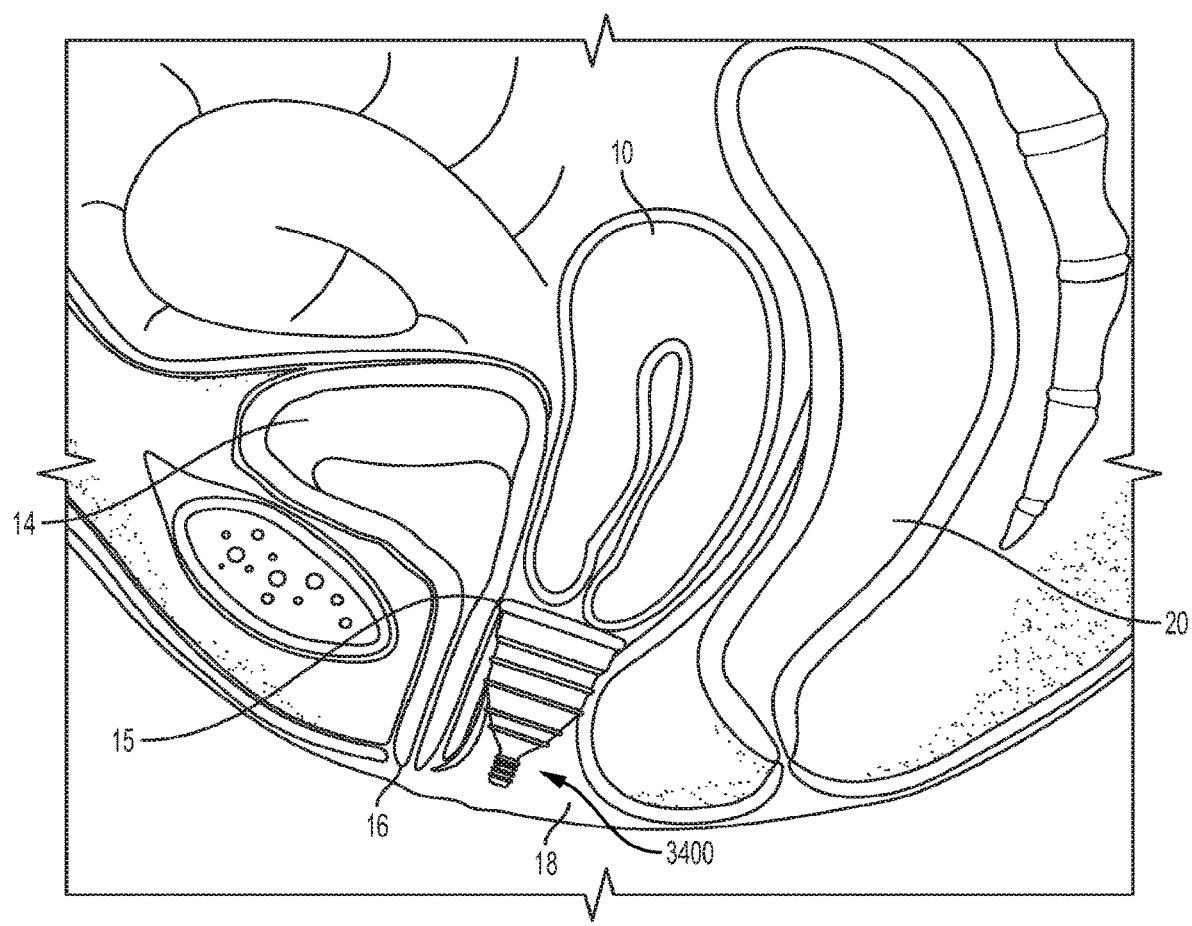
FIG. 41 illustrates a cross-section of the pelvic region of a female with an embodiment of the vaginal insert device inserted in the vagina.

Referring to FIGS. 39-41, the vaginal insert devices of FIGS. 16-20 and 26-38 may be inserted into a vagina 18 as described with respect to FIGS. 11-13. For example, the device, such as device 3400, may be inserted into the vagina to apply pressure to the urethral sphincter 16. The pressure may be applied at the bladder neck. As seen in FIG. 40, the device 3400 may apply pressure such that when the bladder is full, there is little or no leakage. The device 3400 is shown in FIG. 40 supporting the full bladder and thus also improving, preventing, or eliminating, or inhibiting prolapse. The support and assistance in preventing prolapse may be due to the pressure applied by the ribs and/or the rim of the device. FIG. 41 depicts the device 3400 inserted into the vagina 18 to support, manage, improve, prevent, or eliminate a prolapsed uterus.

In an exemplary embodiment, the vaginal insert device of the present disclosure may be used during exercise or other activity. For example the vaginal insert device may be inserted into the body in the aforementioned manner prior to (e.g., 5 to 60 minutes before) walking, running, strength training, cardiovascular activity, kickboxing, or other high intensity activity, etc. The vaginal insert device may hold or support the pelvic organs, bladder, and/or rectum during the activity. The vaginal insert device may prevent, eliminate, or inhibit prolapse or displacement of the organs during the activity. A user may insert the vaginal insert device into the body prior to performing the activity. The activity may cause stress or place pressure on the pelvic organs, bladder, and/or rectum. In the absence of the device, the stress or pressure associated with the activity may cause the pelvic organs, bladder, and/or rectum to displace and/or prolapse and may cause discomfort to the user during activity. The vaginal insert device may support the pelvic organs, bladder, and/or rectum such as to counteract, support, inhibit, or eliminate the discomfort, stress, or pressure caused by the activity onto the organs. A user may use the vaginal insert device only during activities or during both sedentary (e.g., sleeping, resting, sitting, etc.) and active times. In an embodiment, the user may use one size of the device during activities, and may then use another size of the device during less active or sedentary times. For example, the user may use a larger size of the device during activities, and may use a smaller size of the device during less active or sedentary times.

Figure 42:
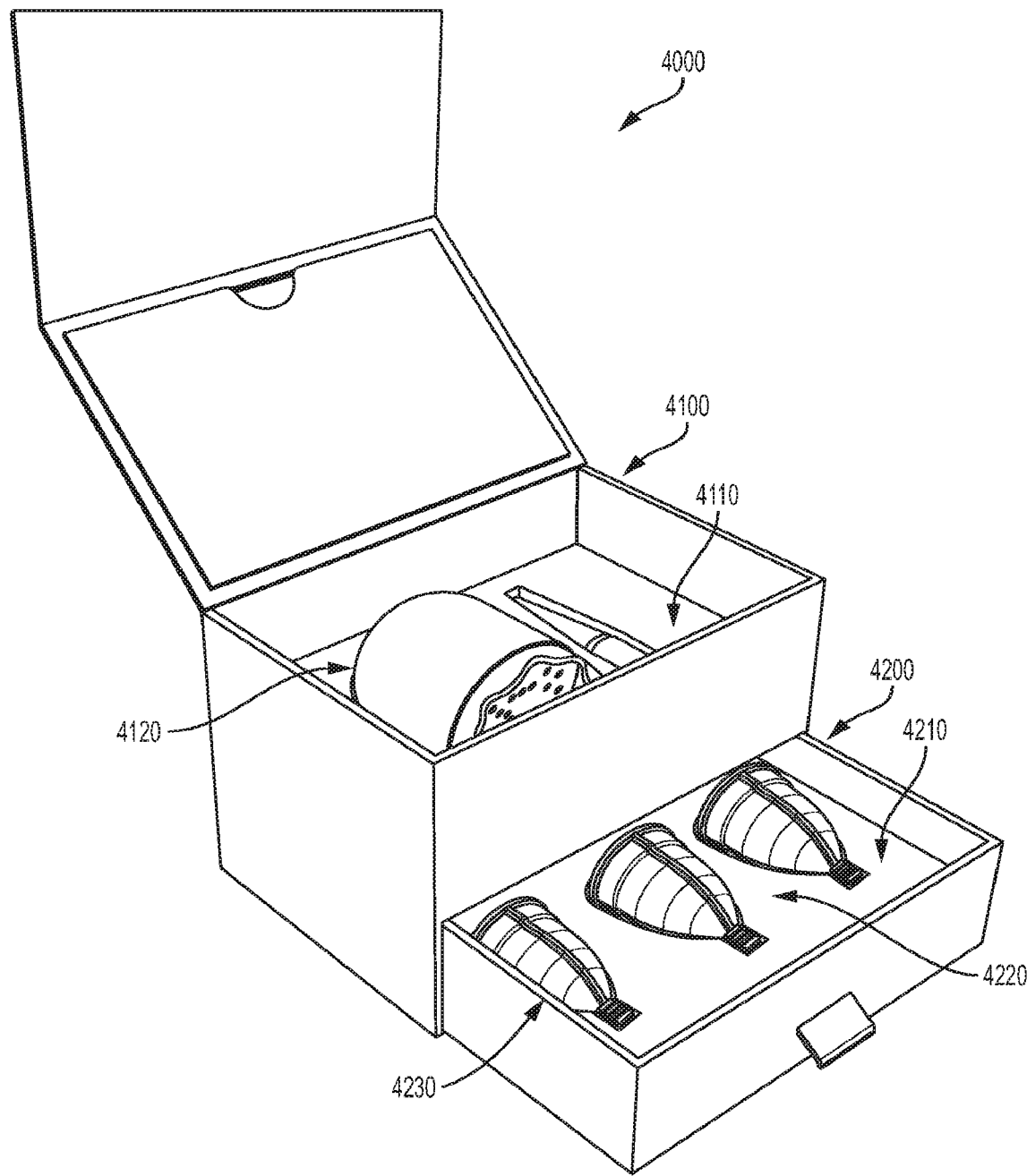
FIG. 42 illustrates a perspective view of a kit including vaginal insert devices of varying sizes, a carrying case, a drying rack, and a brush, in accordance with embodiments of the present disclosure.
Figure 43:
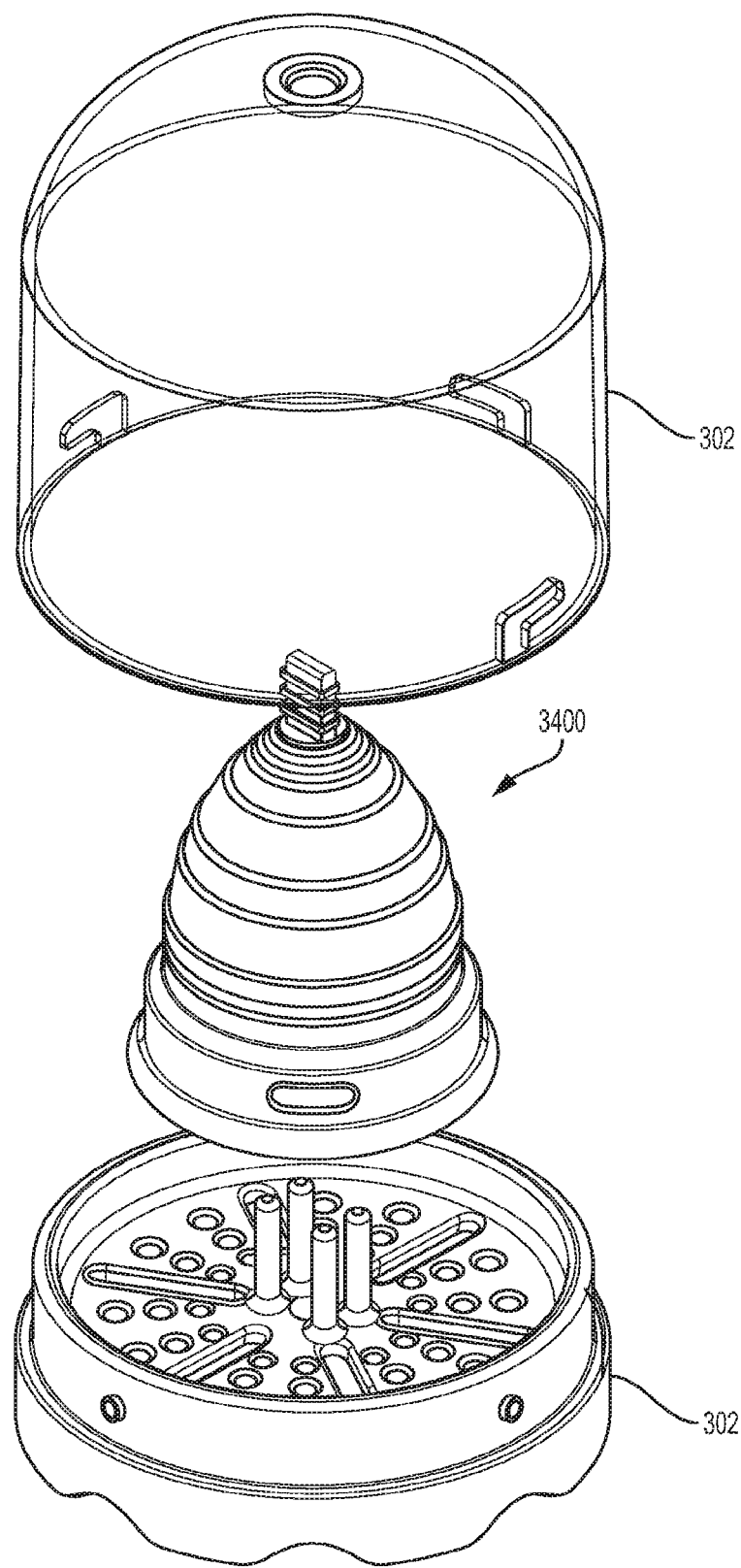
FIG. 43 illustrates an exploded perspective view of a carrying case, according to an embodiment of the present disclosure.

Referring to FIG. 42 a kit 4000 is shown. The kit 4000 may include one or more of a storage kit 4100 and a vaginal insert kit 4200. The storage kit 4100 may include a carrying case 4120 and an optional brush 4110. The carrying case 4120 may be the previously described carrying case and may include the previously described drying kit. The brush 4110 may be the previously described brush. The vaginal insert kit 4200 may include a plurality of vaginal insert devices 4210, 4220, and 4230. The plurality of devices may be provided in a plurality of sizes. In this manner, a user may select the desired size for a particular usage or performance. For example, a user may select a larger size device for more support in one usage and a smaller size device for support in another usage. The vaginal insert devices 4210, 4220, 4230 may be varying sizes or styles of any of the previously described vaginal insert devices. Alternatively, the kit 4000 may provide a plurality of vaginal insert devices of the same size.

In an embodiment, the kit 4000 may include the storage kit 4100 and the vaginal insert kit 4200 in a single compartment of the kit 4000. In some embodiments, the kit 4000 is a box with an attached or detached lid.

The vaginal insert devices 40, 100, 200, or any of the vaginal insert devices of FIGS. 27-38, may be formed of a material or multiple materials and parts which allows the devices to collapse, fold, or compress when pressed by a patient for insertion into the vagina or to be foldable for storage or to make smaller. A peak folding force may be about 1.5 to about 1.9 lbf, such as about 1.7 lbf. A peak folding force may be about 1.8 lbf to about 2.4 lbf, such as about 2.1 lbf for a material that is 40% stiffer than the material exhibiting a peak folding force of 1.7 lbf. Once in the vagina, the device may move or expand back from a folded or compressed configuration during insertion to the original configuration, such as, for example, as seen in FIG. 16. The durometer or hardness, density, size, shape and durability of material (e.g., a non-absorbent material, such as silicone) selected for the vaginal insert devices 40, 100, 200 may be selected based on the desired compressibility and collapsibility of the device and/or the pressure applied to the urethral sphincter, bladder neck or rectum. The durometer or hardness of the material (e.g., silicon) may be lower or softer for one size vaginal insert device and/or higher or harder for a different size vaginal insert device.

The device may be made of one material. However, some embodiments may be made of multiple parts and/or from one different material or a combination of different materials and may become detachable or attachable. The device may be disassembled and reassembled for cleaning, sterilization, impregnation of drug, weights or an indication strip or various technologies such as a Bluetooth chip, radio wave, microwave, or Wi-Fi connectivity capabilities.

Where rib 180 is provided, a softer or harder material may be used. The softer or harder material (e.g., silicone) may allow for more comfortable wearing while the rib 180 provides added pressure. That is, the rib 180 may accommodate for the pressure applied by a softer or harder material, thus allowing a more comfortable and effective device.

The vaginal insert devices of the present disclosure may have multiple functions. The primary function of the device, as previously described, may be to support the urethral sphincter, bladder neck, or bowel to reduce prevent, treat and/or eliminate incontinence or prevent or support prolapsed organs. Additionally, although the device may be an over-the-counter device, it may be impregnated with medication such as prescription or non-prescription homeopathic remedies or substances to address conditions for hormone levels, sexually transmitted diseases yeast infections, birth control, spermicide, as well as other substances with benefits such as antifungal or anti-infection substances that retard the growth of bacteria, fungus or diseases. The device may secrete the substance or medication. The device may be provided for hormone replacement therapy. As such, the device may be capable of drug-delivery to the vaginal cavity, for example drug delivery with a controlled, prolonged, or extended release profile. The drug delivery may be achieved by releasing drug from the outside or inside surfaces of the device and may be made from one or more than one materials or components that may be detachable or attachable. The device may also include diagnostic capabilities, such as by including an attachable/releasable or fixed indicator strip that may determine hormone levels, ovulation levels, pH levels, pelvic floor or muscle strength or as an early detection component for health benefits. The device may have a detachable component for use during the menstrual cycle or after or before sexual activity. It may also have a detachable component used for exercising the pelvic floor, such as weights. Although the embodiments may be non-prescription, parts of the device or embodiments of the device may be for drug delivery or to use as an indicator for diagnosis of diseases and conditions.

The vaginal insert devices of the present disclosure may further include weights which may be added or removed or may be made of a weighted material. The weights may exercise the pelvic floor muscles during exercise or Kegels or simply while the end user goes about their day the weight may force them to hold the device in place thus exercising the muscles.

The vaginal insert devices of the present disclosure may include weights, pellets, stainless steel pellets, indicator strip(s), a pressure sensor, nanotechnology, or other additions described herein. When additional features or components are included in the vaginal insert device of the present disclosure they may be placed into the mold prior to injection molding (or other manufacturing) such that they are integral with the device and/or they may be inserted with the material during injection molding (or other manufacturing) to be integral with the device. Alternatively, the additional features or components may be secured to the device by post processing, such as fastening, gluing, adhering, bonding, etc. to the device, walls of the device, indentations or recesses formed in the device specifically for the component, etc.

The vaginal insert devices of the present disclosure may be formed of a material which changes colors based on number of uses and/or based on the conditions of the vaginal environment (e.g., pH levels) or on the condition of the device itself. That is, a user may be able to remove the device and, based on the color, understanding that it is time for the device to be cleaned, recharged, replaced, and/or disposed of. A user may also remove the device and it may include diagnosing capabilities that indicate that the user is ovulating, has a yeast infection, sexually transmitted disease, certain hormone levels (e.g., an unhealthy hormone level) and/or an infection, etc.

The vaginal insert devices of the present disclosure may be implanted with a chip that communicates with Bluetooth, Wi-Fi capabilities, radio wave, microwave, or other technologies. Thus, a user may be able to communicate with a mobile device, such as phone or tablet. For example, the device may communicate a pH level or other indication of use that a user knows it is time to clean, recharge, replace, and/or dispose of the device. The device may communicate a number of pelvic floor exercise performed and be used to track pelvic floor strength. The device may communicate an environment within the vagina and be used to diagnose disease. The device may come with an app for mobile or other technology to monitor ovulation or urethral sphincter strength or pelvic floor strength. The device may be used with Wi-Fi. Additionally, if the device is worn during exercise, the device may hold the organs in place and prevent further prolapse due to long, hard constant movement such as running.

The vaginal insert devices of the present disclosure may prevent further movement of the organs and hold the organs in place. The rim, cone shape, and ridges work together to place pressure on the urethral sphincter, bladder neck, or bowel and prevent displacement of organs. The device 40, 100 described herein may place pressure on the urethral sphincter, bladder neck, or bowel. The device may be adjustable so that the device is comfortable for the user to wear. The device may be adjusted by movement of the stem. Over time, the device being in place may reduce the probability of further prolapse when the user is active, for example during running, walking, jumping jacks, etc.

The vaginal insert devices of the present disclosure may capture or collect vaginal discharge. The vaginal discharge may be evaluated, either by the device or after removal by a clinician. The discharge may be used to diagnose sexually transmitted diseases, if a woman is pregnant or ovulating, hormone levels, yeast infections or other infections not sexually transmitted, abnormal cells, interstitial cystitis, and may assist in managing interstitial cystitis. Although, in an embodiment, the device of the present disclosure does not create a seal or a suction, the device may collect some amount of discharge. Contrary to a menstrual cup, intended to collect all menstrual fluids, the device may collect a sample of discharge for the diagnosis and evaluation.

The removal portions of the present disclosure may be made of multiple parts and one, two, or a compound of materials which may become detachable, attachable, retractable and expandable. The stem may rotate and/or click in place to adjust the tension or size of the device. The stem may be used for re-orienting the device. It may have markings on the stem that protrude from it, correlating with the placement of the device or strength of the device such as an arrow or numbering system. It may have a hole in it to be used as an indicator or alongside a drying rack. The vaginal insert device may increase or decrease pressure as the stem is turned. The vaginal insert device may include attachable and/or interchangeable weights. The vaginal insert may include a strip or other attachment that may determine ovulation, pH levels, etc.

Although vaginal insert devices of the present disclosure are depicted herein as including a rib and rib sections or members thereof, in other embodiments, vaginal insert devices of the present disclosure do not include a rib or rib sections or members. For example, in one instance of a vaginal insert device that does not include a rib or rib sections or members, the device includes a rim analogous to rim 46, 146, 246, wherein, when the device is inserted into the patient, the rim is capable of providing sufficient pressure or force to the urethral sphincter, bladder neck, bowel, and/or vaginal wall to provide pelvic organ support to the patient. In an embodiment, the rim includes one or more portions that provide greater pressure or force than other portions. The one or more portions providing greater pressure or force may be thicker, more reinforced, or composed of materials with an increased hardness (e.g., harder silicone) than the other portions of the rim. The one or more portions of the rim that provide greater pressure or force may be aligned with the stem (much like the rib or rib sections or members may be aligned with the stem, as described herein) such that the user may be able to orient the one or more portions of the rim that provide greater pressure or force with a location adjacent to the vaginal wall that provides pelvic organ support, such as a location proximal to the urethral sphincter, bladder neck, or bowel.

Although vaginal insert devices of the present disclosure are depicted herein as including one or more hollow portions 58, 158 in the interior of the device (e.g., between rib sections or members), in other embodiments, vaginal insert devices of the present disclosure do not include such hollow portions but are solid or semi-solid, for example by being filled by the same material(s) as that of the vaginal insert device (e.g., silicone of the same or differing hardness) or by one or more different materials (e.g., foam or gel). A vaginal insert device that is solid or semi-solid may still be squeezed or deformed, as described herein, for easier insertion of the device, and the device may then resume its original shape after insertion. In one embodiment, the vaginal insert device includes a rib, which may be divided into rib sections or members to provide support as described herein, and a filling material in the hollow portions 158 between the rib sections or members. In an alternate embodiment, the vaginal insert device does not include a rib and includes a filling material in the hollow portion 58. In some instances of such an alternate embodiment, the device includes a rim having one or more portions that provide greater pressure or force than other portions, as described herein. In an embodiment, the upper portion may be closed, covered or otherwise blocked such that the inside of the device (either the hollow portions, solid portions, and/or semi solid-portions) are not exposed to atmosphere and/or to the inside of the vagina when inserted.

According to an embodiment, the present disclosure provides a method for applying pressure or force to a location of the vaginal wall of a patient, the method comprising inserting a vaginal insert device into the vagina of the patient, and orienting a force- or pressure-providing portion of the vaginal insert device so as to align the force- or pressure-providing portion with—or be adjacent to—the location of the vaginal wall of the patient. In certain embodiments, the location of the vaginal wall is proximal to the urethral sphincter, bladder neck, or bowel. In some embodiments, applying pressure or force to the location of the vaginal wall provides pelvic organ support to the patient. In certain instances, the vaginal insert device includes a rib or one or more rib sections or members as described herein, and the force- or pressure-providing portion of the vaginal insert device corresponds to the location(s) that the rib or one or more rib sections or members joins an interior wall of the device. In some embodiments, the vaginal insert device includes a rim (e.g., a circular rim, in plan view, as described herein), and the force- or pressure-providing portion of the vaginal insert device corresponds to one or more portions of the rim that provide greater pressure or force than other portions of the rim. In an embodiment, the vaginal insert device includes a stem, as described herein, which is aligned with the force- or pressure-providing portion of the vaginal insert device. In certain instances, orienting the force- or pressure-providing portion of the device includes rotating the device, such as by rotating the stem. In an embodiment, the vaginal insert device of the present disclosure may include components or features that align the device with the pelvic floor or the device itself may align the pelvic floor.

Although one embodiment of the vaginal insert device may be made from one material and from one part, other embodiments may be made of multiple parts and/or made from multiple materials. The parts may include accessories, such as detachable accessories. The parts may be, for example, an added piece for the menstrual cycle, to add weights for exercising the pelvic floor, indication strip to determine ovulation or pH levels, or a compound of materials or parts to administer medication. The device or portions thereof, may be expandable and retractable. The device may be semi-permeable to allow liquid, lubrication or medication to pass through it.

According to an embodiment, a vaginal insert device for managing, treating, improving, reducing, eliminating, or preventing incontinence, may include one or more of an upper portion having a cone-shaped body, an exterior wall and an interior wall; a stem extending from a base of the upper portion; one or more first ridges protruding outwardly from the exterior wall, and a rib protruding inwardly from the interior wall, the rib configured to apply pressure to an organ wall. The stem may include one or more second ridges protruding outwardly from an exterior surface of the stem. The stem may be one of conical, triangular, flat, or cross-shaped. The one or more first ridges may be are one or more of studs, knobs, buttons, words, numbers, symbols, logos, circular, semi-circular, protrusions, polygonal, triangular, square, or combinations thereof. The rib may include a plurality of intersecting ribs. The rib may be cross-shaped, "T" shaped, "X" shaped, "Y" shaped, "K" shaped, "V" shaped, triangular, or pentagonal. The rib may also may be star shaped and connect at one central place, more than one place or not at all. The rib may protrude from the exterior wall, wherein the rib extends from adjacent the rim to the base of the upper portion. One or more ventilation openings may occur in at least one of the upper portion or the rib. The device may support an organ wall that may be at least one of a urethral wall, a bladder wall, a colon wall, or a rectal wall.

According to an embodiment, a kit for reducing or eliminating incontinence may include one or more of a first vaginal insert device; a carrying case, the carrying case including a base and a cover; and a drying rack, and an optional brush and cleanser. The kit may include a second vaginal insert device, the second vaginal insert device having a different outer diameter than the first vaginal insert device (e.g., a larger or smaller vaginal insert device). The first vaginal insert device may be one of a plurality of vaginal insert devices, the plurality of vaginal insert devices each having the same or a different outer diameter, durometer or hardness, shape, density, size or durability. The base may have a curved lower surface configured to rest flat on a surface. The cover can have a substantially cylindrical lower portion and a substantially semi-spherical top, the cover configured to mate with the base. A rim of the first vaginal insert device may be configured to fit on and mate with a first upper surface of the base. The cover may be configured to fit over the first vaginal insert device to fit on and mate with a second upper surface of the base. The drying rack, in an embodiment, may include a cylindrical base with one or more of a plurality of holes, one or more protrusions, and one or more latches.

According to an embodiment, a method for reducing or eliminating incontinence in a female patient may include inserting into the vagina of the patient a vaginal insert device as described herein. For example, the method may comprise inserting into the vagina, a vaginal insert device having a body, a rim, a rib, and a stem; and applying pressure to an organ wall with the rim and the rib of the vaginal insert device. The method may include adjusting the pressure applied to the organ walls includes rotating the vaginal insert device by rotating the rib.

According to an embodiment, a method for adjusting the pressure of the wall of an organ of a patient may include inserting into a patient a vaginal insert device as described herein. For example, the method may comprise, inserting into the patient the vaginal insert device, aligning a rib of the vaginal insert device with an organ wall, decreasing a pressure on the organ wall by rotating the vaginal insert device to misalign the rib and the organ wall. The rotating may be done with a stem extending from the vaginal insert device. The device may expand or retract when rotated to adjust a pressure on the vaginal wall.

According to an embodiment, a method for adjusting the pressure of the wall of an organ may include inserting a vaginal insert device, misaligning a rib of the vaginal insert device with an organ wall, increasing a pressure on the organ wall by rotating the vaginal insert device to align the rib and the organ wall. The rotating may be done with a stem extending from the vaginal insert device. The device may expand or retract when rotated to adjust a pressure on the vaginal wall.

Current menstrual cup products may not be used to prevent, reduce, or eliminate incontinence. The cervix or bladder may settle into the menstrual cup of the device and create a suction. When the women attempts to remove the device she may pull on the organs, creating an injury for herself. The internal rib and/or ventilation of the vaginal insert device of the pending disclosure eliminates the risk of the organs settling into the device as well as suctioning to the cervix or bladder. The extra support provided by the vaginal insert device of the pending disclosure is beneficial for the safety of the patient, particularly, as is common, for patients having cervical atrophy or no cervix at all and for whom the bladder will or does droop or descend through the vagina (prolapse).

Menstrual cups are intended to create a seal on the cervix, thereby creating a suction. Creating a seal eliminates the possibility of blood leaking. Such a suction may cause the user to pull on her organs during removal. Accordingly, in certain embodiments of the devices disclosed herein, a hole is provided in either in the bottom or on the sides of the device, to prevent suction. in some embodiments, the vaginal insert device of the pending disclosure supports the cervix. The vaginal insert device of the pending disclosure may place pressure (therapy force) on the urethral sphincter through the intravaginal canal. In contrast, the menstrual cups do not place pressure on the urethral sphincter. Additionally, menstrual cups may seal against the organ walls, preventing blood flow out side of the menstrual cup. The vaginal insert device of the present disclosure does not need to be fluid tight and/or seal against the organ walls. In fact, such a seal/fluid tightness may result in the suction previously described.

In accordance with the teachings of the present disclosure, the disadvantages and problems associated with known pessaries may be substantially reduced or eliminated.

In accordance with embodiments of the present disclosure, a vaginal insert device for use in managing, improving, eliminating or preventing symptoms associated with pelvic organ prolapse, urinary or fecal incontinence, or both pelvic organ prolapse and urinary/fecal incontinence may include an upper portion, which is made of an elastic and non-absorbent material, having a cone-shaped body, having a circular transverse cross-section throughout its length, having a wall with an interior side and an exterior side, an upper open end, a lower end, and a hollow interior, wherein the circumference of the upper portion decreases from the upper open end to the lower end, wherein the upper open end of the upper portion is the innermost portion of the vaginal insert device during insertion, and wherein the wall of the upper portion may be squeezed to make the upper portion more compact for easier insertion of the vaginal insert device, and wherein the wall expands back to its original shape after insertion. Such vaginal insert device may further include: an optional exterior rim surrounding and protruding from the exterior side of the wall of the upper portion and being adjacent to the upper open end; and a plurality of ridges surrounding and protruding from the exterior side of the wall of the upper portion and being spaced apart from the upper open end to the lower end.

In certain embodiments, the present disclosure is directed to a vaginal insert device for use in managing, improving, eliminating, treating and/or preventing symptoms associated with pelvic organ prolapse, urinary and/or fecal incontinence, or any combination thereof. In some instances, said device includes an upper portion optionally made of an elastic and/or non-absorbent material. In some embodiments, the upper portion has one or more of the following features: a body, a circular or oval transverse cross-section throughout or partially throughout its length, a wall with an interior side and an exterior side, an upper open end, a lower end, and a hollow or semi-hollow interior. In certain embodiments, the body has a cone shape wherein the base of the cone corresponds to the upper open end and the cone tapers on progression to the lower end. In some instances, the circumference of the upper portion decreases from the upper open end to the lower end. In certain embodiments, the upper open end of the upper portion is the innermost portion of the vaginal insert device during insertion, i.e., the upper portion is the portion of the device that is inserted first into the vagina. In certain instances, the wall of the upper portion may be squeezed to make the upper portion more compact for easier insertion of the vaginal insert device. In some embodiments, the wall expands back to its original shape after insertion. The vaginal insert device may further include an optional exterior rim surrounding and protruding from the exterior side of the wall of the upper portion and being adjacent to the upper open end. In some embodiments, the device includes a plurality of ridges surrounding and protruding from the exterior side of the wall of the upper portion and being spaced apart (e.g., at regular, irregular, increasing, or decreasing intervals) from the upper open end to the lower end.

In accordance with these and other embodiments of the present disclosure, a vaginal insert device may include a removal portion extending from the lower end of the upper portion, wherein the removal portion may be accessed from the exterior of a vagina when the vaginal insert device is inserted in the vagina, and wherein the removal portion assists in removal of the vaginal insert device from the vagina. The removal portion may be a string or a stem. In the embodiment where the removal portion is a stem, the stem may extend from the lower end of the upper portion, wherein the upper portion and the stem may be an integral one-piece but may have multiple detachable parts of the device made from the elastic and non-absorbent material or other materials, wherein the stem has a cone-shaped body, having a circular transverse cross-section throughout its length, having a wall, an upper end, a lower open end, and a hollow interior, and wherein the circumference of the stem increases from the upper end to the lower open end. The removal portion may also have a plurality of ridges like the upper portion.

In some embodiments, the present disclosure is directed to a vaginal insert device that includes a removal portion extending from the lower end of the body of the device. In certain embodiments, the removal portion may be accessed from the exterior of a vagina when the vaginal insert device is inserted in the vagina. In some instances, the removal portion assists in removal of the vaginal insert device from the vagina. The removal portion may be a string, stem, tab, flap, or other protuberance from the lower end of the body of the device. In certain instances, the body of the device (e.g., including the upper portion) and the removal portion (e.g., when a stem, tab or flap) may be an integral structure, such as an integral molded silicone structure. In some embodiments, the integral structure may have multiple detachable parts made from the elastic and/or non-absorbent material or other materials. In certain embodiments, the removal portion (e.g., when a stem, tab or flap) has one or more of the following features: a body, a circular transverse cross-section throughout or partially throughout its length, a wall, an upper end, a lower open end, and a hollow or semi-hollow interior. In certain embodiments, the body has a cone shape, for example, a cone shape that tapers from a base to a region joined to the body of the device, such as the upper portion. In some instances, the circumference of the removal portion (e.g., when a circular stem, tab or flap) increases from the upper end to the lower open end. The removal portion may also include a plurality of ridges, nubs, bumps, divots, or other structural surface features on the exterior of the removal portion, said structural features may facilitate gripping of the removal portion (and therefore the device) by the fingers of a user. In some, embodiments, the removal portion has a rectangular or box shape that projects from the bottom portion of the body of the device.

In accordance with these and other embodiments of the present disclosure, a vaginal insert device may include one or more ventilation openings (e.g., holes, slits, gaps, or apertures). A ventilation opening may be located at the point where the lower end of the upper portion and a stem intersect. One or more ventilation openings may be located in the wall or the rim on the upper portion. The ventilation opening may be used as a position indicator, for ventilation, or for both a position indicator and ventilation.

In accordance with these and other embodiments of the present disclosure, a vaginal insert device may include an optional exterior rim which is optionally circular and has a first section and a second section. In certain instances, the first section protrudes from the exterior side of the wall of the upper portion a greater distance than the second section. The rim may be different sizes, and thicknesses. It may be thinner at one side and thicker at the opposing side. The rim may expand or retract for therapy force and support.

In accordance with these and other embodiments of the present disclosure, a vaginal insert device may include an applicator used during insertion and/or removal of the device. In some embodiments, the applicator contains at least the upper portion when it is in a more compact shape. The applicator may attach and detach from the device. The applicator may work as an indicator for positioning, expanding, and/or retracting the device. The applicator may have indicators for positioning such as a ridge, arrow, bump, protrusion, lettering or numbering system. The applicator may have indentions or holes to indicate position. The applicator and device may click into place or otherwise fasten together.

Medical and other advantages of the present disclosure may be readily apparent to one skilled in the art from the figures, description and claims included herein. The objects and advantages of the embodiments will be realized and achieved at least by the elements, features, and combinations particularly pointed out in the claims.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus, device or system or a component, section, or portion of an apparatus, device or system being adapted to, arranged to, capable of, configured to, enabled to, operable to, or operative to perform a particular function encompasses that apparatus, device, system, or component, whether or not it or that particular function is used, activated, turned on, or unlocked, as long as that apparatus, system, device or component is so adapted, arranged, capable, configured, enabled, operable, or operative.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

The invention claimed is:

1. A method for using a vaginal insert device, the method comprising:
    inserting the vaginal insert device into a vagina, the vaginal insert device having a cone-shaped body with a rib extending within an inner portion of the cone-shaped body;
    orienting the rib with respect to an organ wall by rotating a stem extending downward from the cone-shaped body, the stem having a stem plane created by a width of the stem that is parallel to and coplanar with a rib plane created by the rib;
    applying a therapy force to the organ wall through orientation of the rib; and
    adjusting the therapy force by:
        rotating the stem to align the stem and the rib with the organ wall to form an aligned position that increases the therapy force; or
        rotating the stem to not align the stem and the rib with the organ wall to form a misaligned position that decreases the therapy force.

2. The method of claim 1, wherein rotating the stem to the misaligned position comprises rotating the device 45 degrees from the aligned position.

3. The method of claim 1, further comprising reducing the therapy force by 50 percent by rotating the stem from the aligned position to the misaligned position.

4. The method of claim 1, wherein applying the therapy force to the organ wall improves, manages, treats, prevents, and/or eliminates symptoms associated with pelvic organ prolapse, urinary incontinence, fecal incontinence, or combinations thereof.

5. The method of claim 1, further comprising increasing the therapy force prior to and during exercising and decreasing the therapy force after exercising.

6. The method of claim 1, further comprising removing the vaginal insert device by grasping the stem and pulling the vaginal insert device out of the vagina.

7. The method of claim 1, further comprising applying the therapy force with a rim of the cone-shaped body when the stem is in the misaligned position and applying the therapy force with the rim and the rib when the stem is in the aligned position.

8. The method of claim 1, wherein the rib includes a first rib portion and a second rib portion together forming a cross-shaped rib in plan view, wherein each of the first rib portion and the second rib portion have a rib plane, and wherein the stem is parallel to and coplanar with the rib plane of one of the first rib portion or the second rib portion.

9. The method of claim 1, wherein the rib includes a first rib portion, a second rib portion, and a third rib portion together forming a star-shaped rib in plan view, wherein each of the first rib portion, the second rib portion, and the third rib portion have a rib plane, and wherein the stem is parallel to and coplanar with the rib plane of one of the first rib portion, the second rib portion, or the third rib portion.

10. The method of claim 1, wherein the rib prevents tissue from descending into the cone-shaped body.

11. the method of claim 1, wherein rotating the stem is performed by grasping and rotating a lower end of the cone-shaped body and the stem.

12. the method of claim 1, wherein rotating the stem is performed by grasping and rotating the stem alone.

13. A vaginal insert device for applying pressure to an organ wall, the vaginal insert device comprising:
 a cone-shaped body having an inner portion, an upper end, a lower end, and a longitudinal axis extending from the upper end to the lower end;
 a rib extending within the inner portion of the cone-shaped body, the rib having a rib plane extending parallel to the longitudinal axis; and
 a stem extending downward from the cone-shaped body, the stem having a stem plane created by a width of the stem and extending parallel to the longitudinal axis, the stem plane being parallel to and coplanar with the rib plane such that a position of the stem correlates to a position of the rib with respect to the organ wall.

14. The vaginal insert device of claim 13, wherein the rib includes a first rib portion and a second rib portion together forming a cross-shaped rib in plan view, wherein each of the first rib portion and the second rib portion have a rib plane, and wherein the stem is parallel to and coplanar with the rib plane of one of the first rib portion or the second rib portion.

15. The vaginal insert device of claim 13, wherein the rib includes a first rib portion, a second rib portion, and a third rib portion together forming a star-shaped rib in plan view, wherein each of the first rib portion, the second rib portion, and the third rib portion have a rib plane, and wherein the stem is parallel to and coplanar with the rib plane of one of the first rib portion, the second rib portion, or the third rib portion.

16. The vaginal insert device of claim 13, wherein the stem is configured to allow positioning, rotation, or both of the vaginal insert device once the vaginal insert device is inserted into the vagina.

17. The vaginal insert device of claim 13, wherein the stem is flat.

18. The vaginal insert device of claim 13, wherein the stem is rectangular.

19. The vaginal insert device of claim 13, wherein the rib includes two or more members spaced equidistantly around a circumference of the inner portion of the cone-shaped body, the two or more members meeting at a center point of the cone-shaped body.

20. The vaginal insert device of claim 13, wherein the stem, due to a correlation of the stem plane and the rib plane, is configured to selectively adjust a pressure applied by the vaginal insert device to the organ wall.

21. A vaginal insert device for applying pressure to an organ wall, the vaginal insert device comprising:
 a cone-shaped body having an inner portion;
 a rib extending within the inner portion of the cone-shaped body, the rib having a rib plane; and
 a stem extending downward from the cone-shaped body, the stem having a stem plane created by a width of the stem, the stem plane being parallel to and coplanar with the rib plane such that a position of the stem correlates to a position of the rib with respect to the organ wall,
 wherein the rib includes a first rib portion and a second rib portion together forming a cross-shaped rib in plan view, wherein each of the first rib portion and the second rib portion have a rib plane, and wherein the stem is parallel to and coplanar with the rib plane of one of the first rib portion or the second rib portion.

22. A vaginal insert device for applying pressure to an organ wall, the vaginal insert device comprising:
 a cone-shaped body having an inner portion;
 a rib extending within the inner portion of the cone-shaped body, the rib having a rib plane; and
 a stem extending downward from the cone-shaped body, the stem having a stem plane created by a width of the stem, the stem plane being parallel to and coplanar with the rib plane such that a position of the stem correlates to a position of the rib with respect to the organ wall,
 wherein the rib includes a first rib portion, a second rib portion, and a third rib portion together forming a star-shaped rib in plan view,
 wherein each of the first rib portion, the second rib portion, and the third rib portion have a rib plane, and wherein the stem is parallel to and coplanar with the rib plane of one of the first rib portion, the second rib portion, or the third rib portion.

23. A vaginal insert device for applying pressure to an organ wall, the vaginal insert device comprising:
 a cone-shaped body having an inner portion;
 a rib extending within the inner portion of the cone-shaped body, the rib having a rib plane; and
 a stem extending downward from the cone-shaped body, the stem having a stem plane created by a width of the stem, the stem plane being parallel to and coplanar with the rib plane such that a position of the stem correlates to a position of the rib with respect to the organ wall,
 wherein the rib includes two or more members spaced equidistantly around a circumference of the inner portion of the cone-shaped body, the two or more members meeting at a center point of the cone-shaped body.

* * * * *